(12) United States Patent
Pontillo et al.

(10) Patent No.: US 7,378,552 B2
(45) Date of Patent: May 27, 2008

(54) MONOAMINE RE-UPTAKE INHIBITORS AND METHODS RELATING THERETO

(75) Inventors: Joseph Pontillo, San Diego, CA (US); Yinghong Gao, San Diego, CA (US); Warren S. Wade, San Diego, CA (US); Dongpei Wu, San Diego, CA (US); Wendy K. Eccles, San Diego, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 56 days.

(21) Appl. No.: 11/422,843

(22) Filed: Jun. 7, 2006

(65) Prior Publication Data

US 2006/0276454 A1   Dec. 7, 2006

Related U.S. Application Data

(60) Provisional application No. 60/752,259, filed on Dec. 19, 2005, provisional application No. 60/687,940, filed on Jun. 7, 2005.

(51) Int. Cl.
    C07C 255/00    (2006.01)
    A61K 31/135    (2006.01)
(52) U.S. Cl. ............... 564/336; 558/411; 514/649
(58) Field of Classification Search ........... 564/336; 558/411; 514/649
    See application file for complete search history.

(56) References Cited

U.S. PATENT DOCUMENTS

| | | | |
|---|---|---|---|
| 2,947,756 A | | 2/1960 | Huebner |
| 3,072,716 A | * | 1/1963 | Huebner ............ 562/595 |
| 3,105,836 A | | 10/1963 | Huebner |
| 4,535,186 A | * | 8/1985 | Husbands et al. ........ 564/336 |
| 5,149,714 A | | 9/1992 | Freedman |
| 6,136,803 A | | 10/2000 | Freedman et al. |
| 6,218,427 B1 | | 4/2001 | Ishizuka et al. |
| 6,479,702 B1 | | 11/2002 | Saigo et al. |
| 2003/0166708 A1 | * | 9/2003 | Zimmer et al. .......... 514/431 |
| 2005/0277645 A1 | | 12/2005 | Moree et al. |
| 2006/0252818 A1 | | 11/2006 | Kiankarimi et al. |

FOREIGN PATENT DOCUMENTS

| | | |
|---|---|---|
| EP | 0303961 A2 | 2/1989 |
| ES | 2131020 A1 | 7/1999 |
| WO | WO9413620 A1 | 6/1994 |
| WO | WO03104216 A1 | 12/2003 |

OTHER PUBLICATIONS

Boye, S., et al., "N, N-Disubstituted Aminomethyl Benzofuran Derivatives: Synthesis and Preliminary Binding Evaluation," Bioorganic & Medicinal Chemistry, 7(2):335-341, Feb. 1999.

* cited by examiner

*Primary Examiner*—Rita Desai
*Assistant Examiner*—John Mabry
(74) *Attorney, Agent, or Firm*—Joseph-Stephen M. DaRe

(57) ABSTRACT

Monoamine re-uptake inhibitors and more specifically serotonin and noradrenaline re-uptake inhibitors are disclosed that have utility in the treatment of disorders of the central or peripheral nervous system in both men and women. The compounds of this invention have the structure:

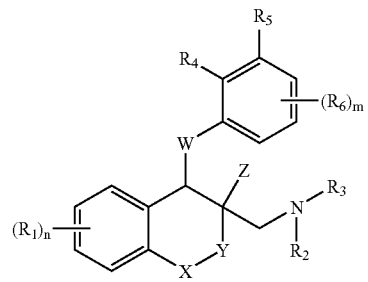

wherein $R_1$, $R_2$, $R_3$, $R_4$, $R_5$, $R_6$, m, n, W, X, Y, and Z are as defined herein, including stereoisomers, prodrugs and pharmaceutically acceptable salts, esters and solvates thereof. Also disclosed are compositions containing a compound of this invention in combination with a pharmaceutically acceptable carrier, as well as methods relating to the use thereof for inhibiting monoamine re-uptake in a subject in need thereof.

15 Claims, No Drawings

MONOAMINE RE-UPTAKE INHIBITORS AND METHODS RELATING THERETO

CROSS-REFERENCE TO RELATED APPLICATIONS

This application claims the benefit of U.S. Provisional Patent Application No. 60/687,940 filed Jun. 7, 2005 and U.S. Provisional Patent Application No. 60/752,259 filed Dec. 19, 2005, which applications are incorporated herein by reference in their entirety.

FIELD OF THE INVENTION

This invention relates generally to monoamine re-uptake inhibitors and more specifically to serotonin and noradrenaline re-uptake inhibitors, and to methods of treating disorders by administration of such inhibitors to a warm-blooded animal in need thereof.

BACKGROUND OF THE INVENTION

Decreased concentrations of monoamine neurotransmitters, such as serotonin (also known as 5-hydroxytryptamine or 5-HT), noradrenaline (norepinephrine), and dopamine, are implicated in a number of disorders of the central or peripheral nervous system. These disorders include depression, eating disorders, schizophrenia, inflammatory bowel disorders, pain, addiction disorders, urinary incontinence, dementia, Alzheimer's, memory loss, Parkinsonism, anxiety, attention-deficit disorder, social phobia, obsessive compulsive disorder, substance abuse and withdrawal, cognitive disorders, fibromyalgia and sleep disorders. These neurotransmitters travel from the terminal of a neuron across a small gap (i.e., the synaptic cleft) and bind to receptor molecules on the surface of a second neuron. This binding elicits intracellular changes that initiate or activate a response or change in the postsynaptic neuron. Inactivation occurs primarily by transport (i.e., reuptake) of the neurotransmitter back into the presynaptic neuron. Enhancing the amount of one or more of these monoamines has been shown to have utility in the treatment of disorders such as depression, anxiety, neuropathic pain, fibromyalgia, urinary incontinence and attention deficit hyperactivity disorder (ADHD). One advantageous method to increase the amount of a monoamine or monoamines is by administering a re-uptake inhibitor which has a particular selectivity/affinity to one or more monoamine transporters.

Selective serotonin re-uptake inhibitors (SSRIs) function by inhibiting the reuptake of serotonin by afferent neurons. SSRIs well known in the art include sertraline (Zoloft®), fluoxetine (Prozac®) and paroxetine (Paxil®). Selective noradrenaline (or norepinephrine) re-uptake inhibitors function by increasing noradrenaline levels and include drugs known in the art including reboxetine (Edronax®), atomoxetine (Strattera®), and buprorion (Wellbutrin®). Dual serotonin-noradrenaline re-uptake inhibitors (SNRIs) which inhibit the reuptake of both serotonin and norepinephrine include venlafaxine (Effexor®), duloxetine (Cymbalta®), milnacipran and imipramine (Tofranil®).

While significant strides have been made in this field, there remains a need in the art for effective small molecule monoamine re-uptake inhibitors. These inhibitors may advantageously possess characteristics such as enhanced selectivity toward one or more monoamine transporters, enhanced pharmacokinetic properties (such as half-life, bioavailability, and minimal interaction with liver enzymes such as the cytochrome P450 family), and/or enhanced potency. There is also a need for pharmaceutical compositions containing such monoamine re-uptake inhibitors, as well as methods relating to the use thereof to treat, for example, conditions caused by low concentrations of a monoamine or monoamines. The present invention fulfills these needs, and provides other related advantages.

BRIEF SUMMARY OF THE INVENTION

In brief, this invention is generally directed to monoamine re-uptake inhibitors, in particular, serotonin and/or noradrenaline reuptake inhibitors, as well as to methods for their preparation and use, and to pharmaceutical compositions containing the same. More specifically, the monoamine re-uptake inhibitors of this invention are compounds having the following general structure (I):

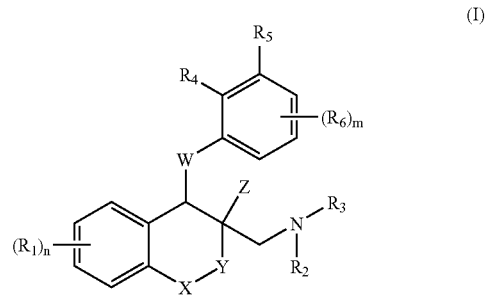

(I)

including stereoisomers, prodrugs and pharmaceutically acceptable salts, esters and solvates thereof, wherein $R_1$, $R_2$, $R_3$, $R_4$, $R_5$, $R_6$, m, n, W, X, Y, and Z are as defined below.

The monoamine reuptake inhibitors of this invention may have utility over a wide range of therapeutic applications, and may be used to treat a variety of disorders of the central or peripheral nervous system in both men and women, as well as a mammal in general (also referred to herein as a "subject"). For example, such conditions include, but are not limited to, depression, eating disorders, schizophrenia, inflammatory bowel disorders, pain, addiction disorders, urinary incontinence, dementia, Alzheimer's, memory loss, Parkinsonism, anxiety, attention-deficit disorder, social phobia, obsessive compulsive disorder, substance abuse and withdrawal, cognitive disorders, fibromyalgia and sleep disorders. Conditions of particular interest which may be treated by administration of compounds of structure (I) include depression, anxiety, neuropathic pain, fibromyalgia, urinary incontinence and attention deficit hyperactivity disorder (ADHD). The compounds may also be useful in combination with antipsychotic agents for the treatment of schizophrenia, as well as in combination with dopaminergic agents for use in Parkinson's disease.

The methods of this invention include administering an effective amount of a monoamine re-uptake inhibitor, preferably in the form of a pharmaceutical composition, to a mammal in need thereof. Thus, in still a further embodiment, pharmaceutical compositions are disclosed containing one or more monoamine re-uptake inhibitors of this invention in combination with a pharmaceutically acceptable carrier and/or diluent.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION OF THE INVENTION

As mentioned above, the present invention is directed generally to compounds useful as monoamine reuptake inhibitors. The compounds of this invention have the following structure (I):

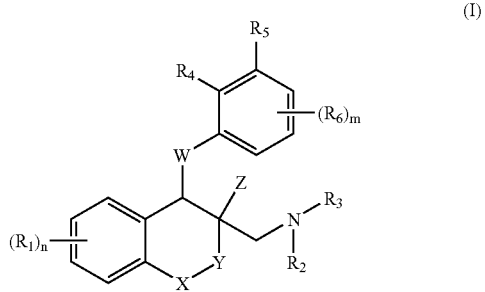

and stereoisomers, prodrugs and pharmaceutically acceptable salts, esters and solvates thereof, wherein:

W is —CH$_2$—, O or S;

X—Y is —CH$_2$—, —CH$_2$CH$_2$—, —OCH$_2$—, or —SCH$_2$—;

Z is F, OH, lower alkoxy, or substituted lower alkoxy;

R$_1$ at each occurrence is independently halo, CN, CF$_3$, OH, lower alkyl, lower alkoxy, or lower thioalkyl;

R$_2$, R$_3$ are independently H, lower alkyl, or substituted lower alkyl;

or R$_2$ and the nitrogen to which it is attached taken together with Z and the carbon to which it is attached form a 5-7 member heterocycle where the heterocycle is substituted with 0-4 R$_7$;

R$_4$, R$_5$ are independently H, halo, CN, CF$_3$, OH, lower alkyl, substituted lower alkyl, lower alkoxy, substituted lower alkoxy, lower thioalkyl, or substituted lower thioalkyl;

or R$_4$ and the carbon to which it is attached taken together with R$_5$ and the carbon to which it is attached form a 5-6 member carbocycle or a 5-6 member heterocycle where the carbocycle or heterocycle is substituted with 0-4 R$_7$;

R$_6$, R$_7$ are at each occurrence independently H, halo, CN, CF$_3$, OH, lower alkyl, substituted lower alkyl, lower alkoxy, or lower thioalkyl;

m is 0, 1, 2, or 3; and n is 0, 1, 2 or 3.

As used herein, the above terms have the following meaning:

"Alkyl" means a straight chain or branched, noncyclic or cyclic, unsaturated or saturated aliphatic hydrocarbon containing from 1 to 10 carbon atoms, while the term "lower alkyl" has the same meaning as alkyl but contains from 1 to 4 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —CH$_2$-cyclopropyl, —CH$_2$-cyclobutyl, —CH$_2$-cyclopentyl, —CH$_2$-cyclohexyl, and the like; while unsaturated cyclic alkyls include cyclopentenyl and cyclohexenyl, and the like. Cyclic alkyls include di- and poly-homocyclic rings such as decalin and adamantyl. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like.

"Aryl" means an aromatic carbocyclic moiety such as phenyl or naphthyl.

"5-6 Member carbocycle" means a ring composed of 5 or 6 carbon atoms, either saturated, unsaturated or aromatic.

"Heteroaryl" means an aromatic heterocycle ring of 5- to 10-members and having at least one heteroatom selected from nitrogen, oxygen and sulfur, and containing at least 1 carbon atom, including both mono- and bicyclic ring systems. Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heterocycle" (also referred to herein as a "heterocycle ring") means a 5- to 7-membered monocyclic, or 7- to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperizinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Halogen" or "halo" means fluoro, chloro, bromo and iodo.

"Alkoxy" means an alkyl moiety attached through an oxygen bridge (i.e., —O-alkyl), such as —O-methyl, —O-ethyl, and the like.

"Thioalkyl" means an alkyl moiety attached through a sulfur bridge (i.e., —S-alkyl) such as —S-methyl, —S-ethyl, and the like.

Lastly, the term "substituted" as used herein means any of the above groups (i.e., alkyl, carbocycle, aryl, or heterocycle) wherein at least one hydrogen atom is replaced with a substituent. In the case of an oxo substituent ("=O") two hydrogen atoms are replaced. "Substituents" within the context of this invention include halogen, hydroxy, oxo, cyano, nitro, amino, alkylamino, dialkylamino, alkyl, alkoxy, thioalkyl, haloalkyl, hydroxyalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, —NR$_a$R$_b$, —NR$_a$C(=O)R$_b$, —NR$_a$C(=O)NR$_a$R$_b$, —NR$_a$C(=O)OR$_b$, —NR$_a$SO$_2$R$_b$, —OR$_a$, —C(=O)R$_a$, —C(=O)OR$_a$, —C(=O)NR$_a$R$_b$, —OC(=O)NR$_a$R$_b$, —SH, —SR$_a$, —SOR$_a$, —S(=O)$_2$R$_a$, —OS(=O)$_2$R$_a$, —S(=O)$_2$OR$_a$, wherein R$_a$ and R$_b$ are the same or different and independently hydrogen, alkyl, haloalkyl, substituted alkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl.

In an embodiment of the present invention, —X—Y— of structure (I) is —CH$_2$— and —CH$_2$CH$_2$—, as shown in structures (II) and (III), respectively.

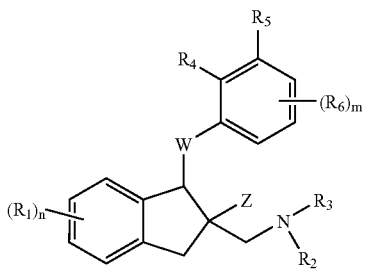
(II)

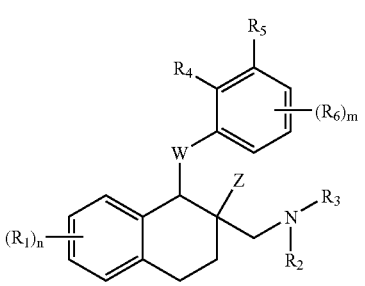
(III)

In another embodiment, —X—Y— of structure (I) is —OCH$_2$— and —SCH$_2$—, as shown in structures (IV) and (V), respectively.

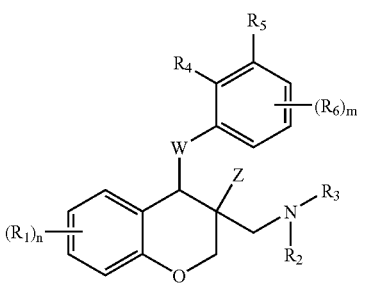
(IV)

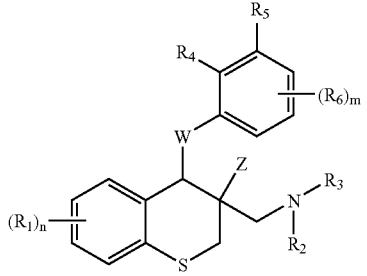
(V)

In an embodiment of the present invention, W of structure (I) is —CH$_2$—, O and S, as shown in structures (VI), (VII), and (VIII), respectively.

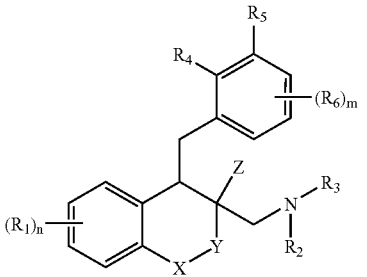
(VI)

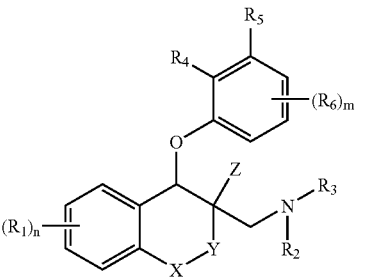
(VII)

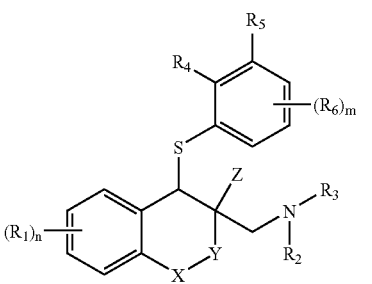
(VIII)

In an additional embodiment, Z of structure (I) is F, OH and lower alkoxy as shown in structures (IX), (X), and (XI), respectively.

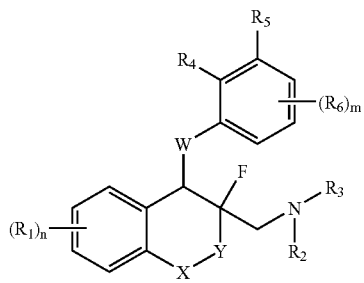
(IX)

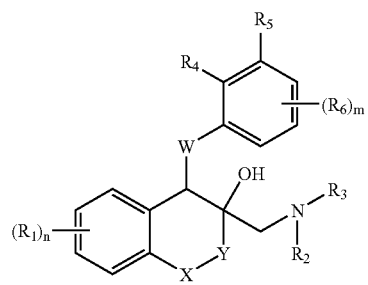
(X)

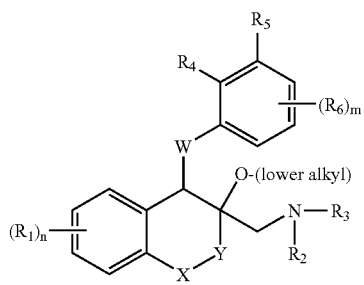
(XI)

In another embodiment, $R_4$ and $R_5$ of structure (I) taken together with the carbons to which they are attached form a ring such as thiophene creating a benzothiophen-7-yl group as shown in structure (XII). In an alternate embodiment, $R_4$ and $R_5$ do not cyclize and are represented as methyl and fluoro respectively, as shown in structure (XIII).

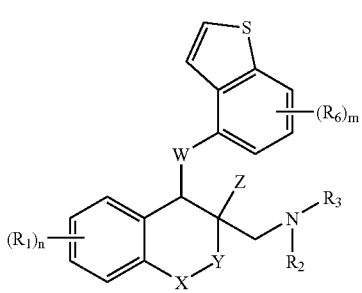
(XII)

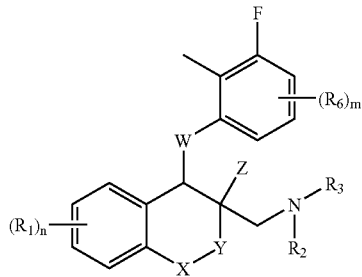
(XIII)

In another embodiment, the compounds of the present invention exist as a mix of 4 diastereomers as shown in Structure (XIV) when no stereochemistry is shown. A structure such as structure (XV) which shows stereochemistry and includes the term "racemic" is intended to encompass the 2 enantiomers where Z and W are either both pointing into or out of the plane (a 'cis' configuration).

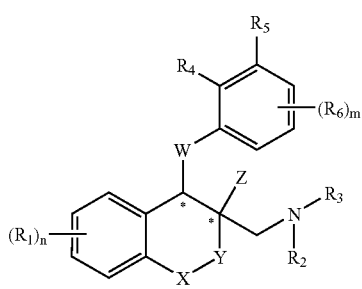
(XIV)

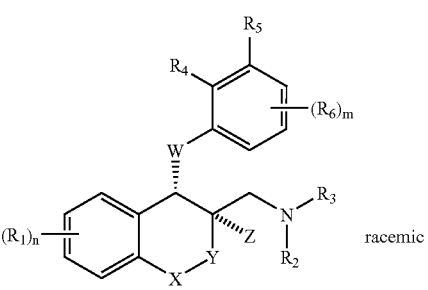
(XV)

In another embodiment, Structure (XVI) is labeled "racemic" and is meant to include the 2 enantiomers where Z and W are 'trans' as shown in structures (XVII) and (XVIII).

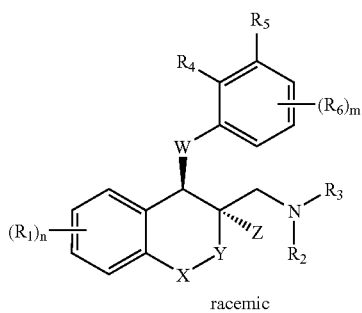
(XVI)

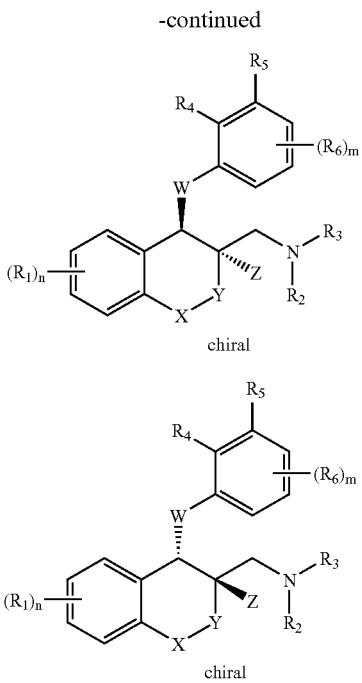

(XVII)

(XVIII)

chiral

In another embodiment X—Y is —CH$_2$—.
In an embodiment X—Y is —CH$_2$CH$_2$—.
In an embodiment X—Y is —OCH$_2$—.
In another embodiment X—Y is —SCH$_2$—.
In an embodiment W is —CH$_2$—.
In an embodiment W is O.
In another embodiment W is S.
In another embodiment X—Y is —CH$_2$— and W is O.
In an embodiment X—Y is —CH$_2$—, W is O, and R$_3$ is lower alkyl.
In another embodiment X—Y is —CH$_2$—, W is O, R$_3$ is lower alkyl and Z is OH.
In an embodiment X—Y is —CH$_2$—, W is O, R$_3$ is lower alkyl and Z is F.
In another embodiment X—Y is —CH$_2$—, W is O, R$_3$ is lower alkyl and Z is lower alkoxy.
In another embodiment R$_4$ is halo or lower alkyl.
In an embodiment R$_5$ or R$_6$ is halo.
In another embodiment R$_4$ is halo or lower alkyl and R$_5$ or R$_6$ is halo.
In an embodiment X—Y is —OCH$_2$—, W is O, and R$_3$ is lower alkyl.
In another embodiment R$_2$ is H.
In another embodiment R$_2$ is H and R$_3$ is lower alkyl.
In another embodiment R$_2$ is H, R$_3$ is lower alkyl, X—Y is —CH$_2$—, W is O, and Z is OH.
In another embodiment R$_2$ is H, R$_3$ is lower alkyl, X—Y is —CH$_2$—, W is O, and Z is F.
In another embodiment R$_2$ is H, R$_3$ is lower alkyl, X—Y is —OCH$_2$—, W is O, and Z is OH.
In another embodiment R$_2$ is H, R$_3$ is lower alkyl, X—Y is —OCH$_2$—, W is O, and Z is F.
In another embodiment, the term 'substituted' as used with substituted lower alkyl, substituted lower alkoxy and substituted lower thioalkyl means replacing a hydrogen from the lower alkyl, lower alkoxy or lower thioalkyl with a substituent selected from halo, alkoxy, amino, alkylamino, dialkylamino, OH, or CN.

Particular individual compounds of the present invention include:

(1R,2S and 1S,2R)-2-Methylaminomethyl-1-o-tolyloxy-indan-2-ol (Example 1-1);
(1R,2S)-2-Methylaminomethyl-1-o-tolyloxy-indan-2-ol (1-2);
(1S,2R)-2-Methylaminomethyl-1-o-tolyloxy-indan-2-ol (1-3);
(1R,2S and 1S,2R)-2-Methylaminomethyl-1-phenoxy-indan-2-ol (1-4);
(1R,2S and 1S,2R)-2-Methylaminomethyl-1-(naphthalen-1-yloxy)-indan-2-ol (1-5);
(1R,2S and 1S,2R)-2-Ethylaminomethyl-1-o-tolyloxy-indan-2-ol (1-6);
(1R,2S and 1S,2R)-1-(2-Ethyl-phenoxy)-2-methylaminomethyl-indan-2-ol (1-7)
(1R,2S and 1S,2R)-1-(2,3-Dimethyl-phenoxy)-2-methylaminomethyl-indan-2-ol (1-8);
(1R,2S and 1S,2R)-1-(2,4-Dimethyl-phenoxy)-2-methylaminomethyl-indan-2-ol (1-9);
(1R,2S and 1S,2R)-1-(2-Methoxy-phenoxy)-2-methylaminomethyl-indan-2-ol (1-10);
(1S,2R)-1-(2-Methoxy-phenoxy)-2-methylaminomethyl-indan-2-ol (1-11);
(1R,2S and 1S,2R)-1-(2-Chloro-phenoxy)-2-methylaminomethyl-indan-2-ol (1-12);
(1S,2R)-1-(2-Chloro-phenoxy)-2-methylaminomethyl-indan-2-ol (1-13);
(1R,2S and 1S,2R)-2-Dimethylaminomethyl-1-o-tolyloxy-indan-2-ol (1-14);
(1R,2S and 1S,2R)-1-(2-Bromo-phenoxy)-2-methylaminomethyl-indan-2-ol (1-15);
(1R,2S and 1S,2R)-2-Methylaminomethyl-1-(2-methyl-benzo[b]thiophen-7-yloxy)-indan-2-ol (1-16);
(1R,2S and 1S,2R)-1-(Benzo[b]thiophen-4-yloxy)-2-methylaminomethyl-indan-2-ol (1-17);
(1R,2S)-1-(Benzo[b]thiophen-4-yloxy)-2-methylaminomethyl-indan-2-ol (1-18);
(1S,2R)-1-(Benzo[b]thiophen-4-yloxy)-2-methylaminomethyl-indan-2-ol (1-19);
(1R,2S and 1S,2R)-1-(Benzo[b]thiophen-7-yloxy)-2-methylaminomethyl-indan-2-ol (1-20);
(1R,2S and 1S,2R)-1-(2,2-Dimethyl-benzo[1,3]dioxol-4-yloxy)-2-methylaminomethyl-indan-2-ol (1-21);
(1R,2S and 1S,2R)-1-(4-Fluoro-2-methyl-phenoxy)-2-methylaminomethyl-indan-2-ol (1-22);
(1R,2S)-1-(4-Fluoro-2-methyl-phenoxy)-2-methylaminomethyl-indan-2-ol (1-23);
(1S,2R)-1-(4-Fluoro-2-methyl-phenoxy)-2-methylaminomethyl-indan-2-ol (1-24);
(1R,2S and 1S,2R)-1-(2,5-Dimethyl-phenoxy)-2-methylaminomethyl-indan-2-ol (1-25);
(1R,2S and 1S,2R)-2-Methylaminomethyl-1-o-tolylsulfanyl-indan-2-ol (1-26);
(1R,2S)-1-(2,4-Dimethyl-phenoxy)-2-methylaminomethyl-indan-2-ol (1-27);
(1R,2S)-1-(2,2-Dimethyl-benzo[1,3]dioxol-4-yloxy)-2-methylaminomethyl-indan-2-ol (1-28);
(1S,2R)-1-(2,4-Dimethyl-phenoxy)-2-methylaminomethyl-indan-2-ol (1-29);
(1S,2R)-1-(2,2-Dimethyl-benzo[1,3]dioxol-4-yloxy)-2-methylaminomethyl-indan-2-ol (1-30);
(1S,2R)-1-(2-Methyl-phenylsulfanyl)-2-methylaminomethyl-indan-2-ol (1-31);
(1S,2R)-1-(2,3-Dimethyl-phenoxy)-2-methylaminomethyl-indan-2-ol (1-32);

(1R,2S)-1-(2-Methyl-phenylsulfanyl)-2-methylaminomethyl-indan-2-ol (1-33);

(1S,2R)-1-(2-Ethyl-phenoxy)-2-methylaminomethyl-indan-2-ol (1-34);

(1R,2S)-1-(2-Ethyl-phenoxy)-2-methylaminomethyl-indan-2-ol (1-35);

(1R,2S)-1-(2,3-Dimethyl-phenoxy)-2-methylaminomethyl-indan-2-ol (1-36);

(1R,2S and 1S,2R)-2-Methylaminomethyl-1-(2-methylsulfanyl-phenoxy)-indan-2-ol (1-37);

(1R,2S and 1S,2R)-1-(2-Fluoro-phenyloxy)-2-methylaminomethyl-indan-2-ol (1-38);

(1R,2S)-1-(3-Fluoro-2-methyl-phenyloxy)-2-methylaminomethyl-indan-2-ol (1-39);

(1R,2S)-2-Methylaminomethyl-1-(2-methylsulfanyl-phenoxy)-indan-2-ol (1-40);

(1S,2R)-2-Methylaminomethyl-1-(2-methylsulfanyl-phenoxy)-indan-2-ol (1-41);

(1R,2S and 1S,2R)-1-(5-Fluoro-2-methyl-phenyloxy)-2-methylaminomethyl-indan-2-ol (1-42);

(1R,2S)-1-(2-Fluoro-phenyloxy)-2-methylaminomethyl-indan-2-ol (1-43);

(1S,2R)-1-(2-Fluoro-phenyloxy)-2-methylaminomethyl-indan-2-ol (1-44);

(1R,2S)-1-(5-Fluoro-2-methyl-phenyloxy)-2-methylaminomethyl-indan-2-ol (1-45);

(1S,2R)-1-(5-Fluoro-2-methyl-phenyloxy)-2-methylaminomethyl-indan-2-ol (1-46);

(1R,2S and 1S,2R)-1-(2-Fluoro-6-methyl-phenyloxy)-2-methylaminomethyl-indan-2-ol (1-47);

(1S,2R)-1-(2-Fluoro-6-methyl-phenyloxy)-2-methylaminomethyl-indan-2-ol (1-48);

(1R,2S)-1-(2-Fluoro-6-methyl-phenyloxy)-2-methylaminomethyl-indan-2-ol (1-49);

(1S,2R)-2-[(2-Hydroxyethylamino)-methyl]-1-o-tolyloxy-indan-2-ol (1-50);

(1R,2S and 1S,2R)-2-Aminomethyl-1-o-tolyloxy-indan-2-ol (2-1);

(1R,2S)-2-Aminomethyl-1-o-tolyloxy-indan-2-ol (2-3);

(1S,2R)-2-Aminomethyl-1-o-tolyloxy-indan-2-ol (2-4);

(1R,2S and 1S,2R)-2-Aminomethyl-1-(2-chloro-phenoxy)-indan-2-ol (2-5);

(1S,2R)-2-Aminomethyl-1-(2-chloro-phenoxy)-indan-2-ol (2-6);

(1R,2S)-2-Aminomethyl-1-(2-chloro-phenoxy)-indan-2-ol (2-7);

(1R,2S and 1S,2R)-2-Aminomethyl-1-(4-fluoro-2-methyl-phenyloxy)-indan-2-ol (2-8);

(1R,2S and 1S,2R)-2-Aminomethyl-1-(3-fluoro-2-methyl-phenyloxy)-indan-2-ol (2-9);

(1R,2S)-2-Aminomethyl-1-(3-fluoro-2-methyl-phenyloxy)-indan-2-ol (2-10);

(1S,2R)-2-Aminomethyl-1-(3-fluoro-2-methyl-phenyloxy)-indan-2-ol (2-11);

(1R,2S and 1S,2R)-2-Aminomethyl-1-(2-fluoro-phenoxy)-indan-2-ol (2-12);

(1R,2S)-2-Aminomethyl-1-(2-fluoro-phenoxy)-indan-2-ol (2-13);

(1S,2R)-2-Aminomethyl-1-(2-fluoro-phenoxy)-indan-2-ol (2-14);

(1S,2R)-2-Aminomethyl-1-(4-fluoro-2-methyl-phenyloxy)-indan-2-ol (2-15);

(1R,2S)-2-Aminomethyl-1-(4-fluoro-2-methyl-phenyloxy)-indan-2-ol (2-16);

(1R,2S and 1S,2R)-2-Aminomethyl-1-(2-fluoro-6-methyl-phenyloxy)-indan-2-ol (2-17);

(1S,2R)-2-Aminomethyl-1-(2-fluoro-6-methyl-phenyloxy)-indan-2-ol (2-18);

(1R,2S and 1S,2R)-2-Aminomethyl-1-(5-fluoro-2-methyl-phenyloxy)-indan-2-ol (2-19);

(1R,2S)-2-Aminomethyl-1-(2-fluoro-6-methyl-phenyloxy)-indan-2-ol (2-20);

(1S,2R)-2-Aminomethyl-1-(5-fluoro-2-methyl-phenyloxy)-indan-2-ol (2-21);

(1R,2S)-2-Aminomethyl-1-(5-fluoro-2-methyl-phenyloxy)-indan-2-ol (2-22);

(1R,2S and 1S,2R)-2-Aminomethyl-1-(2,4-di-fluoro-2-phenyloxy)-indan-2-ol (2-23);

(1R,2S and 1S,2R)-2-Methylaminomethyl-1-(2-methyl-benzyl)-indan-2-ol (3-1)

(1S,2R)-2-Methylaminomethyl-1-(naphthalen-1-yloxy)-indan-2-ol (4-1);

(1R,2S and 1S,2R)-1-(4-Hydroxy-2-methyl-phenoxy)-2-methylaminomethyl-indan-2-ol (6-1);

(1R,2S)-1-(4-Hydroxy-2-methyl-phenoxy)-2-methylaminomethyl-indan-2-ol (6-2);

(1S,2R)-1-(4-Hydroxy-2-methyl-phenoxy)-2-methylaminomethyl-indan-2-ol (6-3);

(1R,2S and 1S,2R)-1-(3-Hydroxy-2-methyl-phenoxy)-2-methylaminomethyl-indan-2-ol (6-4);

(1R,2S)-1-(3-Hydroxy-2-methyl-phenoxy)-2-methylaminomethyl-indan-2-ol (6-5);

(1S,2R)-1-(3-Hydroxy-2-methyl-phenoxy)-2-methylaminomethyl-indan-2-ol (6-6);

(3S,4S and 3R,4R)-3-Methylaminomethyl-4-o-tolyloxy-chroman-3-ol (7-1);

(3R,4R)-3-Methylaminomethyl-4-o-tolyloxy-chroman-3-ol (7-2);

(3S,4S)-3-Methylaminomethyl-4-o-tolyloxy-chroman-3-ol (7-3);

(3S,4S and 3R,4R)-4-(2-Chloro-phenoxy)-3-methylaminomethyl-chroman-3-ol (7-4);

(3R,4R)-4-(2-Chloro-phenoxy)-3-methylaminomethyl-chroman-3-ol (7-5);

(3S,4S)-4-(2-Chloro-phenoxy)-3-methylaminomethyl-chroman-3-ol (7-6);

(3S,4S and 3R,4R)-4-(2,3-Dimethyl-phenoxy)-3-methylaminomethyl-chroman-3-ol (7-7);

(3S,4S)-4-(2,3-Dimethyl-phenoxy)-3-methylaminomethyl-chroman-3-ol (7-8);

(3R,4R)-4-(2,3-Dimethyl-phenoxy)-3-methylaminomethyl-chroman-3-ol (7-9);

(3S,4S and 3R,4R)-4-(2,4-Dimethyl-phenoxy)-3-methylaminomethyl-chroman-3-ol (7-10);

(3S,4S and 3R,4R)-4-(4-Fluoro-2-methyl-phenoxy)-3-methylaminomethyl-chroman-3-ol (7-11);

(3S,4S and 3R,4R)-4-(3-Fluoro-2-methyl-phenoxy)-3-methylaminomethyl-chroman-3-ol (7-12);

(3R,4R)-4-(2,4-Dimethyl-phenoxy)-3-methylaminomethyl-chroman-3-ol (7-13);

(3S,4S)-4-(2,4-Dimethyl-phenoxy)-3-methylaminomethyl-chroman-3-ol (7-14);

(3R,4R)-4-(4-Fluoro-2-methyl-phenoxy)-3-methylaminomethyl-chroman-3-ol (7-15);

(3S,4S)-4-(4-Fluoro-2-methyl-phenoxy)-3-methylaminomethyl-chroman-3-ol (7-16);

(3S,4S and 3R,4R)-4-(5-Fluoro-2-methyl-phenoxy)-3-methylaminomethyl-chroman-3-ol (7-17);

(3S,4S and 3R,4R)-4-(4-Hydroxy-2-methyl-phenoxy)-3-methylaminomethyl-chroman-3-ol (7-18);

(3R,4R)-4-(4-Hydroxy-2-methyl-phenoxy)-3-methylaminomethyl-chroman-3-ol (7-19);

(3S,4S)-4-(4-Hydroxy-2-methyl-phenoxy)-3-methylaminomethyl-chroman-3-ol (7-20);
(3S,4S and 3R,4R)-4-(4-Bromo-2-methyl-phenoxy)-3-methylaminomethyl-chroman-3-ol (7-21);
(3S,4S and 3R,4R)-4-(2-Ethyl-phenoxy)-3-methylaminomethyl-chroman-3-ol (7-22);
(3S,4S and 3R,4R)-4-(2-Methoxy-phenoxy)-3-methylaminomethyl-chroman-3-ol (7-23);
(3R,4R)-4-(4-Bromo-2-methyl-phenoxy)-3-methylaminomethyl-chroman-3-ol (7-24);
(3S,4S)-4-(4-Bromo-2-methyl-phenoxy)-3-methylaminomethyl-chroman-3-ol (7-25);
(3S,4S and 3R,4R)-3-Aminomethyl-4-o-tolyloxy-chroman-3-ol (8-1);
(3S,4S)-3-Aminomethyl-4-o-tolyloxy-chroman-3-ol (8-2);
(3R,4R)-3-Aminomethyl-4-o-tolyloxy-chroman-3-ol (8-3);
(3S,4S and 3R,4R)-3-Aminomethyl-4-(2-chloro-phenoxy)-chroman-3-ol (8-4);
(3S,4S and 3R,4R)-3-Aminomethyl-4-(2,4-dimethyl-phenoxy)-chroman-3-ol (8-5);
(3S,4S and 3R,4R)-3-Aminomethyl-4-(4-fluoro-2-methyl-phenoxy)-chroman-3-ol (8-6);
(3R,4R)-3-Aminomethyl-4-(2-chloro-phenoxy)-chroman-3-ol (8-7);
(3S,4S)-3-Aminomethyl-4-(2-chloro-phenoxy)-chroman-3-ol (8-8);
(3R,4R)-3-Aminomethyl-4-(2,4-dimethyl-phenoxy)-chroman-3-ol (8-9);
(3S,4S)-3-Aminomethyl-4-(2,4-dimethyl-phenoxy)-chroman-3-ol (8-10);
(3R,4R)-3-Aminomethyl-4-(4-fluoro-2-methyl-phenoxy)-chroman-3-ol (8-11);
(3S,4S)-3-Aminomethyl-4-(4-fluoro-2-methyl-phenoxy)-chroman-3-ol (8-12);
(1S,2R)-1-(3-Fluoro-2-methyl-phenoxy)-2-methylaminomethyl-indan-2-ol (12-1);
(1R,2S and 1S,2R)-1-(2-Chloro-4-hydroxy-phenoxy)-2-methylaminomethyl-indan-2-ol (13-1);
(1R,2S)-1-(2-Chloro-4-hydroxy-phenoxy)-2-methylaminomethyl-indan-2-ol (13-2);
(1S,2R)-1-(2-Chloro-4-hydroxy-phenoxy)-2-methylaminomethyl-indan-2-ol (13-3);
(1R,2S and 1S,2R)-2-Methylaminomethyl-1-o-tolyloxy-1,2,3,4-tetrahydro-naphthalen-2-ol (14-1);
(1S,2R)-2-Methylaminomethyl-1-o-tolyloxy-1,2,3,4-tetrahydro-naphthalen-2-ol (14-2);
(1R,2S)-2-Methylaminomethyl-1-o-tolyloxy-1,2,3,4-tetrahydro-naphthalen-2-ol (14-3);
(1S,2S and 1R,2R)-2-Methylaminomethyl-1-o-tolyloxy-indan-2-ol (15-1);
(1R,2S and 1S,2R)-5-Methoxy-2-methylaminomethyl-1-o-tolyloxy-indan-2-ol (16-1);
(1S,2R)-5-Methoxy-2-methylaminomethyl-1-o-tolyloxy-indan-2-ol (16-2);
(1R,2S)-5-Methoxy-2-methylaminomethyl-1-o-tolyloxy-indan-2-ol (16-3);
(1R,2S and 1S,2R)-1-(2-Hydroxymethyl-phenoxy)-2-methylaminomethyl-indan-2-ol (17-1);
(1R,2S)-1-(2-Hydroxymethyl-phenoxy)-2-methylaminomethyl-indan-2-ol (17-2);
(1S,2R)-1-(2-Hydroxymethyl-phenoxy)-2-methylaminomethyl-indan-2-ol (17-3);
(1R,2S and 1S,2R)-5-Fluoro-2-methylaminomethyl-1-o-tolyloxy-indan-2-ol (20-1);
(1R,2S and 1S,2R)-6-Fluoro-2-methylaminomethyl-1-o-tolyloxy-indan-2-ol (20-2);
(1R,2S and 1S,2R)-6-Methoxy-2-methylaminomethyl-1-o-tolyloxy-indan-2-ol (20-3);
and ((1R,2S)-2-Methoxy-1-o-tolyloxy-indan-2-ylmethyl)-methyl-amine (21-1).

Other compounds of the invention include the following and include each of the 4 individual diastereomers and mixes of more than 1 diastereomer.

1-(2-Fluoro-phenoxy)-5-methyl-2-methylaminomethyl-indan-2-ol;
1-(2-Fluoro-phenoxy)-6-methyl-2-methylaminomethyl-indan-2-ol;
1-(2-Fluoro-phenoxy)-5-methoxy-2-methylaminomethyl-indan-2-ol;
1-(2-Fluoro-phenoxy)-6-methoxy-2-methylaminomethyl-indan-2-ol;
5-Fluoro-1-(2-fluoro-phenoxy)-2-methylaminomethyl-indan-2-ol;
6-Fluoro-1-(2-fluoro-phenoxy)-2-methylaminomethyl-indan-2-ol;
1-(2-Fluoro-phenoxy)-2-methylaminomethyl-indan-2,5-diol;
3-(2-Fluoro-phenoxy)-2-methylaminomethyl-indan-2,5-diol;
5-Methyl-2-methylaminomethyl-1-o-tolyloxy-indan-2-ol;
6-Methyl-2-methylaminomethyl-1-o-tolyloxy-indan-2-ol;
5-Methoxy-2-methylaminomethyl-1-o-tolyloxy-indan-2-ol;
6-Methoxy-2-methylaminomethyl-1-o-tolyloxy-indan-2-ol;
5-Fluoro-2-methylaminomethyl-1-o-tolyloxy-indan-2-ol;
6-Fluoro-2-methylaminomethyl-1-o-tolyloxy-indan-2-ol;
1-(3-Fluoro-2-methyl-phenoxy)-5-methyl-2-methylaminomethyl-indan-2-ol;
1-(3-Fluoro-2-methyl-phenoxy)-6-methyl-2-methylaminomethyl-indan-2-ol;
1-(3-Fluoro-2-methyl-phenoxy)-5-methoxy-2-methylaminomethyl-indan-2-ol;
1-(3-Fluoro-2-methyl-phenoxy)-6-methoxy-2-methylaminomethyl-indan-2-ol;
5-Fluoro-1-(3-fluoro-2-methyl-phenoxy)-2-methylaminomethyl-indan-2-ol;
6-Fluoro-1-(3-fluoro-2-methyl-phenoxy)-2-methylaminomethyl-indan-2-ol;
1-(3-Fluoro-2-methyl-phenoxy)-2-methylaminomethyl-indan-2,5-diol;
3-(3-Fluoro-2-methyl-phenoxy)-2-methylaminomethyl-indan-2,5-diol;
1-(4-Fluoro-2-methyl-phenoxy)-5-methyl-2-methylaminomethyl-indan-2-ol;
1-(4-Fluoro-2-methyl-phenoxy)-6-methyl-2-methylaminomethyl-indan-2-ol;
1-(4-Fluoro-2-methyl-phenoxy)-5-methoxy-2-methylaminomethyl-indan-2-ol;
1-(4-Fluoro-2-methyl-phenoxy)-6-methoxy-2-methylaminomethyl-indan-2-ol;
5-Fluoro-1-(4-fluoro-2-methyl-phenoxy)-2-methylaminomethyl-indan-2-ol;
6-Fluoro-1-(4-fluoro-2-methyl-phenoxy)-2-methylaminomethyl-indan-2-ol;
1-(4-Fluoro-2-methyl-phenoxy)-2-methylaminomethyl-indan-2,5-diol;
3-(4-Fluoro-2-methyl-phenoxy)-2-methylaminomethyl-indan-2,5-diol;
1-(3-Hydroxy-2-methyl-phenoxy)-5-methyl-2-methylaminomethyl-indan-2-ol;
1-(3-Hydroxy-2-methyl-phenoxy)-6-methyl-2-methylaminomethyl-indan-2-ol;
1-(3-Hydroxy-2-methyl-phenoxy)-5-methoxy-2-methylaminomethyl-indan-2-ol;

1-(3-Hydroxy-2-methyl-phenoxy)-6-methoxy-2-methylaminomethyl-indan-2-ol;
5-Fluoro-1-(3-hydroxy-2-methyl-phenoxy)-2-methylaminomethyl-indan-2-ol;
6-Fluoro-1-(3-hydroxy-2-methyl-phenoxy)-2-methylaminomethyl-indan-2-ol;
1-(4-Hydroxy-2-methyl-phenoxy)-5-methyl-2-methylaminomethyl-indan-2-ol;
1-(4-Hydroxy-2-methyl-phenoxy)-6-methyl-2-methylaminomethyl-indan-2-ol;
1-(4-Hydroxy-2-methyl-phenoxy)-5-methoxy-2-methylaminomethyl-indan-2-ol;
1-(4-Hydroxy-2-methyl-phenoxy)-6-methoxy-2-methylaminomethyl-indan-2-ol;
5-Fluoro-1-(4-hydroxy-2-methyl-phenoxy)-2-methylaminomethyl-indan-2-ol;
6-Fluoro-1-(4-hydroxy-2-methyl-phenoxy)-2-methylaminomethyl-indan-2-ol;
[2-Fluoro-1-(2-fluoro-phenoxy)-indan-2-ylmethyl]-methyl-amine;
[2-Fluoro-1-o-tolyloxy-indan-2-ylmethyl]-methyl-amine;
[2-Fluoro-1-(3-fluoro-2-methyl-phenoxy)-indan-2-ylmethyl]-methyl-amine;
[2-Fluoro-1-(4-fluoro-2-methyl-phenoxy)-indan-2-ylmethyl]-methyl-amine;
3-(2-Fluoro-2-methylaminomethyl-indan-1-yloxy)-2-methyl-phenol;
4-(2-Fluoro-2-methylaminomethyl-indan-1-yloxy)-3-methyl-phenol;
[2-Fluoro-1-(2-fluoro-phenoxy)-5-methyl-indan-2-ylmethyl]-methyl-amine;
[2-Fluoro-1-(2-fluoro-phenoxy)-6-methyl-indan-2-ylmethyl]-methyl-amine;
[2-Fluoro-1-(2-fluoro-phenoxy)-5-methoxy-indan-2-ylmethyl]-methyl-amine;
[2-Fluoro-1-(2-fluoro-phenoxy)-6-methoxy-indan-2-ylmethyl]-methyl-amine;
[2,5-Difluoro-1-(2-fluoro-phenoxy)-indan-2-ylmethyl]-methyl-amine;
[2,6-Difluoro-1-(2-fluoro-phenoxy)-indan-2-ylmethyl]-methyl-amine;
2-Fluoro-1-(2-fluoro-phenoxy)-2-methylaminomethyl-indan-5-ol;
2-Fluoro-3-(2-fluoro-phenoxy)-2-methylaminomethyl-indan-5-ol;
(2-Fluoro-5-methyl-1-o-tolyloxy-indan-2-ylmethyl)-methyl-amine;
(2-Fluoro-6-methyl-1-o-tolyloxy-indan-2-ylmethyl)-methyl-amine;
(2-Fluoro-5-methoxy-1-o-tolyloxy-indan-2-ylmethyl)-methyl-amine;
(2-Fluoro-6-methoxy-1-o-tolyloxy-indan-2-ylmethyl)-methyl-amine;
(2,5-Difluoro-1-o-tolyloxy-indan-2-ylmethyl)-methyl-amine;
(2,6-Difluoro-1-o-tolyloxy-indan-2-ylmethyl)-methyl-amine;
[2-Fluoro-1-(3-fluoro-2-methyl-phenoxy)-5-methyl-indan-2-ylmethyl]-methyl-amine;
[2-Fluoro-1-(3-fluoro-2-methyl-phenoxy)-6-methyl-indan-2-ylmethyl]-methyl-amine;
[2-Fluoro-1-(3-fluoro-2-methyl-phenoxy)-5-methoxy-indan-2-ylmethyl]-methyl-amine;
[2-Fluoro-1-(3-fluoro-2-methyl-phenoxy)-6-methoxy-indan-2-ylmethyl]-methyl-amine;
2-Fluoro-1-(3-fluoro-2-methyl-phenoxy)-2-methylaminomethyl-indan-5-ol;
2-Fluoro-3-(3-fluoro-2-methyl-phenoxy)-2-methylaminomethyl-indan-5-ol;
[2-Fluoro-1-(4-fluoro-2-methyl-phenoxy)-5-methyl-indan-2-ylmethyl]-methyl-amine;
[2-Fluoro-1-(4-fluoro-2-methyl-phenoxy)-6-methyl-indan-2-ylmethyl]-methyl-amine;
[2-Fluoro-1-(4-fluoro-2-methyl-phenoxy)-5-methoxy-indan-2-ylmethyl]-methyl-amine;
[2-Fluoro-1-(4-fluoro-2-methyl-phenoxy)-6-methoxy-indan-2-ylmethyl]-methyl-amine;
2-Fluoro-1-(4-fluoro-2-methyl-phenoxy)-2-methylaminomethyl-indan-5-ol;
2-Fluoro-3-(4-fluoro-2-methyl phenoxy)-2-methylaminomethyl-indan-5-ol;
3-(2-Fluoro-5-methyl-2-methylaminomethyl-indan-1-yloxy)-2-methyl-phenol;
3-(2-Fluoro-6-methyl-2-methylaminomethyl-indan-1-yloxy)-2-methyl-phenol;
3-(2-Fluoro-5-methoxy-2-methylaminomethyl-indan-1-yloxy)-2-methyl-phenol;
3-(2-Fluoro-6-methoxy-2-methylaminomethyl-indan-1-yloxy)-2-methyl-phenol;
3-(2,5-Difluoro-2-methylaminomethyl-indan-1-yloxy)-2-methyl-phenol;
3-(2,6-Difluoro-2-methylaminomethyl-indan-1-yloxy)-2-methyl-phenol;
4-(2-Fluoro-5-methyl-2-methylaminomethyl-indan-1-yloxy)-3-methyl-phenol;
4-(2-Fluoro-6-methyl-2-methylaminomethyl-indan-1-yloxy)-3-methyl-phenol;
4-(2-Fluoro-5-methoxy-2-methylaminomethyl-indan-1-yloxy)-3-methyl-phenol;
4-(2-Fluoro-6-methoxy-2-methylaminomethyl-indan-1-yloxy)-3-methyl-phenol;
4-(2,5-Difluoro-2-methylaminomethyl-indan-1-yloxy)-3-methyl-phenol; and
4-(2,6-Difluoro-2-methylaminomethyl-indan-1-yloxy)-3-methyl-phenol.

The compounds of the present invention may be prepared by known organic synthesis techniques, including the methods described in more detail in the Examples. In general, the compounds of structure (I) above may be made by the following reaction schemes, wherein all substituents are as defined above unless indicated otherwise.

Reaction Scheme 1

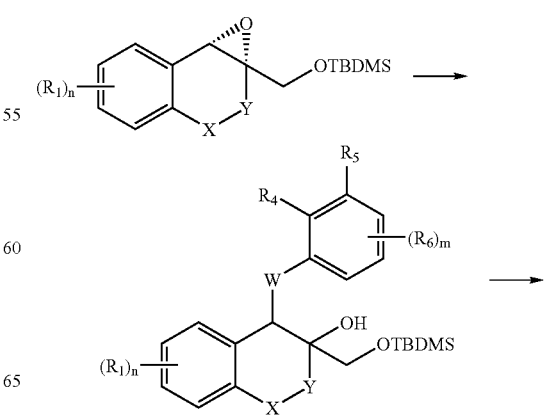

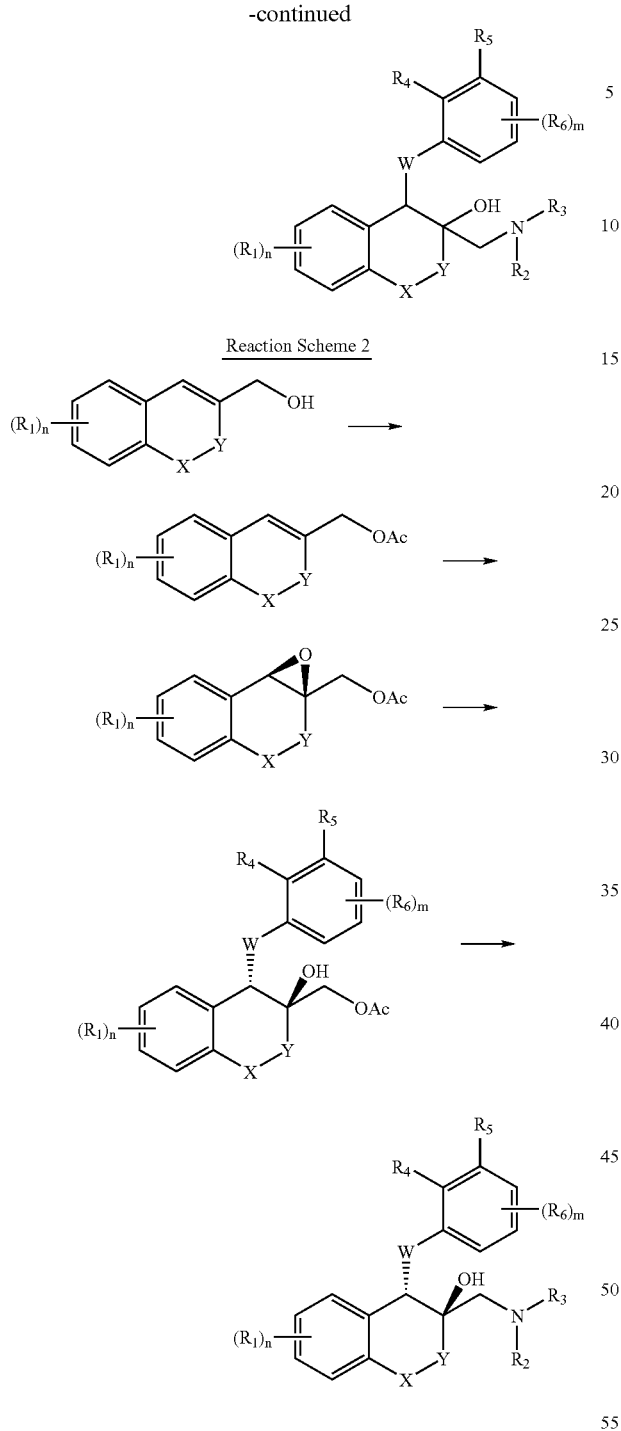

Reaction Scheme 2

The compounds are typically prepared by protection of a cyclic allylic alcohol, for example with acetate, epoxidation with agents such as peroxyacids to give the racemic epoxide followed by epoxide opening with the metal salt of a phenol (W=O). The trans product is then deprotected to the diol and the primary alcohol is selectively activated, for example as the mesylate. Closure to the epoxide under mildly basic conditions, followed by opening predominantly at the primary carbon with a primary or secondary amine gives the amino alcohol diastereomer with W and the OH trans to one another. Alternatively, a chiral epoxidation reagent can be used to generate predominantly one enantiomer of the cyclic epoxide that can then be converted with retention of configuration to the amino alcohol. Instead of a phenol, the initial epoxide can also be opened with the metal salt of a thiophenol or the metal salt of a carbanion, the product of the sequence being the compound where W=S and W=C, respectively.

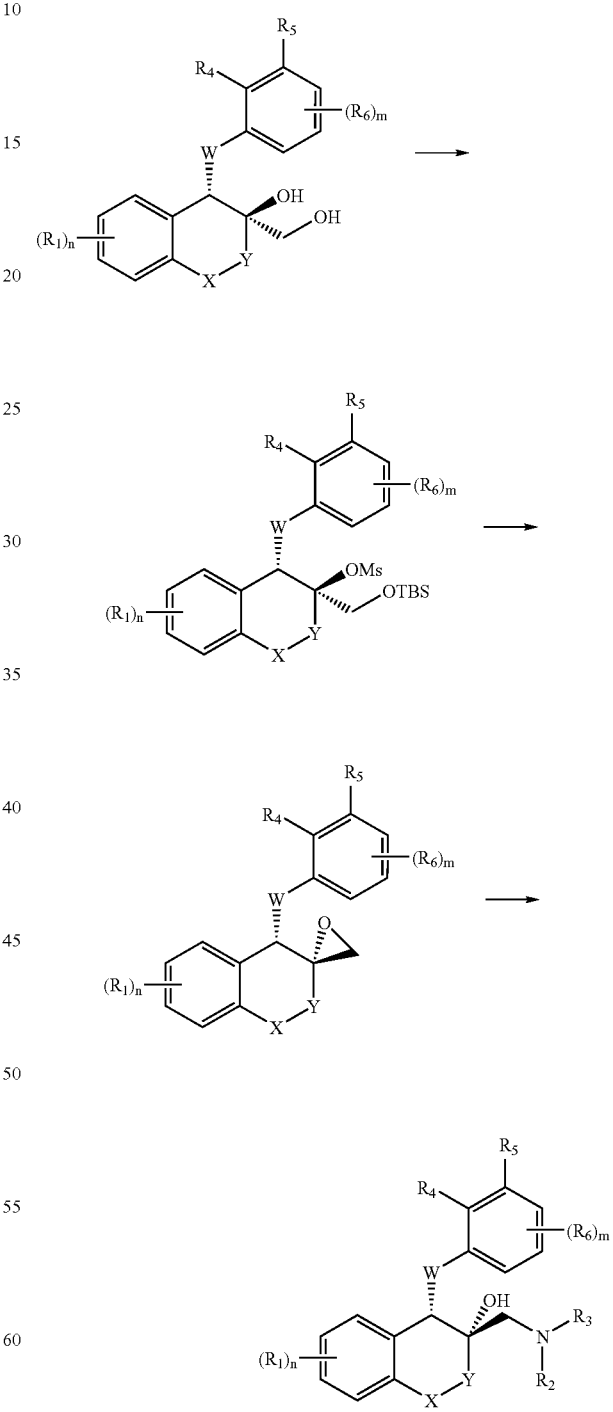

Reaction Scheme 3

The other diastereomer can be accessed from the intermediate diol by protection of the primary alcohol with, for example, a silyl group, followed by activation of the tertiary alcohol, for example, by forming the mesylate. The primary alcohol is deprotected and the exo epoxide is generated predominantly with inversion of configuration by treatment with base. Treatment with a primary or secondary amine gives the amino alcohol diastereomer with W and the OH cis to each other.

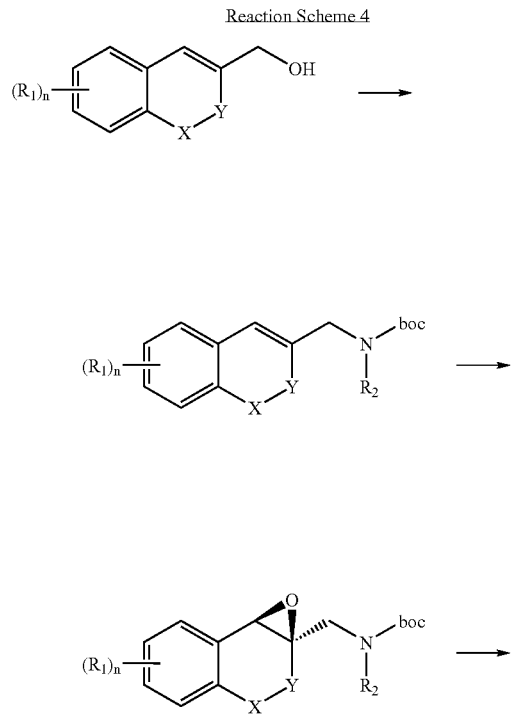

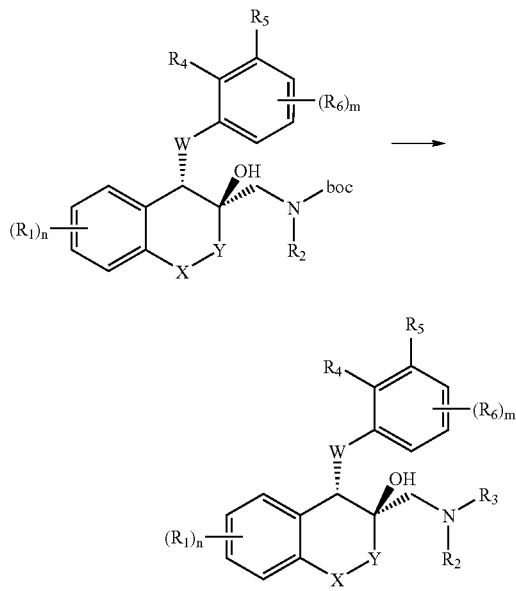

An alternative synthesis is to convert the cyclic allylic alcohol into the protected secondary amine, for example, by oxidizing to the aldehyde followed by reductive amination with a primary amine and protection of the amine, for example, with Boc. The protected amine is then epoxidized in the same manner as above, and the epoxide is opened with the metal salt of a phenol (or thiophenol or carbanion). Deprotection gives the secondary amine where $R_3$=H. If desired the tertiary amine is produced by reductive amination with an aldehyde or ketone, or by alkylation with an alkyl halide.

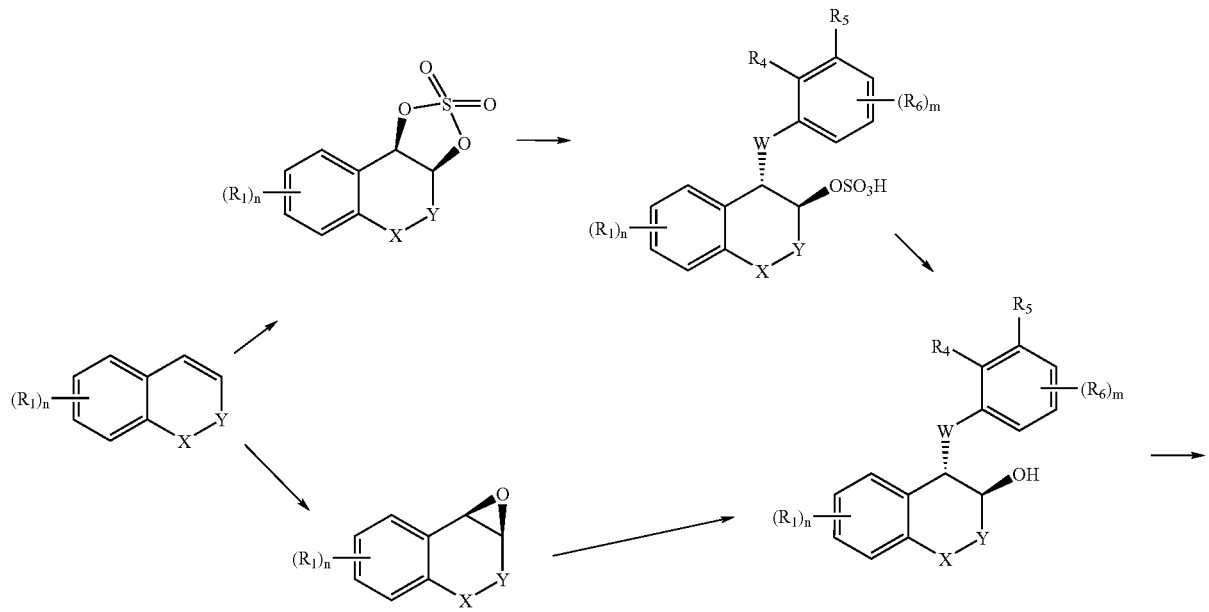

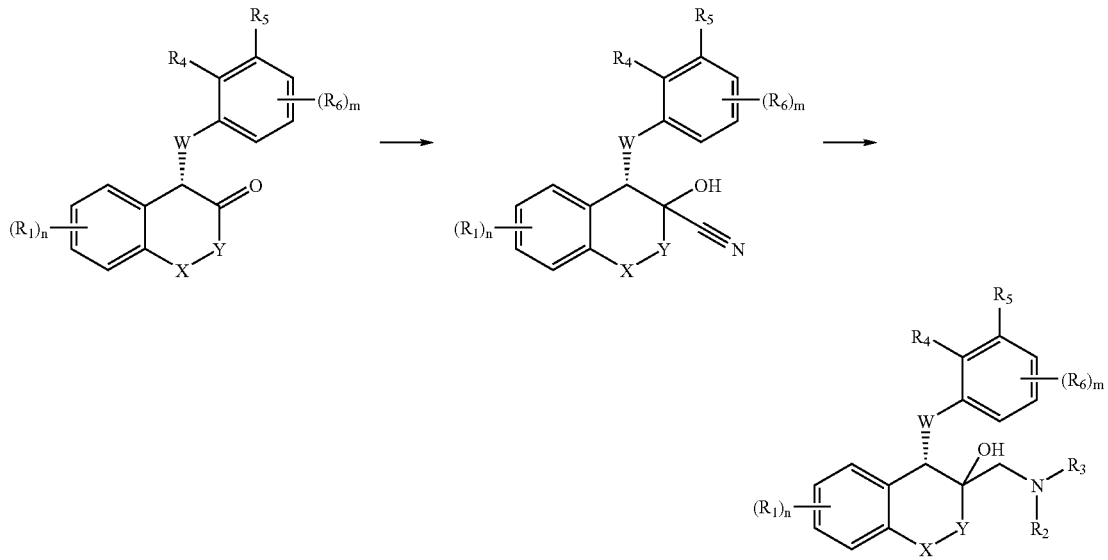

Another alternative synthesis starts with a cyclic alkene that is converted to the epoxide or the cyclic sulfate. Ring opening with the metal salt of a phenol (or thiophenol or carbanion) produces a cyclic secondary alcohol that can be converted to the cyanohydrin. Reduction, for example with lithium aluminum hydride, produces a mixture of the primary amine diastereomers that can be converted by reductive amination to the secondary or tertiary amines. Other variations in these steps such as conversion of the nitrile to the primary amide, followed by reduction will be readily discernable for one skilled in the art.

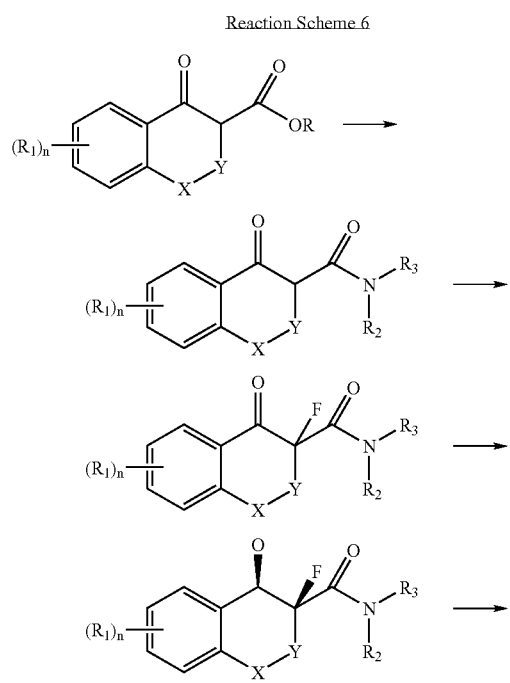

Reaction Scheme 6

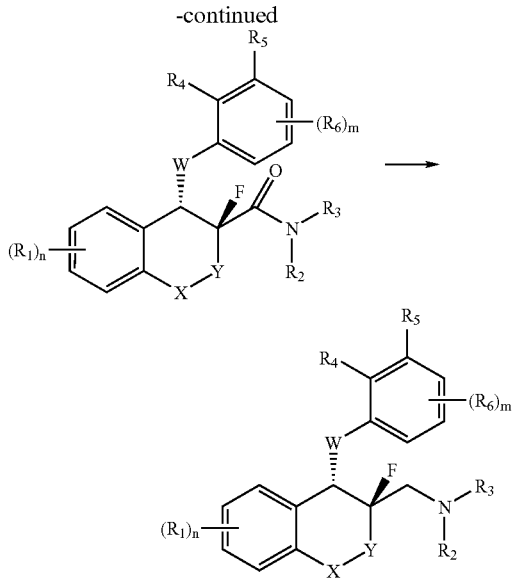

One synthesis of compounds where Z=F and W=O or S starts with the cyclic ketoester that is converted to the appropriate amide by direct displacement with a metal salt of secondary or tertiary amine. The ketoamide anion is then treated with a fluorinating agent for example SelectFluor® and if present the secondary amide is converted to the tertiary amide by alkylation of a metal salt of the amide with an alkyl halide such as allyl bromide. The ketone is then reduced to the alcohol with, for example, catechol borane. Displacement of the alcohol with a phenol (or thiophenol) under Mitsunobu conditions and reduction of the amide with, for example, lithium aluminum hydride generates the tertiary amine. Reaction with a chloroformate followed by solvolysis, or direct deprotection of the $R_3$ group such as a palladium mediated deprotection of an allyl group generates the secondary amine product.

Reaction Scheme 7

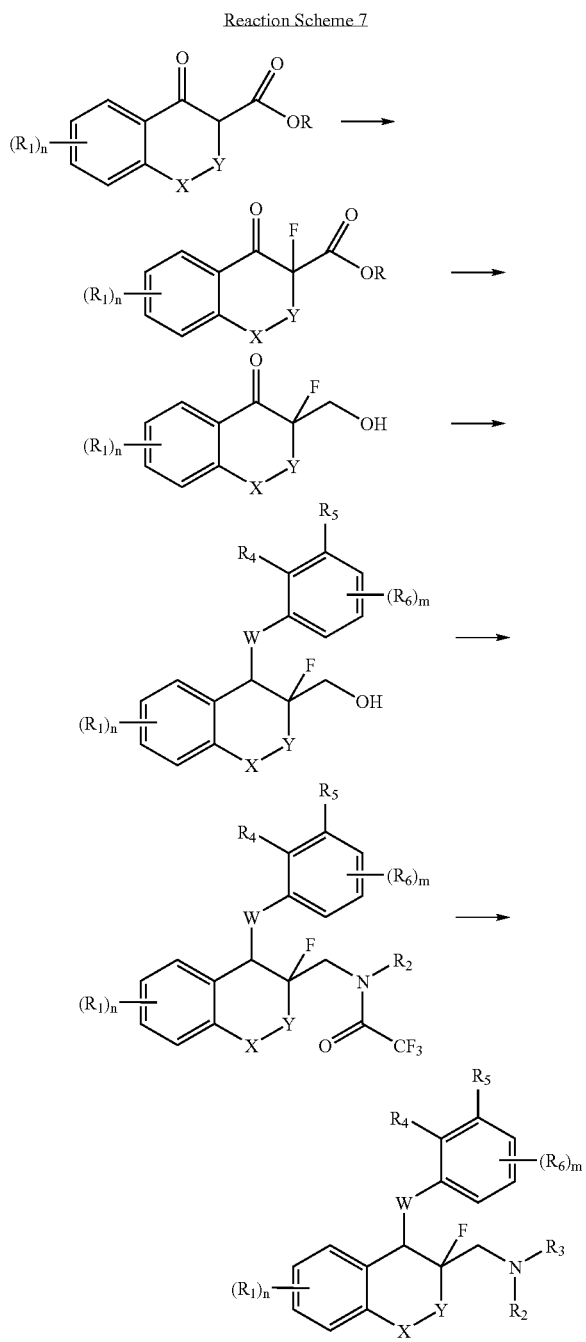

Alternatively, the ketoester anion can be treated directly with a fluorinating agent. Reduction with a reagent such as sodium borohydride gives the fluoro diol. Protection of the primary alcohol with, for example TBDMS, followed by Mitsunobu reaction of the benzyl alcohol with a phenol and deprotection gives the phenoxy alcohol. Mitsunobu mediated displacement with a protected secondary amine such as an N-alkyl trifluoroacetamide followed by deprotection, such as by base mediated hydrolysis, gives the secondary amine product that can optionally be converted to the tertiary amine by reductive amination with an aldehyde or ketone or by alkylation with an alkyl halide. Mild oxidation of the fluoroalcohol intermediate to the aldehyde followed by reductive amination with the appropriate amine is a further alternative.

The compounds of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the compounds of structure (I). Further, in the case of a carboxylic acid (—COOH), esters may be employed, such as methyl esters, ethyl esters, and the like.

With regard to stereoisomers, the compounds of structure (I) may have chiral centers and may occur as racemates, racemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

As mentioned above, the compounds of this invention and their salts may inhibit the uptake of one or more of the monoamine neurotransmitters serotonin, noradrenaline and dopamine. As such, these compounds and their salts may have utility over a wide range of therapeutic applications, and may be used to treat a variety of disorders which are caused by or linked to decreased neurotransmission of one or more of these monoamines. These disorders include disorders of the central and/or peripheral nervous system.

In an embodiment, the compounds of the present invention may selectively inhibit the re-uptake of serotonin and noradrenaline over the re-uptake of dopamine. Other compounds of the present invention may selectively inhibit noradrenaline over both serotonin and dopamine. In another embodiment, compounds of the present invention may selectively inhibit the re-uptake of serotonin over both noradrenaline and dopamine.

In an embodiment, conditions which may be treated by compounds of the current invention include, but are not limited to, depression, eating disorders, schizophrenia, inflammatory bowel disorders, pain, addiction disorders, urinary incontinence, dementia, Alzheimer's, memory loss, Parkinsonism, anxiety, attention-deficit disorder, social phobia, obsessive compulsive disorder, substance abuse and withdrawal, cognitive disorders, fibromyalgia and sleep disorders.

Pain may generally be divided into two categories: acute pain and chronic (or persistent) pain. Acute pain is self-limiting and generally results from injured or diseased tissue and is considered nociceptive in nature. Examples of nociceptive pain include post-operative pain, pain associated with trauma, and the pain of arthritis. Chronic pain can be defined as pain that persists beyond the usual course of the acute injury or disease. Chronic pain is generally neuropathic in nature and can be continuous or recurring. Chronic pain is generally caused by prolonged and sometimes permanent dysfunction of the central or peripheral nervous system. Examples include post herpetic (or post-shingles) neuralgia, reflex sympathetic dystrophy/causalgia (nerve trauma), components of cancer pain, phantom limb pain, entrapment neuropathy (e.g., carpal tunnel syndrome), and peripheral neuropathy (widespread nerve damage due to, for instance, diabetes or excessive alcohol use).

In another embodiment, a compound of structure (I) may be administered along with an antipsychotic to treat schizophrenia. The antipsychotic may be typical or atypical. A compound of structure (I) could also be administered with a dopaminergic agent such as levodopa to treat Parkinson's disease and/or the side effects associated with such therapy.

In another embodiment of the invention, pharmaceutical compositions containing one or more monoamine re-uptake inhibitors are disclosed. For the purposes of administration, the compounds of the present invention may be formulated as pharmaceutical compositions. Pharmaceutical compositions of the present invention comprise a monoamine re-uptake inhibitor of the present invention and a pharmaceutically acceptable carrier and/or diluent. The monoamine re-uptake inhibitor is present in the composition in an amount which is effective to treat a particular disorder—that is, in an amount sufficient to achieve monoamine re-uptake inhibition, and preferably with acceptable toxicity to the patient. Typically, the pharmaceutical compositions of the present invention may include a monoamine re-uptake inhibitor in an amount from 0.1 mg to 250 mg per dosage depending upon the route of administration, and more typically from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a monoamine re-uptake inhibitor, diluents, dispersing and surface active agents, binders, and lubricants. One skilled in this art may further formulate the monoamine re-uptake inhibitor in an appropriate manner, and in accordance with accepted practices, such as those disclosed in *Remington's Pharmaceutical Sciences*, Gennaro, Ed., Mack Publishing Co., Easton, Pa. 1990.

In another embodiment, the present invention provides a method for treating disorders of the central or peripheral nervous system. Such methods include administering of a compound of the present invention to a warm-blooded animal in an amount sufficient to treat the condition. In this context, "treat" includes prophylactic administration. Such methods include systemic administration of a monoamine re-uptake inhibitor of this invention, preferably in the form of a pharmaceutical composition as discussed above. As used herein, systemic administration includes oral and parenteral methods of administration. For oral administration, suitable pharmaceutical compositions of monoamine re-uptake inhibitors include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the monoamine re-uptake inhibitor, buffers, antioxidants, bacteriostats, and other additives commonly employed in such solutions.

The following examples are provided for purposes of illustration, not limitation. In summary, the monoamine re-uptake inhibitors of this invention may be assayed by the methods disclosed in Examples 23 to 27, while the following Examples 1 to 22 disclose the synthesis of representative compounds of this invention.

EXAMPLES

HPLC Methods for analyzing the samples
Retention time, $t_R$, in minutes

Analytical HPLC-MS Method 1
Platform: Agilent 1100 series: equipped with an auto-sampler, an UV detector (220 nM and 254 nM), a MS detector (APCI);
HPLC column: Phenomenex Synergi-Max RP, 2.0×50 mm column;
HPLC gradient: 1.0 mL/minute, from 10% acetonitrile in water to 90% acetonitrile in water in 2.5 minutes, maintaining 90% for 1 minute. Both acetonitrile and water have 0.025% TFA.

Analytical HPLC-MS Method 2
Platform: Agilent 1100 series: equipped with an auto-sampler, an UV detector (220 nM and 254 nM), a MS detector (APCI);
HPLC column: Phenomenex Synergi-Max RP, 2.0×50 mm column;
HPLC gradient: 1.0 mL/minute, from 5% acetonitrile in water to 95% acetonitrile in water in 13.5 minutes, maintaining 95% for 2 minute. Both acetonitrile and water have 0.025% TFA.

Analytical HPLC-MS Method 3
Platform: Agilent 1100 series: equipped with an auto-sampler, an UV detector (220 nM and 254 nM), a MS detector (electrospray);
HPLC column: XTerra MS, $C_{18}$, 5μ, 3.0×250 mm column;
HPLC gradient: 1.0 mL/minute, from 10% acetonitrile in water to 90% acetonitrile in water in 46 minutes, jump to 99% acetonitrile and maintain 99% acetonitrile for 8.04 minutes. Both acetonitrile and water have 0.025% TFA.

Analytical HPLC-MS Method 4

Platform: Agilent 1100 series: equipped with an auto-sampler, an UV detector (220 nM and 254 nM), a MS detector (APCI) and Berger FCM 1200 $CO_2$ pump module;

HPLC column: Berger Pyridine, PYR 60A, 6μ, 4.6×150 mm column;

HPLC gradient: 4.0 mL/minute, 120 bar; from 10% methanol in supercritical $CO_2$ to 60% methanol in supercritical $CO_2$ in 1.67 minutes, maintaining 60% for 1 minute. Methanol has 1.5% water. Backpressure regulated at 140 bar.

Analytical HPLC-MS Method 5

Platform: Gilson 215 Auto-sampler, Dionex Thermostatted Column Compartment TCC-100 held at 30° C., Dionex PDA-100 Photodiode Array Detector (220 nm and 254 nm), Dionex P680 HPLC pump, Thermo Finnigan MSQ single quad Mass Spectrometer (APCI)

HPLC column: Phenomenex Gemini 5μ C18 110A, 3.0× 150 mm

HPLC gradient: 1.5 mL/min, from 5% acetonitrile in water to 90% acetonitrile in water in 9.86 minutes, from 90% acetonitrile in water to 95% acetonitrile in water in 0.1 minutes, hold at 95% for 1.19 minutes. Both acetonitrile and water have 0.04% $NH_4OH$ Preparative HPLC-MS Platform: Shimadzu HPLC equipped with a Gilson 215 auto-sampler/fraction collector, UV detector and a PE Sciex API150EX mass detector;

HPLC column: BHK ODS-O/B, 5μ, 30×75 mm

HPLC gradient: 35 mL/minute, 10% acetonitrile in water to 100% acetonitrile in 7 minutes, maintaining 100% acetonitrile for 3 minutes, with 0.025% TFA.

Chiral HPLC

Platform: Dionex P680A and P680P pumps, Dionex PAD 100 photodiode array detector, Jasco CD 2095 plus chiral detector, Gilson 215 liquid handler. Analytical Columns are 0.46×25 cm, 5 μm; preparative columns are 2×25 cm, 5 μm.

Example 1

2-Methylaminomethyl-1-o-tolyloxy-indan-2-ol

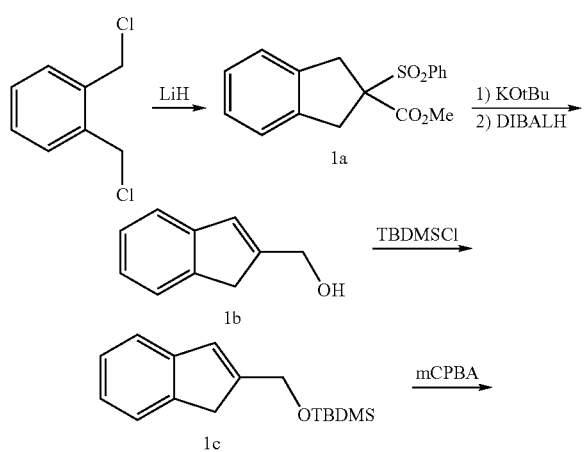

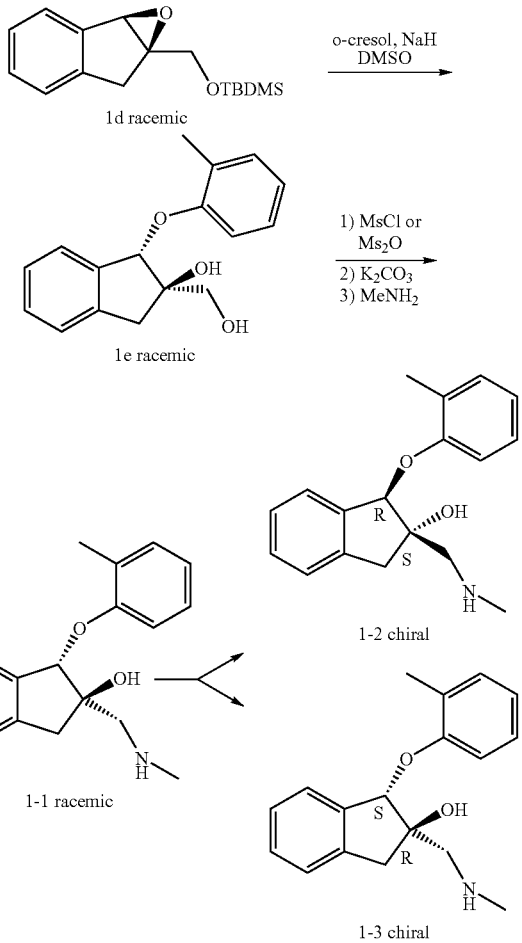

Step 1A

To methyl phenylsulfonylacetate (50.0 g, 234 mmol) in N,N-dimethylformamide (200 mL) at 0° C. was added lithium hydride (5.05 g, 631 mmol) in portions over 5 min. The mixture was stirred with external ice-bath cooling for 2 h, then the bath was removed and the mixture stirred for 1 h. The mixture was cooled with the ice-bath, and α,α-dichloro-o-xylene (47.0 g, 269 mmol) in N,N-dimethylformamide (50 mL) was added dropwise over 30 min. The mixture was stirred for 6 h at 0° C. and was allowed to warm to room temperature overnight. After stirring for an additional 48 hours, the mixture was quenched carefully with saturated aqueous ammonium chloride solution (30 mL), diluted with water (750 mL), and filtered. The precipitate was washed with water (3×100 mL), dissolved in a minimum amount of dichloromethane, dried over magnesium chloride, and filtered. Evaporation of the organics, followed by recrystallization of the resulting crude solid with 1 L of dry methanol, gave 1a as white crystals (62.4 g, 85%).

APCI MS m/e: 317.0 ([M+H]$^+$).

Step 1B

To a suspension of 1a (25.0 g, 79.0 mmol) in tetrahydrofuran (250 mL) at −65° C. (dry ice/iPrOH bath) temperature was added potassium t-butoxide (32.8 g, 293 mmol) in THF (250 mL) over 5 min. Stirring was continued for 10 min, then the mixture was quenched with saturated aqueous ammonium chloride solution (400 mL), and extracted with ethyl acetate (3×200 mL). The organics were washed with water (200 mL) and saturated aqueous sodium bicarbonate (200 mL), dried over MgSO$_4$, and evaporated to give the mixture of esters (methyl and t-butyl) as an off-white solid (14.3 g). To this crude mix (14.3 g) in dry diethyl ether (300 mL) at 0° C. was added diisobutylaluminum hydride in hexane (1M, 175 mL, 175 mmol) dropwise over 45 min such that the internal temperature did not go above 6° C. The cooling bath was removed and the mixture stirred an additional 45 minutes, then carefully poured into 3M aqueous sodium hydroxide (300 mL). The layers were separated and the aqueous extracted with a further diethyl ether (3×200 mL). The combined organics were washed with water (300 mL), brine (300 mL) and dried over magnesium sulfate. Filtration and evaporation gave 1b as a pale yellow solid (10.7 g, 93%).

$^1$H NMR (300 MHz, CDCl$_3$) δ 7.43 (d, J=7.2 Hz, 1H), 7.34 (d, J=7.2 Hz, 1H), 7.23-7.28 (m, 1H), 7.16 (dt, J=7.5, 1.5 Hz, 1H), 6.76 (s, 1H), 4.60 (d, J=5.4 Hz, 2H), 3.44 (s, 2H). APCI MS m/e: 129.0 ([M+H−H$_2$O]$^+$).

Step 1C

To a solution of 1b (22.2 g, 152 mmol) in dichloromethane (350 mL) was added N,N-dimethylaminopyridine (0.93 g, 7.6 mmol), triethylamine (42 mL, 304 mmol) and tert-butyldimethylchlorosilane (26.4 g, 175 mmol). The reaction mixture was allowed to stir at room temperature overnight and then evaporated and purified by silica gel chromatography, eluting with 0-4% ethyl acetate in hexanes. The silyl ether 1c was obtained as a cream-colored solid (34.4 g, 87% yield).

$^1$H NMR (300 MHz, CDCl$_3$) δ 7.41 (d, J=7.5 Hz, 1H), 7.31 (d, J=6.6 Hz, 1H), 7.21-7.26 (m, 1H), 7.13 (dt, J=7.5, 1.2 Hz, 1H), 6.69 (s, 1H), 4.60 (s, 2H), 3.37 (s, 2H), 0.94 (s, 9H), 0.11 (s, 6H). APCI MS m/e: 129.0 ([M+H−H$_2$O-t-BDMS]$^+$).

Step 1D

To a mixture of the t-butyldimethylsilyl protected alcohol 1c (200 mg, 0.77 mmol) and sodium bicarbonate (160 mg, 1.90 mmol) in dichloromethane (10.0 mL) at 0° C., m-chloroperbenzoic acid (215 mg, 0.92 mmol) was added. After stirring at 0° C. for six hours, the mixture was filtered and the precipitate was rinsed with cold dichloromethane (2×1 mL). The filtrate was washed with a saturated sodium bicarbonate solution (2×5 mL), dried over magnesium sulfate and evaporated under reduced pressure to give the epoxide 1d. The reaction was repeated using 5 g of 1c, 3.87 g of sodium bicarbonate and m-chloroperbenzoic acid (5.32 g).

Step 1E

Sodium hydride (60% dispersion on oil, 26 mg, 0.64 mmol) was added to DMSO (1.0 ml), followed by o-cresol (66 μL, 0.64 mmol). The mixture was stirred with gentle warming for about 5 minutes until it became homogeneous. To this mixture was added zinc chloride (4 mg, 0.03 mmol) and one third of the intermediate 1d above, as a solution in DMSO (1.0 mL). The reaction mixture was heated in a sealed vessel at 75° C., under nitrogen overnight. The cooled mixture was then diluted with ether (10 mL) and water (3 mL). The organic layer was separated and the aqueous layer was further extracted with ether (2×10 mL). The combined organic extracts were washed with saturated sodium bicarbonate solution (10 mL) and dried over magnesium sulfate. Evaporation and chromatography on silica gel using 5-40% ethyl acetate in hexanes gave the diol 1e (48 mg, 70%).

On a larger scale, to sodium hydride (60% dispersion on oil, 2.30 g, 57.6 mmol) in a 350 mL pressure vessel was added DMSO (75 mL), followed carefully by o-cresol (6.0 mL, 57.6 mmol). The mixture was stirred with gentle warming for about 20 minutes until it became homogeneous. To this mixture was added, via cannula, the epoxide 1d, as a solution in DMSO (20 mL+5 mL rinse), followed by anhydrous zinc chloride (522 mg, 3.8 mmol). The reaction mixture was heated at 80° C., under nitrogen, overnight. The cooled mixture was then quenched with water (200 mL) and extracted with ethyl acetate (5×200 mL). The combined organic extracts were washed with saturated sodium bicarbonate solution (250 mL) and dried over magnesium sulfate. Evaporation and chromatography on silica gel using 5-50% ethyl acetate in hexanes gave the diol 1e (3.64 g, 70%).

$^1$H NMR (300 MHz, CDCl$_3$) δ 7.16-7.34 (m, 7H), 6.95 (dt, J=6.6, 2.1 Hz, 1H), 5.81 (s, 1H), 4.11 (d, J=11.1 Hz, 1H), 3.63-3.71 (m, 1H), 3.13 (s, 2H), 2.19 (s, 3H).

APCI MS m/e: 253.0 ([M+H]$^+$).

Step 1F

Diol 1e (97 mg, 0.36 mmol) was dissolved in dichloromethane (2 mL) and cooled to 0° C. Triethylamine (111 μL, 0.79 mmol) and methanesulfonyl chloride (30 μL, 0.38 mmol) were added to this mixture. The reaction was stirred for one hour at 0° C., diluted with ether (20 mL) and washed with saturated sodium bicarbonate (2×5 mL). The organic layer was dried over magnesium sulfate and evaporated to give the mesylate. This intermediate was dissolved in N,N-dimethylformamide (2 mL) and treated with potassium carbonate (250 mg, 1.8 mmol). After an hour at room temperature, the mixture was diluted with ether (20 mL) and washed with water (3×5 mL). The organic layer was dried over magnesium sulfate and evaporated to give the crude epoxide intermediate. This intermediate was dissolved in tetrahydrofuran (1.1 mL) and treated with methylamine (2.0 M in THF, 0.9 mL, 1.8 mmol). The reaction mixture was heated at 65° C. overnight. Excess solvent was evaporated and the residue was redissolved in DMF (0.5 mL). Potassium carbonate (125 mg, 0.9 mmol) was added to this solution and the mixture stirred at room temperature for 2 hours. Methylamine (2.0 M in THF, 0.5 mL, 1.0 mmol) was added and the reaction heated at 70° C. for 3 hours. The reaction mixture was diluted with ethyl acetate (10 mL) and washed with saturated bicarbonate solution (5 mL). The organic layer was dried over magnesium sulfate and evaporated. Purification of a portion of this crude mixture on prep HPLC gave 1-1 as a TFA salt. Conversion to the free base afforded the amine 1-1 as a pale yellow oil (30 mg).

Alternatively, methanesulfonic anhydride may be used in place of methanesulfonyl chloride. Diol 1e (4.30 g, 15.9 mmol) was dissolved in dichloromethane (50 mL) and cooled to −30° C. external. Triethylamine (3.3 mL, 24 mmol), then methanesulfonic anhydride (2.91 g, 16.7 mmol) were added. The reaction mix was warmed to 0° C. over 20 minutes, then stirred for an additional 40 minutes. The mixture was washed with saturated sodium bicarbonate (20 mL). The organic layer was dried over magnesium sulfate and evaporated to give the mesylate. This intermediate was dissolved in N,N-dimethylformamide (50 mL) and treated with potassium carbonate (6.6 g, 48 mmol) in a pressure vessel. After stirring 1.5 h at room temperature, methylamine (2.0 M in THF, 40 mL, 80 mmol) was added and the mixture was heated at 70° C. overnight. The reaction mixture was diluted with ethyl acetate (100 mL) and washed with saturated sodium bicarbonate solution (100 mL). The aqueous was extracted with ethyl acetate (2×100 mL). The combined organics were dried over magnesium sulfate and evaporated to give 4.7 g of a brown oil. Crystallization from cold ether (20 mL) gave 0.9 g of 1-1 as white crystals. Crystallization of the mother liquor with MTBE gave a further 0.3 g as off-white crystals. A further crop of tan solid (0.7 g) was obtained by crashing out the mother liquor with a 1:1 mixture of ether/hexane. Finally, purification of the remaining crude (from the mother liquor) by prep-LCMS gave 1.30 g as a white solid. Total yield of 1-1=3.2 g (71%, 99%+pure).

$^1$H NMR (300 MHz, CDCl$_3$) δ 7.14-7.33 (m, 7H), 6.92 (t, J=7.2 Hz, 1H), 5.67 (s, 1H) 3.27 (d, J=12.3 Hz, 1H), 3.17 (d, J=16.2 Hz, 1H), 3.07 (d, J=16.2 Hz, 1H), 2.71 (d, J=12.3 Hz, 1H), 2.49 (s, 3H), 2.16 (s, 3H). APCI MS m/e: 284.0 ([M+H]$^+$).

Step 1G

The enantiomerically pure compounds, 1-2 and 1-3 (6 mg each, 52% recovery), were obtained from racemic 1-1 (23 mg) by chiral preparative HPLC using a Chiralcel OD-H column eluting with 95:5 hexanes/isopropanol with 0.1% diethylamine at a flow rate of 15 mL/min. On a larger scale, the enantiomerically pure compounds 1-2 and 1-3 (1.41 g each, 90% recovery), were obtained from racemic 1-1 (3.1 g) by chiral preparative SFC using a Chiralpak AS-H column eluting with 15% methanol with 0.5% N,N-dimethylethylamine at a flow rate of 60 mL/min (100 bar, 35° C., 80 mg load, 5.8 min run).

The following compounds were made according to this procedure.

| No. | | —NR$_2$R$_3$ | W | Stereochem | MW | MH$^+$ | $t_R$ (method) |
|---|---|---|---|---|---|---|---|
| 1-1 | 2-CH$_3$-phenyl | —N(H)CH$_3$ | O | R,S and S,R | 283.4 | 284.0 | 4.56 (2) |
| 1-2 | 2-CH$_3$-phenyl | —N(H)CH$_3$ | O | R,S | 283.4 | 284.1 | 4.44 (2) |
| 1-3 | 2-CH$_3$-phenyl | —N(H)CH$_3$ | O | S,R | 283.4 | 284.1 | 4.44 (2) |
| 1-4 | phenyl | —N(H)CH$_3$ | O | R,S and S,R | 269.3 | 270.0 | 4.00 (2) |
| 1-5 | 1-naphthyl | —N(H)CH$_3$ | O | R,S and S,R | 319.4 | 320.0 | 5.06 (2) |
| 1-6 | 2-CH$_3$-phenyl | —N(H)ethyl | O | R,S and S,R | 297.4 | 298.1 | 4.77 (2) |
| 1-7 | 2-CH$_3$CH$_2$-phenyl | —N(H)CH$_3$ | O | R,S and S,R | 297.4 | 298.1 | 4.86 (2) |
| 1-8 | 2,3-di-CH$_3$-phenyl | —N(H)CH$_3$ | O | R,S and S,R | 297.4 | 298.1 | 4.90 (2) |
| 1-9 | 2,4-di-CH$_3$-phenyl | —N(H)CH$_3$ | O | R,S and S,R | 297.4 | 298.1 | 5.05 (2) |
| 1-10 | 2-CH$_3$O-phenyl | —N(H)CH$_3$ | O | R,S and S,R | 299.4 | 300.1 | 4.19 (2) |
| 1-11 | 2-CH$_3$O-phenyl | —N(H)CH$_3$ | O | S,R | 299.4 | 300.1 | 4.07 (2) |
| 1-12 | 2-Cl-phenyl | —N(H)CH$_3$ | O | R,S and S,R | 303.8 | 304.0 | 4.54 (2) |
| 1-13 | 2-Cl-phenyl | —N(H)CH$_3$ | O | S,R | 303.8 | 304.1 | 15.11 (3) |
| 1-14 | 2-CH$_3$-phenyl | —N(CH$_3$)$_2$ | O | R,S and S,R | 297.4 | 298.1 | 4.59 (2) |
| 1-15 | 2-Br-phenyl | —N(H)CH$_3$ | O | R,S and S,R | 348.2 | 347.9 | 5.81 (2) |
| 1-16 | 2-methyl-benzo[b]thiophen-7-yl | —N(H)CH$_3$ | O | R,S and S,R | 339.5 | 340.0 | 5.29 (2) |
| 1-17 | Benzo[b]thiophen-4-yl | —N(H)CH$_3$ | O | R,S and S,R | 325.4 | 326.0 | 4.89 (2) |
| 1-18 | Benzo[b]thiophen-4-yl | —N(H)CH$_3$ | O | R,S | 325.4 | 326.0 | 9.73 (2) |
| 1-19 | Benzo[b]thiophen-4-yl | —N(H)CH$_3$ | O | S,R | 325.4 | 326.1 | 10.25 (2) |
| 1-20 | Benzo[b]thiophen-7-yl | —N(H)CH$_3$ | O | R,S and S,R | 325.4 | 326.0 | 4.79 (2) |
| 1-21 | 2,2-Dimethyl-benzo[1,3]dioxol-4-yl | —N(H)CH$_3$ | O | R,S and S,R | 341.4 | 342.0 | 4.84 (2) |
| 1-22 | 2-CH$_3$-4-F-phenyl | —N(H)CH$_3$ | O | R,S and S,R | 301.4 | 302.0 | 4.73 (2) |
| 1-23 | 2-CH$_3$-4-F-phenyl | —N(H)CH$_3$ | O | R,S | 301.4 | 302.0 | 4.47 (2) |
| 1-24 | 2-CH$_3$-4-F-phenyl | —N(H)CH$_3$ | O | S,R | 301.4 | 302.0 | 4.57 (2) |
| 1-25 | 2,5-di-CH$_3$-phenyl | —N(H)CH$_3$ | O | R,S and S,R | 297.4 | 298.0 | 7.69 (2) |
| 1-26 | 2-CH$_3$-phenyl | —N(H)CH$_3$ | S | R,S and S,R | 299.4 | 300.1 | 4.80 (2) |
| 1-27 | 2,4-di-CH$_3$-phenyl | —N(H)CH$_3$ | O | R,S | 297.4 | 298.1 | 4.91 (2) |
| 1-28 | 2,2-dimethyl-benzo[1,3]dioxol-4-yl | —N(H)CH$_3$ | O | R,S | 341.4 | 342.0 | 4.67 (2) |
| 1-29 | 2,4-di-CH$_3$-phenyl | —N(H)CH$_3$ | O | S,R | 297.4 | 298.1 | 4.90 (2) |
| 1-30 | 2,2-dimethyl-benzo[1,3]dioxol-4-yl | —N(H)CH$_3$ | O | S,R | 341.4 | 342.0 | 4.70 (2) |
| 1-31 | 2-CH$_3$-phenyl | —N(H)CH$_3$ | S | S,R | 299.4 | 299.9 | 9.08 (5) |
| 1-32 | 2,3-di-CH$_3$-phenyl | —N(H)CH$_3$ | O | S,R | 297.4 | 298.1 | 9.43 (2) |

-continued

| No. | | —NR$_2$R$_3$ | W | Stereochem | MW | MH$^+$ | $t_R$ (method) |
|---|---|---|---|---|---|---|---|
| 1-33 | 2-CH$_3$-phenyl | —N(H)CH$_3$ | S | R,S | 299.4 | 300.3 | 9.96 (2) |
| 1-34 | 2-Ethyl-phenyl | —N(H)CH$_3$ | O | S,R | 297.4 | 298.1 | 4.86 (2) |
| 1-35 | 2-Ethyl-phenyl | —N(H)CH$_3$ | O | R,S | 297.4 | 298.1 | 4.86 (2) |
| 1-36 | 2,3-di-CH$_3$-phenyl | —N(H)CH$_3$ | O | R,S | 297.4 | 298.1 | 4.84 (2) |
| 1-37 | 2-CH$_3$S-phenyl | —N(H)CH$_3$ | O | R,S and S,R | 315.4 | 316.0 | 4.36 (2) |
| 1-38 | 2-F-phenyl | —N(H)CH$_3$ | O | R,S and S,R | 287.3 | 288.0 | 3.92 (2) |
| 1-39 | 3-F-2-CH$_3$-phenyl | —N(H)CH$_3$ | O | R,S | 301.4 | 302.1 | 4.67 (2) |
| 1-40 | 2-CH$_3$S-phenyl | —N(H)CH$_3$ | O | R,S | 315.4 | 316.0 | 4.43 (2) |
| 1-41 | 2-CH$_3$S-phenyl | —N(H)CH$_3$ | O | S,R | 315.4 | 316.0 | 4.47 (2) |
| 1-42 | 5-F-2-CH$_3$-phenyl | —N(H)CH$_3$ | O | R,S and S,R | 301.4 | 302.0 | 4.58 (2) |
| 1-43 | 2-F-phenyl | —N(H)CH$_3$ | O | R,S | 287.3 | 288.0 | 3.80 (2) |
| 1-44 | 2-F-phenyl | —N(H)CH$_3$ | O | S,R | 287.3 | 288.1 | 12.48 (3) |
| 1-45 | 5-F-2-CH$_3$-phenyl | —N(H)CH$_3$ | O | R,S | 301.4 | 302.0 | 4.54 (2) |
| 1-46 | 5-F-2-CH$_3$-phenyl | —N(H)CH$_3$ | O | S,R | 301.4 | 302.1 | 15.08 (3) |
| 1-47 | 2-F-6-CH$_3$-phenyl | —N(H)CH$_3$ | O | R,S and S,R | 301.4 | 302.0 | 4.27 (2) |
| 1-48 | 2-F-6-CH$_3$-phenyl | —N(H)CH$_3$ | O | S,R | 301.4 | 302.1 | 13.82 (3) |
| 1-49 | 2-F-6-CH$_3$-phenyl | —N(H)CH$_3$ | O | R,S | 301.4 | 302.0 | 4.16 (2) |
| 1-50 | 2-CH$_3$-phenyl | —N(H)CH$_2$—CH$_2$OH | O | S,R | 313.4 | 314.0 | 4.23 (2) |

Example 2

2-Aminomethyl-1-o-tolyloxy-indan-2-ol

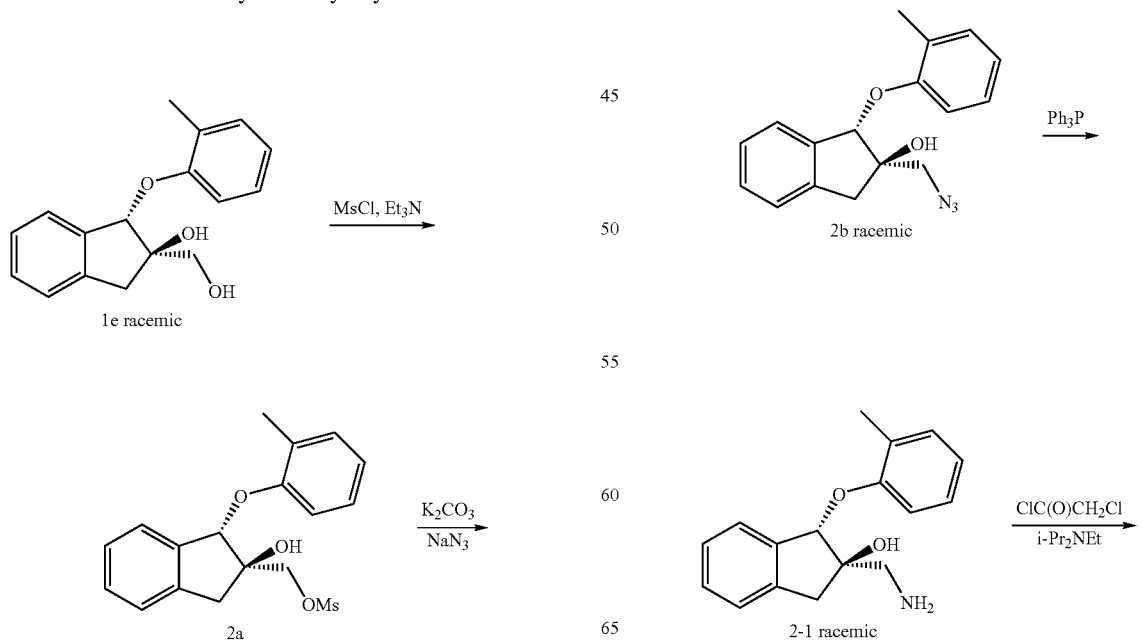

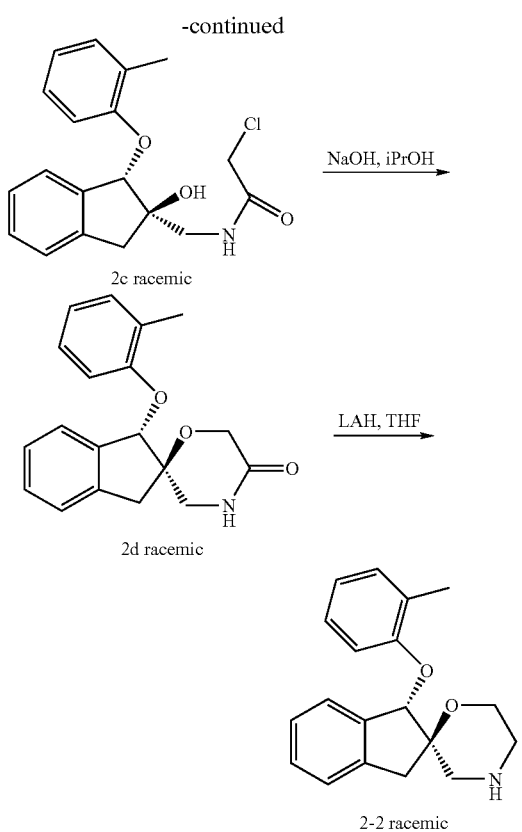

Step 2A

To the solution of the alcohol 1e (127 mg, 0.47 mmol) in dichloromethane at 0° C., triethylamine (100 μL, 0.71 mmol) and methanesulfonyl chloride (40 μL, 0.52 mmol) were added. After one hour at this temperature, the reaction mixture was diluted with dichloromethane (10 mL) and washed with a saturated sodium bicarbonate solution (5 mL). The organic layer was dried over magnesium sulfate, filtered and evaporated to give the crude mesylate 2a (168 mg), which was used without further manipulation.

Step 2B

A solution of the crude mesylate 2a (135 mg, 0.39 mmol) in N,N-dimethylformamide (2.5 mL) was treated with potassium carbonate (161 mg, 1.16 mmol). After two hours at room temperature, sodium azide (126 mg, 1.94 mmol) and 15-crown-5 (15 μL, 0.07 mmol) were added to the reaction mixture and the temperature was elevated to 70° C. Heating was continued overnight and the reaction was then diluted with water (3 mL) and extracted with ether (3×5 mL). The combined organic extracts were washed with saturated sodium bicarbonate solution (5 mL) and dried over magnesium sulfate. Filtration and evaporation, followed by silica gel chromatography (20% ethyl acetate in hexanes) gave the desired azide 2b as a yellow oil (85 mg, 75%).

$^1$H NMR (300 MHz, CDCl$_3$) δ 7.14-7.33 (m, 7H), 6.93 (dt, J=7.5, 1.5 Hz, 1H), 5.65 (s, 1H), 3.89 (d, J=12.3 Hz, 1H), 3.59 (d, J=12.6 Hz, 1H), 3.37 (d, J=16.2 Hz, 1H), 3.02 (d, J=16.2 Hz, 1H), 2.12 (s, 3H). APCI MS m/e: 279.0 ([M+H−H$_2$O]$^+$).

Step 2C

The azide 2b (85 mg, 0.29 mmol) was dissolved in tetrahydrofuran (1.5 mL) and treated with triphenylphosphine (113 mg, 0.43 mmol). After an hour, distilled water (100 μL, 5.76 mmol) was added, and the reaction vessel was heated at 65° C. for one hour. After stirring for 2 days at room temperature, the reaction mixture was concentrated and dissolved in methanol (2 mL). Purification on a preparatory HPLC/MS gave the desired amine as the trifluoroacetate salt. This residue was dissolved in ethyl acetate (5 mL). This organic solution was washed with saturated sodium bicarbonate (2×2 mL), dried over magnesium sulfate and evaporated to give the free amine 2-1 as a colorless oil (60 mg, 78%).

$^1$H NMR (300 MHz, CDCl$_3$) δ 7.11-7.32 (m, 7H), 6.91 (t, J=7.5 Hz, 1H), 5.70 (s, 1H), 2.80-3.49 (m, 4H), 2.12 (s, 3H). APCI MS m/e: 270.0 ([M+H]$^+$).

Step 2D

N,N-diisopropylethylamine (62 μL, 0.35 mmol) and chloroacetyl chloride (15 μL, 0.19 mmol) were added to a solution of 2-1 (48 mg, 0.18 mmol) in dichloromethane (2 mL) at 0° C. The solution was allowed to warm to room temperature over an hour and stirred at this temperature for 30 minutes. The solvent was removed under reduced pressure and the residue subjected to silica gel chromatography using 0-30% ethyl acetate in dichloromethane to give amide 2c as a pale yellow oil (41 mg, 67%).

$^1$H NMR (300 MHz, CDCl$_3$) δ 7.16-7.36 (m, 7H), 7.00 (br s, 1H), 6.94 (t, J=8.1 Hz, 1H), 5.74 (s, 1H), 3.93 (d, J=15.6 Hz, 1H), 3.86 (d, J=15.6 Hz, 1H), 3.76 (d, J=6.9 Hz, 2H), 3.70 (s, 1H), 3.24 (d, J=15.9 Hz, 1H), 3.11 (d, J=16.2 Hz, 1H), 2.20 (s, 3H) APCI MS m/e: 328.0 ([M+H−H$_2$O]$^+$).

Step 2E

To a solution of 2c (41 mg, 0.12 mmol) in isopropyl alcohol (2 mL) was added water (18 mg) and sodium hydroxide (10 mg, 0.24 mmol). The mixture was stirred for 1.5 hours at room temperature and then diluted with ethyl acetate (50 mL) and washed with saturated bicarbonate solution (10 mL). The organic layer was dried over magnesium sulfate, dried and evaporated to give the crude product, which was purified via silica gel chromatography using 40% ethyl acetate in dichloromethane. Pure 2d was thus obtained as a white solid (25 mg, 68%).

$^1$H NMR (300 MHz, CDCl$_3$) δ 7.16-7.35 (m, 7H), 6.94 (dt, J=7.5, 1.5 Hz, 1H), 5.98 (br s, 1H), 4.41 (d, J=17.4 Hz, 1H), 4.33 (d, J=17.4 Hz, 1H), 3.90 (d, J=12.6 Hz, 1H), 3.41 (d, J=15.6 Hz, 1H), 3.33 (d, J=4.2 Hz, 1H), 3.29 (d, J=4.2 Hz, 1H), 3.24 (d, J=15.3 Hz, 1H), 2.20 (s, 3H). APCI MS m/e: 310.0 ([M+H]$^+$).

Step 2F

To a solution of 2d (15.0 mg, 0.048 mmol) in tetrahydrofuran (1 mL) was added lithium aluminum hydride (1.0 M in THF, 120 μL, 0.12 mmol) dropwise. The mixture was warmed up to 40° C. for one hour and then allowed to cool to room temperature. Water (1 drop), 10% sodium hydroxide solution (1 drop) and more water (3 drops) were added sequentially to the reaction mixture and stirred for 5 minutes. The reaction mixture was filtered through celite, washing with tetrahydrofuran. The solvent was removed under reduced pressure and the residue purified on a preparatory HPLC/MS to give the trifluoroacetate salt of the desired product. This material was dissolved in ethyl acetate (5 mL) and washed with saturated sodium bicarbonate solution (2×2 mL). The organic phase was dried, filtered and evaporated to give 2-2 as a yellow oil (8 mg, 57%).

$^1$H NMR (300 MHz, CDCl$_3$) δ 7.16-7.35 (m, 7H), 6.92 (dt, J=6.3, 0.9 Hz, 1H), 5.76 (s, 1H), 3.85 (d, J=4.8 Hz, 2H), 3.53 (d, J=15.6 Hz, 1H), 3.24 (d, J=12.9 Hz, 1H), 3.08 (d, J=15.9 Hz, 1H), 2.90-2.91 (m, 2H), 2.85 (d, J=12.9 Hz, 1H), 2.23 (s, 3H).

APCI MS m/e: 296.1 ([M+H]$^+$).

The following additional compounds were made according to this procedure. Pure enantiomers were isolated by chiral HPLC.

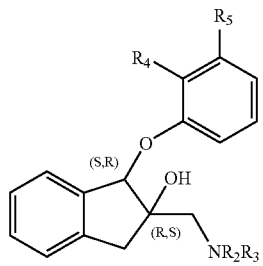

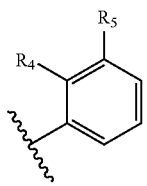

| No. | —NR$_2$R$_3$ | Stereochem | MW | MH$^+$ | t$_R$ (method) |
|---|---|---|---|---|---|
| 2-3 | 2-CH$_3$-phenyl | —NH$_2$ | R,S | 269.3 | 270.0 | 4.35 (2) |
| 2-4 | 2-CH$_3$-phenyl | —NH$_2$ | S,R | 269.3 | 270.0 | 4.36 (2) |
| 2-5 | 2-Cl-phenyl | —NH$_2$ | R,S and S,R | 289.8 | 290.0 | 7.55 (2) |
| 2-6 | 2-Cl-phenyl | —NH$_2$ | S,R | 289.8 | 290.0 | 4.12 (2) |
| 2-7 | 2-Cl-phenyl | —NH$_2$ | R,S | 289.8 | 290.0 | 4.11 (2) |
| 2-8 | 4-F-2-CH$_3$-phenyl | —NH$_2$ | R,S and S,R | 287.3 | 288.0 | 4.53 (2) |
| 2-9 | 3-F-2-CH$_3$-phenyl | —NH$_2$ | R,S and S,R | 287.3 | 288.0 | 4.04 (2) |
| 2-10 | 3-F-2-CH$_3$-phenyl | —NH$_2$ | R,S | 287.3 | 288.0 | 4.41 (2) |
| 2-11 | 3-F-2-CH$_3$-phenyl | —NH$_2$ | S,R | 287.3 | 288.0 | 4.36 (2) |
| 2-12 | 2-F-phenyl | —NH$_2$ | R,S and S,R | 273.3 | 274.0 | 3.74 (2) |
| 2-13 | 2-F-phenyl | —NH$_2$ | R,S | 273.3 | 274.0 | 3.72 (2) |
| 2-14 | 2-F-phenyl | —NH$_2$ | S,R | 273.3 | 274.0 | 3.68 92) |
| 2-15 | 4-F-2-CH$_3$-phenyl | —NH$_2$ | S,R | 287.3 | 288.0 | 4.44 (2) |
| 2-16 | 4-F-2-CH$_3$-phenyl | —NH$_2$ | R,S | 287.3 | 288.0 | 4.46 (2) |
| 2-17 | 2-F-6-CH$_3$-phenyl | —NH$_2$ | R,S and S,R | 287.3 | 288.0 | 4.24 (2) |
| 2-18 | 2-F-6-CH$_3$-phenyl | —NH$_2$ | S,R | 287.3 | 288.0 | 4.34 (2) |
| 2-19 | 5-F-2-CH$_3$-phenyl | —NH$_2$ | R,S and S,R | 287.3 | 288.0 | 4.53 (2) |
| 2-20 | 2-F-6-CH$_3$-phenyl | —NH$_2$ | R,S | 287.3 | 288.0 | 4.18 (2) |
| 2-21 | 5-F-2-CH$_3$-phenyl | —NH$_2$ | S,R | 287.3 | 288.0 | 4.28 (2) |
| 2-22 | 5-F-2-CH$_3$-phenyl | —NH$_2$ | R,S | 287.3 | 288.0 | 4.46 (2) |
| 2-23 | 2-4-di-F-phenyl | —NH$_2$ | R,S and S,R | 305.3 | 306.0 | 4.09 (2) |

Example 3

2-Methylaminomethyl-1-(2-methyl-benzyl)-indan-2-ol

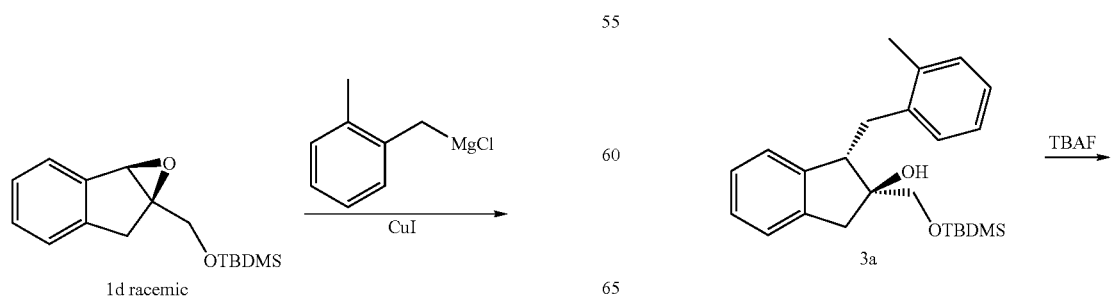

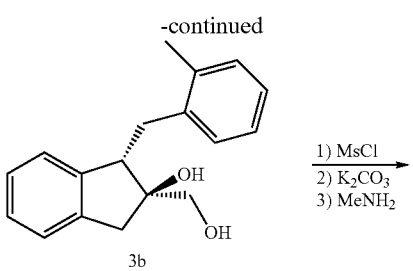

3b

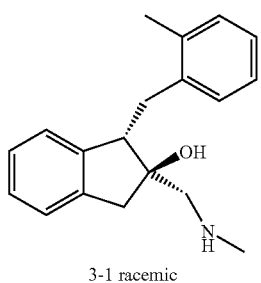

3-1 racemic

Example 3A

Copper (I) iodide (20 mg, 0.11 mmol) was placed in a flask and the flask cooled to −78° C. 2-Methylbenzylmagnesium chloride (0.25 M in THF, 4.2 mL, 1.05 mmol) was added to the flask dropwise. The mixture was allowed to warm up to −40° C., stirred for 15 minutes and treated with a solution of crude 1d (100 mg, 0.35 mmol) in tetrahydrofuran (1 mL) via cannula. This mixture was allowed to warm up to −20° C. over one hour and held at this temperature for 2 hours. The reaction was quenched with a solution of saturated ammonium chloride (2 mL) and extracted with ether (3×10 mL). The combined organic extracts were washed with saturated bicarbonate solution (10 mL), dried over magnesium sulfate and evaporated. Silica gel chromatography using 5-10% ethyl acetate in hexanes gave 3a as a colorless oil (99 mg, 74%).

$^1$H NMR (300 MHz, CDCl$_3$) δ 7.07-7.22 (m, 6H), 6.85-6.95 (m, 2H), 6.20 (d, J=7.5 Hz, 1H), 3.96 (d, J=10.2 Hz, 1H), 3.78 (d, J=9.9 Hz, 1H), 3.33 (dd, J=12.0, 4.5 Hz, 1H), 3.12 (dd, J=12.9, 4.2 Hz, 1H), 3.09 (d, J=16.5 Hz, 1H), 2.88 (d, J=15.5 Hz, 1H), 2.80 (s, 1H), 2.01 (s, 3H), 0.97 (s, 9H), 0.14 (s, 6H). APCI MS m/e: 365.1 ([M+H−H$_2$O]$^+$).

Step 3B

To a solution of 3a (95 mg, 0.25 mmol) in tetrahydrofuran (1.5 mL), tetrabutylammonium fluoride (1.0 M in THF, 0.75 mL, 0.75 mmol) was added. After ten minutes, the reaction was quenched with a solution of saturated ammonium chloride (1 mL) and extracted with ether (3×2 mL). The combined organic extracts were dried over magnesium sulfate, filtered and evaporated. Silica gel chromatography with 50% ethyl acetate in dichloromethane gave 3b (64 mg, 96%).

$^1$H NMR (300 MHz, CDCl$_3$) δ 6.90-7.23 (m, 8H), 6.27 (d, J=7.5 Hz, 1H), 3.98 (d, J=11.4 Hz, 1H), 3.85 (d, J=11.4 Hz, 1H), 3.34 (dd, J=11.4, 5.1 Hz, 1H), 3.19 (d, J=16.2 Hz, 1H), 3.14 (dd, J=12.9, 5.1 Hz, 1H), 2.89 (d, J=16.5 Hz, 1H), 2.01 (s, 3H).

APCI MS m/e: 233.0 ([M+H−2H$_2$O]$^+$).

Step 3C

Alcohol 3b (61 mg, 0.23 mmol) was dissolved in dichloromethane (1.5 mL) and cooled to 0° C. Triethylamine (50 μL, 0.35 mmol) was added to this solution followed by a dropwise addition of methanesulfonyl chloride (20 μL, 0.25 mmol). Stirring was continued at the reduced temperature for one hour. Saturated sodium bicarbonate (1 mL) was added to the reaction mixture and the layers were separated. The aqueous layer was extracted with dichloromethane (2 mL). The combined organic extracts were dried over magnesium sulfate and evaporated. The residue was dissolved in N,N-dimethylformamide (1.5 mL) and treated with potassium carbonate (95 mg, 0.68 mmol). This mixture was stirred at room temperature for 1.5 hours. Methylamine (2 M in THF, 0.57 mL, 1.14 mmol) was then added, and the reaction mixture was heated at 65° C. overnight. After evaporating to half original volume, the reaction mixture was diluted with dichloromethane (10 mL) and washed with saturated sodium bicarbonate solution (5 mL). The organic layer was dried over magnesium sulfate, filtered and evaporated. This crude product was purified on a preparatory HPLC/MS instrument to give the desired product as the trifluoroacetate salt. The free base 3-1 (16 mg) was obtained by dissolving in dichloromethane and neutralizing with saturated aqueous sodium bicarbonate.

$^1$H NMR (300 MHz, CDCl$_3$) δ 6.88-7.23 (m, 8H), 6.28 (d, J=7.8 Hz, 1H), 3.30 (dd, J=11.4, 5.1 Hz, 1H), 3.17 (d, J=15.9 Hz, 1H), 3.01 (dd, J=13.2, 5.1 Hz, 1H), 2.99 (d, J=12.0 Hz, 1H), 2.93 (d, J=16.5 Hz, 1H), 2.89 (d, J=12.0 Hz, 1H), 2.54 (s, 3H), 1.99 (s, 3H). APCI MS m/e: 282.1 ([M+H]$^+$).

Example 4

2-Methylaminomethyl-1-(naphthalen-1-yloxy)-indan-2-ol

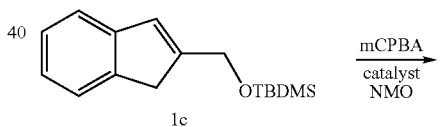

1c

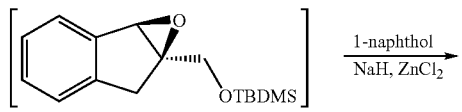

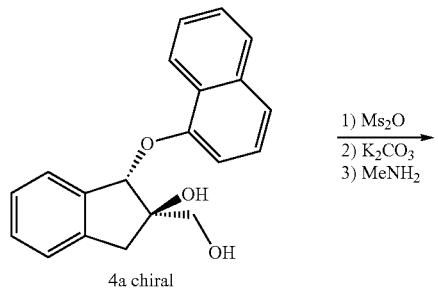

4a chiral

-continued

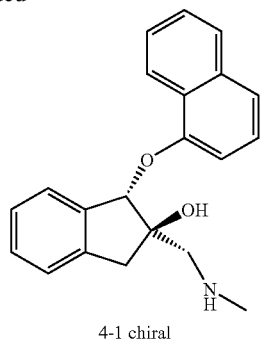

4-1 chiral

Step 4A

To a solution of 1c (200 mg, 0.77 mmol) in dichloromethane (7 mL) at 40° C. to 45° C., was added (1R,2R)-(−)-[1,2-cyclohexanediamino-N,N'-bis(3,5-di-t-butylsalicylidene)]manganese (III) chloride (24 mg, 0.039 mmol) and 4-methylmorpholine N-oxide (450 mg, 3.85 mmol), followed by 3-chloroperoxybenzoic acid (355 mg, 1.54 mmol). The reaction mixture was stirred for three hours at this reduced temperature and treated with dimethylsulfide (0.28 mL, 3.85 mmol). After 20 minutes at 40° C., the mixture was filtered through Celite, washed with a saturated sodium bicarbonate solution (2×5 mL) and dried over magnesium sulfate. Filtration and evaporation gave the crude epoxide. In a separate flask, to sodium hydride (60% dispersion in oil, 92 mg, 2.31 mmol), was added dimethylsulfoxide (5 mL) followed by 1-naphthol (333 mg, 2.31 mmol) in portions. This mixture was stirred with gentle heating until a homogeneous solution was obtained. To this solution, the epoxide intermediate above was added as a solution in dimethyl sulfoxide (1.5 mL), followed by zinc chloride (10 mg, 0.077 mmol). The reaction was allowed to proceed at 75° C. overnight, then treated with saturated brine (50 mL) and extracted with ethyl acetate (3×50 mL). The organic layer was dried over magnesium sulfate, filtered, evaporated and purified by column chromatography on silica gel (10-40% ethyl acetate in hexanes) to give 4a as a brown solid (62 mg, 26%).

$^1$H NMR (300 MHz, CDCl$_3$) δ 8.18 (m, 1H), 7.83 (m, 1H), 7.16-7.54 (m, 9H), 6.04 (s, 1H), 4.19 (d, J=11.4 Hz, 1H), 3.74 (d, J=11.4 Hz, 1H), 3.28 (d, J=16.2 Hz, 1H), 3.19 (s, 1H), 3.15 (d, J=16.2 Hz, 1H), 2.04 (br s, 1H).

Step 4B

To a solution of 4a (61 mg, 0.2 mmol) in dichloromethane (1.5 mL) at −15° C., was added triethylamine (0.05 mL, 0.35 mmol), followed by trifluoromethylsulfonic anhydride (42 mg, 0.24 mmol). After stirring for one hour at this temperature, the mixture was quenched with saturated sodium bicarbonate solution (0.5 mL). The mixture was extracted with dichloromethane (2×1 mL). The organic extracts were combined and dried over magnesium sulfate. The residue obtained after filtration and evaporation was dissolved in N,N-dimethylacetamide (1 mL) and treated with potassium carbonate (83 mg, 0.6 mmol). After an hour at room temperature, methylamine (2.0 M in tetrahydrofuran, 0.5 mL, 1.0 mmol) was added and the mixture was heated at 70° C. for 4 hours. The reaction mixture was filtered, concentrated and the residue purified on a prep. HPLC column to give 4-1 as a yellow oil after basification (26 mg, 41%, 96% ee based on comparison to racemic material on a Chiralcel AD-H column, eluting with 95:5 hexanes/ethanol, containing 0.1% diethylamine at a flow rate of 1 mL per minute).

$^1$H NMR (300 MHz, CDCl$_3$) δ 8.22 (m, 1H), 7.83 (m, 1H), 7.15-7.53 (m, 9H), 5.91 (s, 1H), 3.33 (d, J=12.3 Hz, 1H), 3.22 (d, J=16.2 Hz, 1H), 3.13 (d, J=16.2 Hz, 1H), 2.69 (d, J=12.3 Hz, 1H), 2.41 (s, 3H). APCI MS m/e: 320.1 ([M+H]$^+$).

Example 5

4-Allyloxy-2-methyl-phenol

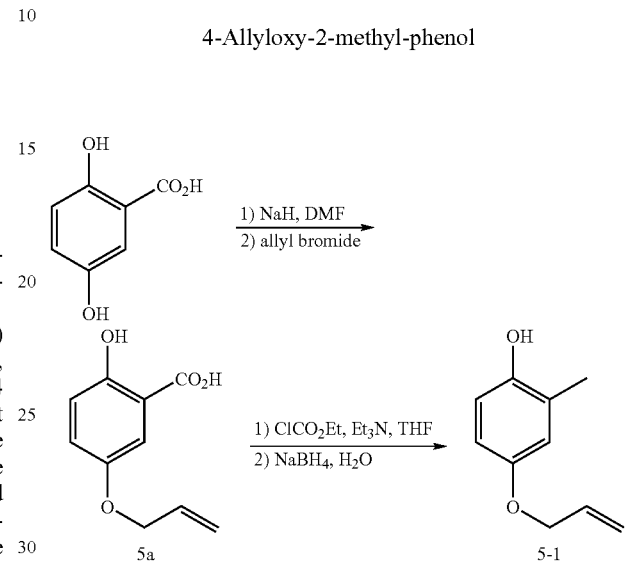

Step 5A

To a suspension of sodium hydride (95%, 3.05 g, 127 mmol) in N,N-dimethylformamide (50 mL), a solution of 2,5-dihydroxybenzoic acid (8.92 g, 58 mmol) in N,N-dimethylformamide (30 mL) was added dropwise. After 2 hours at room temperature, allyl bromide (7.0 g, 57.9 mmol) was added as a solution in N,N-dimethylformamide (15 mL) dropwise. The mixture was stirred for 2 hours at room temperature and then reduced to one third the original volume under vacuum. Water (200 mL) was added and aqueous hydrochloric acid (3 M) was used to adjust the pH to 3. This mixture was extracted with ethyl acetate (3×250 mL). The combined organic extracts were dried over magnesium sulfate, filtered and evaporated to give a tan solid. Recrystallization from acetonitrile gave 5a as cream-colored crystals (7.27 g, 75%).

$^1$H NMR (300 MHz, CDCl$_3$) δ 10.02 (br s, 1H), 7.38 (d, J=3.0 Hz, 1H), 7.18 (dd, J=9.3, 3.0 Hz, 1H), 6.95 (d, J=9.3 Hz, 1H), 5.99-6.11 (m, 1H), 5.42 (dtd, J=17.1, 1.2, 1.2 Hz, 1H), 5.30 (dtd, J=10.5, 1.2, 1.2 Hz, 1H), 4.52 (ddd, J=5.4, 1.2, 1.2 Hz, 2H).

Step 5B

To a solution of 5a (3.0 g, 15.5 mmol) and triethylamine (5.65 mL, 40.3 mmol) in tetrahydrofuran (125 mL) at 0° C. was added ethyl chloroformate (3.84 mL, 40.3 mmol). The mixture was stirred at room temperature for 3 hours. The resulting solid was removed by filtration and washed with tetrahydrofuran (2×25 mL). The filtrate was concentrated under vacuum and redissolved in tetrahydrofuran (45 mL). This solution was added dropwise to a solution of sodium borohydride (4.71 g, 124 mmol) in water (45 mL) at 0° C. The reaction was allowed to proceed at room temperature overnight and neutralized to pH 6 with aqueous hydrochloric acid (3 M). The volatiles were removed under vacuum and the residue extracted with diethyl ether (3×200 mL). The combined organic layers were washed successively with water (150 mL) and brine (150 mL) and dried over magnesium sulfate. Filtration and evaporation followed by silica gel chromatography using 25% ethyl acetate in hexanes as eluent gave 5-1 as a brown oil (2.0 g, 79%).

$^1$H NMR (300 MHz, CDCl$_3$) δ 6.63-6.73 (m, 3H), 5.98-6.01 (m, 1H), 5.39 (dd, J=17.1, 1.8 Hz, 1H), 5.27 (dd, J=10.5, 1.2 Hz, 1H), 4.46-4.49 (m, 2H), 4.41 (br s, 1H), 2.23 (s, 3H). APCI MS m/e: 165.0 ([M+H]$^+$).

Example 6

1-(4-hydroxy-2-methyl-phenoxy)-2-methylaminomethyl-indan-2-ol

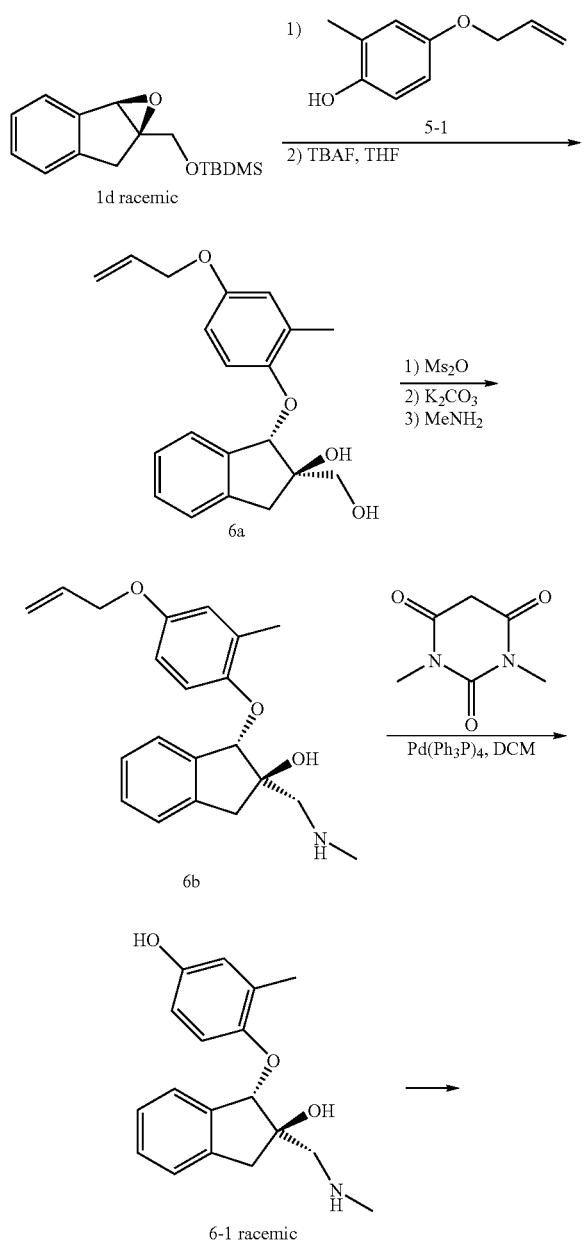

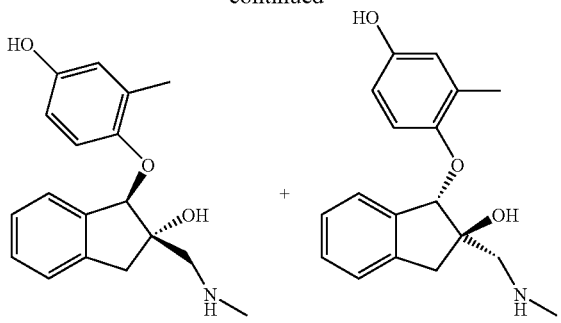

Step 6A

To sodium hydride (60% dispersion in oil, 120 mg, 2.9 mmol) in dimethylsulfoxide (1 mL) at 0° C. was added 5-1 (480 mg, 2.9 mmol). The reaction mixture was heated to 40° C. in a sealed tube for 20 minutes. Epoxide 1d (265 mg, 0.96 mmol) was added as a solution in dimethylsulfoxide (1.0 mL) followed by zinc chloride (26 mg, 0.19 mmol). The resulting mixture was heated at 80° C. overnight. The mixture was then diluted with water (5 mL) and extracted with ethyl acetate (3×5 mL). The organic layer was separated and evaporated to give a brown oil. This residue was dissolved in tetrahydrofuran (1 mL) and treated with a solution of tetrabutylammonium fluoride (1.0 M in tetrahydrofuran, 0.48 mL). After one hour, all volatiles were evaporated and the brown residue was chromatographed on silica gel eluting with 30% ethyl acetate in hexanes to give 6a as a yellow oil (160 mg, 51%).

APCI MS m/e: 291.0 ([M+H]$^+$).

Step 6B

The conversion of 6a to 6b was carried out according to the procedure given in step 1F. Purification of the crude product via silica gel chromatography, using 5% methanol in dichloromethane containing 0.05% triethylamine gave 6b (66 mg, 44%).

APCI MS m/e: 340.1 ([M+H]$^+$).

Step 6C

To a solution of 6b (58 mg, 0.17 mmol) in degassed dichloromethane (25 mL) under an atmosphere of nitrogen was added 1,3-dimethylbarbituric acid (80 mg, 0.5 mmol) and palladium tetrakistriphenylphosphine (39 mg, 0.034 mmol). After 4 hours at 35° C., the volatiles were evaporated and the residue was redissolved in methanol (1 mL). The crude product was purified on a reverse phase HPLC column. The desired fractions were basified with ammonia (7 N in methanol) prior to evaporation. After removal of solvents, the residue was partitioned between saturated sodium bicarbonate solution (5 mL) and ethyl acetate (5 mL). The aqueous layer was further extracted with ethyl acetate (5 mL). The combined organic layers were dried over magnesium sulfate and evaporated to give 6-1 as a yellow oil (24 mg, 47%).

$^1$H NMR (300 MHz, CDCl$_3$) δ 7.22-7.24 (m, 2H), 7.00-7.09 (m, 3H), 6.57-6.60 (m, 2H), 5.45 (s, 1H), 3.27 (d, J=12.3 Hz, 1H), 3.08 (s, 2H), 2.67 (d, J=12.3 Hz, 1H), 2.48 (s, 3H), 2.00 (s, 3H). APCI MS m/e: 300.0 ([M+H]$^+$).

Step 6D

The enantiomerically pure compounds 6-2 and 6-3 (3.4 mg each, 52% recovery), were obtained from racemic 6-1 (13 mg) by chiral prep. HPLC using a Chiralcel OD-H column eluting with 95:5 hexanes/isopropyl alcohol containing 0.1% diethylamine at a flow rate of 15 mL/min.

The following compounds were made according to this procedure using compound 22-1.

| No. | | —NR$_2$R$_3$ | W | Stereochem | MW | MH$^+$ | t$_R$ (method) |
|---|---|---|---|---|---|---|---|
| 6-4 | 2-CH$_3$-3-OH-phenyl | —N(H)CH$_3$ | O | R,S and S,R | 299.4 | 300.0 | 3.21 (2) |
| 6-5 | 2-CH$_3$-3-OH-phenyl | —N(H)CH$_3$ | O | R,S | 299.4 | 300.0 | 3.30 (2) |
| 6-6 | 2-CH$_3$-3-OH-phenyl | —N(H)CH$_3$ | O | S,R | 299.4 | 300.0 | 3.32 (2) |

Example 7

3-Methylaminomethyl-4-o-tolyloxy-chroman-3-ol

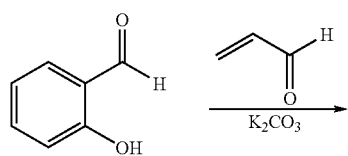

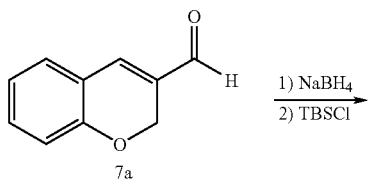
7a

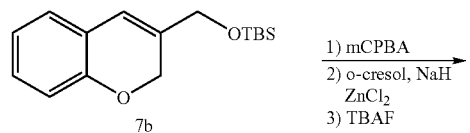
7b

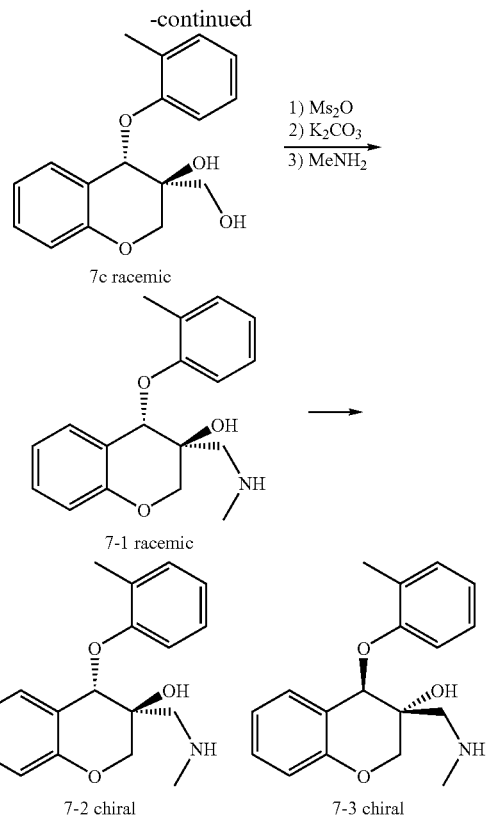

Step 7A

To a suspension of salicylaldehyde (6.10 g, 50 mmol) and potassium carbonate (6.90 g, 50 mmol) in 1,4-dioxane (100 mL) was added acrolein (5.2 mL, 78 mmol). The mixture was heated at 100° C. for 1 hour. Water (100 mL) was added and the mixture was extracted with ether (3×100 mL). The combined organics were dried over magnesium sulfate and evaporated. Silica gel chromatography of the crude material using 25% ether in hexanes as eluent gave 7a as a yellow solid (7.17 g, 90%)

Step 7B

Aldehyde 7a (7.17 g, 44.8 mmol) was dissolved in ethanol (100 mL) and treated with sodium borohydride (1.7 g, 44.8 mmol). After 15 minutes, the solvent was evaporated and the residue was quenched with aqueous hydrochloric acid (1 M, 50 mL) and water (50 mL) and extracted with ether (3×100 mL). The combined organic extracts were washed with brine (2×50 mL) and dried over magnesium sulfate. Evaporation gave the crude alcohol (7.2 g), which was dissolved in dichloromethane (80 mL) and treated with 4-dimethylaminopyridine (270 mg, 2.2 mmol), triethylamine (12.2 mL, 88 mmol) and tert-butyldimethylchlorosilane (7.64 g, 51 mmol). After 2 hours of stirring at room temperature, the reaction mixture was concentrated under vacuum and purified via silica gel chromatography using 15% ethyl acetate in hexanes to give 7b as a white solid (10.7 g, 86% over 2 steps).

$^1$H NMR (300 MHz, CDCl$_3$) δ 7.08 (dt, J=8.1, 1.8 Hz, 1H), 6.98 (dd, J=6.9, 1.2 Hz, 1H), 6.86 (app t, J=7.5 Hz, 1H), 6.78 (d, J=7.8 Hz, 1H), 6.34 (s, 1H), 4.75 (s, 2H), 4.21 (s, 2H), 0.92 (s, 9H), 0.10 (s, 6H).

Step 7C

Sodium bicarbonate (6.07 g, 72.3 mmol) and 7b (8.00 g, 28.9 mmol) were suspended in dry dichloromethane (400 mL) and cooled to 0° C. To this mixture was added 3-chloroperoxybenzoic acid (75%, 9.23 g, 40.5 mmol) with mechanical stirring over 5 minutes. The reaction was allowed to proceed at this temperature for 5 hours. The solid was filtered out and washed with dichloromethane (3×20 mL). The filtrate was washed with saturated sodium bicarbonate solution (100 mL) and dried over magnesium sulfate. Evaporation of volatiles gave the epoxide intermediate as an oil. In a separate flask, dimethylsulfoxide (120 mL) was added to sodium hydride (60% dispersion in oil, 3.4 g, 87 mmol) followed by o-cresol (9.0 mL, 87 mmol). The mixture was gently heated at 40° C. until a yellow solution was obtained. This solution was cooled to room temperature and treated with a solution of the epoxide intermediate above in dimethylsulfoxide (20 mL). Zinc chloride (1 M in tetrahydrofuran, 5.8 mL) was added next and the mixture was stirred at 80° C. overnight. The reaction mixture was diluted with water (350 mL) and extracted with ethyl acetate (4×150 mL). The combined organic layers were washed with saturated sodium bicarbonate solution (200 mL), dried over magnesium sulfate and evaporated. The residue was dissolved in tetrahydrofuran (100 mL) and treated with tetra-N-butylammonium fluoride (1 M in tetrahydrofuran, 40 mL). After 1.5 hours of stirring at room temperature, excess solvent was removed and the crude material was subjected to flash column chromatography on silica gel using 25-60% ethyl acetate in hexanes as eluent. 7c was thus obtained as a pale yellow oil (4.11 g, 50%).

$^1$H NMR (300 MHz, CDCl$_3$) δ 7.15-7.23 (m, 3H), 7.09-7.12 (m, 1H), 6.91-6.97 (m, 3H), 6.79 (dt, J=7.2, 1.2 Hz, 1H), 5.17 (s, 1H), 4.39 (d, J=11.4 Hz, 1H), 4.19 (dd, J=11.4, 1.5 Hz, 1H), 4.02 (dd, J=11.4, 5.1 Hz, 1H), 3.83 (dd, J=12.0, 7.2 Hz, 1H), 2.78 (s, 1H), 2.22 (t, J=6.6 Hz, 1H), 1.97 (s, 3H).

Step 7D

The conversion of 7c to 7-1 was carried out according to the procedure given in step 1F. The crude product was dissolved in ether and treated with 1.2 equivalents of 2 M hydrochloric acid in ether. After 5 minutes of stirring, the precipitate was filtered off and triturated successively with ether and isopropyl alcohol. The precipitate was then suspended in 0.5 N aqueous sodium hydroxide solution and the suspension extracted with dichloromethane three times. The combined organic extracts were washed with brine and dried over magnesium sulfate. Evaporation yielded 7-1 as a white solid (3.34 g, 80%).

$^1$H NMR (300 MHz, CDCl$_3$) δ 6.78-6.95 (m, 3H), 7.04-7.26 (m, 5H), 5.26 (s, 1H), 4.23 (d, J=11.1 Hz, 1H), 4.13 (d, J=11.4 Hz, 1H), 3.08 (d, J=12.9 Hz, 1H), 2.76 (d, J=12.6 Hz, 1H), 2.49 (s, 3H), 2.07 (s, 3H). APCI MS m/e: 300.1 ([M+H]$^+$).

Step 7E

The enantiomerically pure compounds 7-2 and 7-3 (2.1 g each, 93% recovery), were obtained from racemic 7-1 (4.5 g) by chiral preparative SFC using a Chiralpak OD-H column eluting with 25% methanol containing 0.5% N,N-dimethylethylamine at a flow rate of 50 mL/min (100 bar, 35° C.).

The following compounds were made according to this procedure.

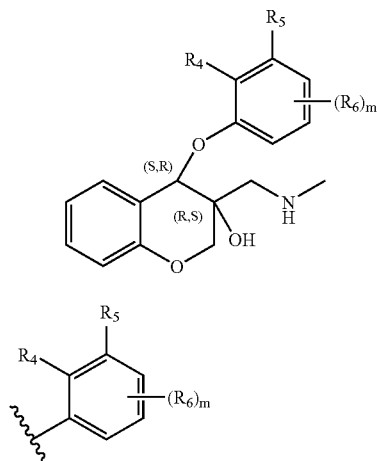

| No. | | Stereochem | MW | MH$^+$ | $t_R$ (method) |
|---|---|---|---|---|---|
| 7-1 | 2-CH$_3$-phenyl | R,R and S,S | 299.4 | 300.1 | 4.40 (2) |
| 7-2 | 2-CH$_3$-phenyl | R,R | 299.4 | 300.0 | 4.53 (2) |
| 7-3 | 2-CH$_3$-phenyl | S,S | 299.4 | 300.2 | 15.35 (3) |
| 7-4 | 2-Cl-phenyl | R,R and S,S | 319.8 | 320.0 | 4.11 (2) |
| 7-5 | 2-Cl-phenyl | R,R | 319.8 | 320.0 | 4.20 (2) |
| 7-6 | 2-Cl-phenyl | S,S | 319.8 | 320.0 | 4.21 (2) |
| 7-7 | 2,3-di-CH$_3$-phenyl | R,R and S,S | 313.4 | 314.1 | 4.57 (2) |
| 7-8 | 2,3-di-CH$_3$-phenyl | S,S | 313.4 | 314.1 | 4.62 (2) |
| 7-9 | 2,3-di-CH$_3$-phenyl | R,R | 313.4 | 314.1 | 4.63 (2) |
| 7-10 | 2,4-di-CH$_3$-phenyl | R,R and S,S | 313.4 | 314.2 | 7.67 (5) |
| 7-11 | 2-CH$_3$-4-F-phenyl | R,R and S,S | 317.4 | 318.7 | 7.21 (5) |
| 7-12 | 2-CH$_3$-3-F-phenyl | R,R and S,S | 317.4 | 318.0 | 4.61 (2) |
| 7-13 | 2,4-di-CH$_3$-phenyl | R,R | 313.4 | 314.1 | 4.69 (2) |
| 7-14 | 2,4-di-CH$_3$-phenyl | S,S | 313.4 | 314.1 | 16.80 (3) |
| 7-15 | 2-CH$_3$-4-F-phenyl | R,R | 317.4 | 318.0 | 4.24 (2) |
| 7-16 | 2-CH$_3$-4-F-phenyl | S,S | 317.4 | 318.0 | 4.25 (2) |
| 7-17 | 2-CH$_3$-5-F-phenyl | R,R and S,S | 317.4 | 318.0 | 4.69 (2) |

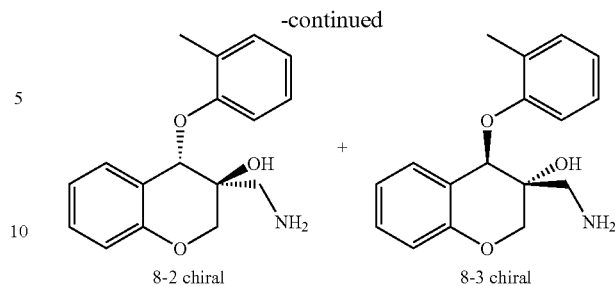

| No. | | Stereochem | MW | MH+ | $t_R$ (method) |
|---|---|---|---|---|---|
| 7-18 | 2-CH$_3$-4-OH-phenyl | R,R and S,S | 315.4 | 316.1 | 3.30 (2) |
| 7-19 | 2-CH$_3$-4-OH-phenyl | R,R | 315.4 | 316.0 | 3.36 (2) |
| 7-20 | 2-CH$_3$-4-OH-phenyl | S,S | 315.4 | 316.0 | 3.36 (2) |
| 7-21 | 4-Br-2-CH$_3$-phenyl | R,R and S,S | 378.3 | 377.9 | 4.92 (2) |
| 7-22 | 2-Ethyl-phenyl | R,R and S,S | 313.4 | 314.1 | 4.68 (2) |
| 7-23 | 2-CH$_3$O-phenyl | R,R and S,S | 315.4 | 315.6 | 8.04 (2) |
| 7-24 | 4-Br-2-CH$_3$-phenyl | R,R | 378.3 | 377.9 | 5.48 (2) |
| 7-25 | 4-Br-2-CH$_3$-phenyl | S,S | 378.3 | 377.9 | 5.47 (2) |

Example 8

3-aminomethyl-4-o-tolyloxy-chroman-3-ol

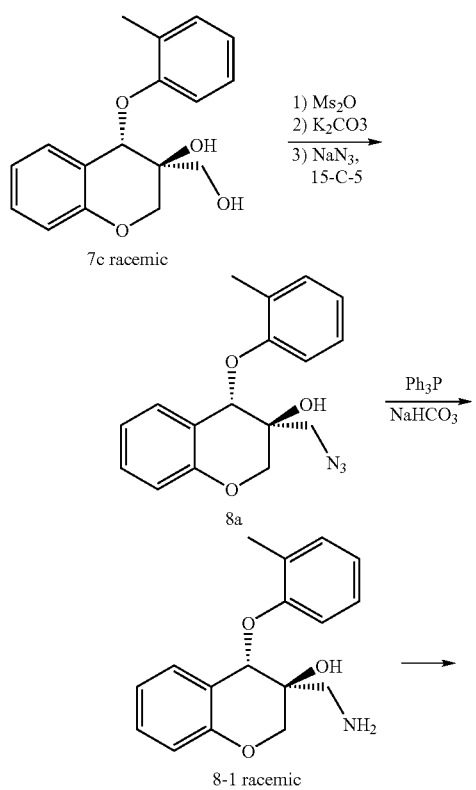

Step 8A

To a solution of 7c (250 mg, 0.87 mmol) in anhydrous dichloromethane (3 mL) at 0° C. was added methanesulfonic anhydride (165 mg, 0.96 mmol), followed by N,N-diisopropylethylamine (0.18 mL, 1.09 mmol). The mixture was stirred for one hour at 0° C. and diluted to 10 mL with dichloromethane. This solution was washed successively with water (3 mL) and saturated sodium bicarbonate solution (3 mL). The organic layer was dried over magnesium sulfate and evaporated. The residue was dissolved in N,N-dimethylacetamide (4 mL) and treated with potassium carbonate (362 mg, 2.62 mmol). After stirring for 2 hours at room temperature, sodium azide (284 mg, 4.37 mmol) and 15-crown-5 (0.035 mL, 0.17 mmol) were added and the mixture was heated at 70° C. overnight. Water (10 mL) was added to quench and the mixture was extracted with dichloromethane (3×20 mL). The combined organic layers were washed with brine (10 mL) and dried over magnesium sulfate. After evaporation, the crude product was purified on a silica gel column eluting with 20% ethyl acetate in hexanes to give 8a as a pale yellow oil (255 mg, 94%).

$^1$H NMR (300 MHz, CDCl$_3$) δ 7.09-7.24 (m, 4H), 6.88-6.98 (m, 3H), 6.79 (dt, J=7.5, 1.2 Hz, 1H), 5.16 (s, 1H), 4.37 (d, J=11.4 Hz, 1H), 4.14 (dd, J=11.4, 1.5 Hz, 1H), 3.82 (d, J=12.3 Hz, 1H), 3.62 (d, J=12.6 Hz, 1H), 2.44 (s, 1H), 1.93 (s, 3H).

APCI MS m/e: 295.1 ([M+H–H$_2$O]$^+$).

Step 8B

Triphenylphosphine (322 mg, 1.223 mmol) was added to a solution of 8a (255 mg, 0.82 mmol) in tetrahydrofuran. After 3 hours at room temperature, water (0.33 mL) and sodium bicarbonate (70 mg, 0.83 mmol) were added to the reaction mixture. The reaction mixture was stirred for 24 hours at room temperature. After evaporating the volatiles, the residue was diluted with water (5 mL) and extracted with dichloromethane (3×5 mL). The combined organic extracts were dried over magnesium sulfate and evaporated. The crude product was purified on a prep. HPLC column. The target fractions were evaporated to give the trifluoroacetate salt of the desired product, which was partitioned between saturated sodium bicarbonate solution (20 mL) and ethyl acetate (20 mL). The aqueous layer was further extracted with ethyl acetate (2×20 mL). The combined organic layers were dried over magnesium sulfate and evaporated to give 8-1 as a colorless oil (115 mg, 49%).

$^1$H NMR (300 MHz, CD$_3$OD) δ 7.26 (d, J=7.8 Hz, 1H), 7.15-7.21 (m, 2H), 7.06 (d, J=7.5 Hz, 1H), 6.84-6.92 (m, 3H), 6.69 (dt, J=7.5, 0.9 Hz, 1H), 5.12 (s, 1H), 3.33 (d, J=11.4 Hz, 1H), 4.14 (dd, J=11.4, 1.2 Hz, 1H), 3.04 (d, J=13.8 Hz, 1H), 2.88 (d, J=13.5 Hz, 1H), 1.89 (s, 3H).

APCI MS m/e: 286.2 ([M+H]$^+$).

Step 8C

The enantiomerically pure compounds 8-2 and 8-3 (30 mg each, 54% recovery), were obtained from racemic 8-1 (110 mg) by chiral preparative HPLC using a Chiralpak AD-H column eluting with 9:1 hexanes/ethanol containing 0.1% diethylamine at a flow rate of 15 mL/min. The following compounds were made according to this procedure.

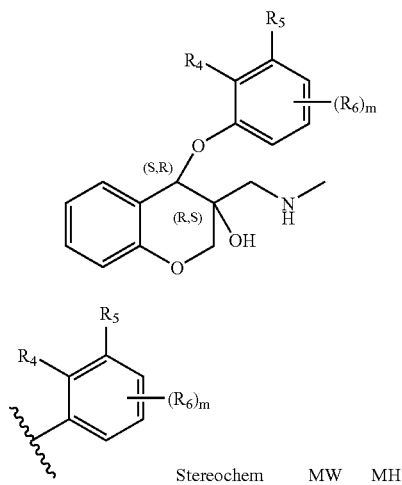

| No. | | Stereochem | MW | MH+ | $t_R$ (method) |
|---|---|---|---|---|---|
| 8-1 | 2-CH$_3$-phenyl | R,R and S,S | 285.3 | 285.8 | 7.33 (5) |
| 8-2 | 2-CH$_3$-phenyl | S,S | 285.3 | 286.0 | 4.33 (2) |
| 8-3 | 2-CH$_3$-phenyl | R,R | 285.3 | 286.2 | 7.43 (5) |
| 8-4 | 2-Cl-phenyl | R,R and S,S | 305.8 | 306.0 | 4.26 92) |
| 8-5 | 2,4-di-CH$_3$-phenyl | R,R and S,S | 299.4 | 300.0 | 4.59 (2) |
| 8-6 | 2-CH$_3$-4-F-phenyl | R,R and S,S | 303.3 | 304.0 | 4.53 (2) |
| 8-7 | 2-Cl-phenyl | R,R | 305.8 | 306.0 | 4.01 (2) |
| 8-8 | 2-Cl-phenyl | S,S | 305.8 | 306.0 | 4.02 (2) |
| 8-9 | 2,4-di-CH$_3$-phenyl | R,R | 299.4 | 300.1 | 8.10 (5) |
| 8-10 | 2,4-di-CH$_3$-phenyl | S,S | 299.4 | 300.1 | 8.11 (5) |
| 8-11 | 2-CH$_3$-4-F-phenyl | R,R | 303.3 | 304.0 | 7.70 (5) |
| 8-12 | 2-CH$_3$-4-F-phenyl | S,S | 303.3 | 303.8 | 7.70 (5) |

Example 9

3-Fluoro-2-Methylphenol

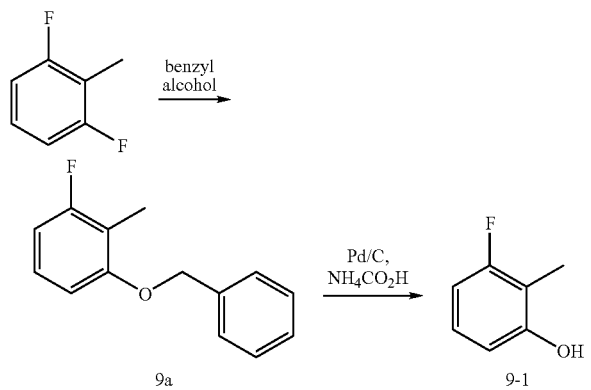

Step 9A

To sodium hydride (60% in mineral oil, 7.2 g, 180 mmol) in N,N-dimethylacetamide (120 mL) under a nitrogen atmosphere was added benzyl alcohol (12 mL, 117 mmol) and the mixture was stirred for 60 min at ambient temperature. 2,6-Difluorotoluene (15.0 g, 117 mmol) was added and the resultant mixture was stirred at 70° C. for 16 h. The mixture was cooled to ambient temperature and was partitioned between de-ionized water (300 mL) and ethyl acetate (300 mL). The aqueous layer was extracted with ethyl acetate (300 mL) and the combined organics were washed with saturated aqueous sodium chloride (2×200 mL), dried over magnesium sulfate, filtered and concentrated in vacuo to afford 9a which was used in the next step without further purification.

Step 9B

Palladium on carbon (10 wt. %, 50% wet, 7.5 g, 3.5 mmol) was added to benzyl ether 9a (12.2 g, 57 mmol) and ammonium formate (16.0 g, 250 mmol) in ethanol (150 mL). The mixture was stirred at 90° C. for 3 h, cooled to ambient temperature, filtered through celite and concentrated in vacuo. The residue was purified by silica gel chromatography eluting with 0 to 10% ethyl acetate in hexanes to afford 9-1 as a colorless oil (5.6 g, 79%). $^1$H NMR (300 MHz, CDCl$_3$) δ 7.00 (m, 1H), 6.61 (m, 2H), 5.11 (br s, 1H), 2.16 (d, J=2.1 Hz, 1H).

Example 10

2-Fluoro-6-Methylphenol

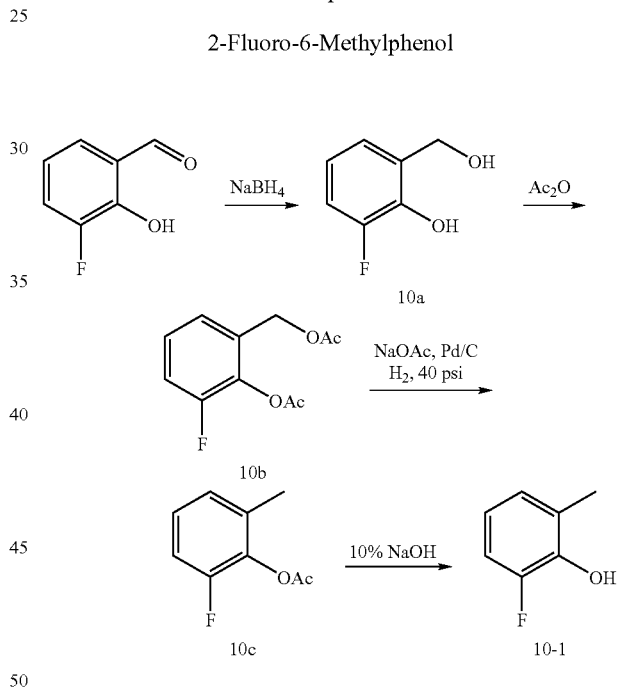

Step 10A

To 3-fluoro-2-hydroxybenzaldehyde (5.0 g, 35.7 mmol) in methanol (100 mL) at 0° C. was added sodium borohydride (1.5 g, 39.3 mmol) portionwise. The mixture was stirred at 0° C. for 1 h then warmed to ambient temperature and concentrated in vacuo. The residue was partitioned between 0.5 M aqueous hydrochloric acid (100 mL) and ethyl acetate (100 mL). The aqueous layer was extracted with ethyl acetate (100 mL) and the combined organics were dried over magnesium sulfate, filtered and concentrated in vacuo to afford 10a (5.1 g, quant.) as a pale yellow oil. $^1$H NMR (300 MHz, CDCl$_3$) δ 7.03 (m, 1H), 6.93 (m, 1H), 6.82 (m, 1H), 6.54 (br s, 1H), 5.16 (br s, 1H), 4.84 (s, 2H).

Step 10B

To 10a (2.5 g, 17.6 mmol) was added acetic anhydride (8.3 mL, 88 mmol). The mixture was stirred under reflux conditions (external oil bath temperature 150° C.) for 16 h. The mixture was cooled to ambient temperature and the residue was diluted with ethyl acetate (100 mL) and then was washed with saturated aqueous sodium hydrogen carbonate (2×75 mL). The organic layer was dried over magnesium sulfate, filtered and concentrated in vacuo to afford 10b (4.2 g, 70% pure, 75%) as a brown oil which was used in the next step without further purification. $^1$H NMR (300 MHz, CDCl$_3$) δ 7.10-7.23 (m, 3H), 5.08 (s, 2H), 2.36 (s, 3H), 2.07 (s, 3H).

Step 10C

To 10b (4.7 g, 20.8 mmol) in methanol (20 mL) was added sodium acetate (2.6 g, 31 mmol) and palladium on carbon (10 wt. %, 0.25 g, 2.4 mmol). The mixture was shaken on a Parr hydrogenator under 40 psi of hydrogen gas for 16 h. The mixture was filtered through Celite and the filtrate was concentrated in vacuo. The residue was purified by silica gel chromatography eluting with 10% ethyl acetate in hexanes to afford 10c (3.0 g, 63%) as a colorless oil.

Step 10D

To acetate 10c (3.2 g, 20 mmol) was added 10% aqueous sodium hydroxide (10 mL, 25 mmol) and the mixture was stirred under reflux conditions for 90 min. Methanol (10 mL) was added and the mixture was stirred under reflux conditions for a further 2 h. The mixture was cooled to ambient temperature and concentrated in vacuo to remove the methanol. The residue was acidified to pH 2 by the dropwise addition of 1 M aqueous hydrochloric acid (25 mL). The aqueous phase was extracted with ethyl acetate (2×100 mL) and the combined organics were washed with de-ionized water (50 mL), dried over magnesium sulfate, filtered and concentrated in vacuo to afford 10-1 (1.46 g, 58%) as a yellow oil. $^1$H NMR (300 MHz, CDCl$_3$) δ 6.92 (m, 2H), 6.74 (m, 1H), 5.10 (br. s, 1H), 2.28 (s, 3H).

Example 11

1-(4-Fluoro-2-methyl-phenoxy)-2-methylaminomethyl-indan-2-ol

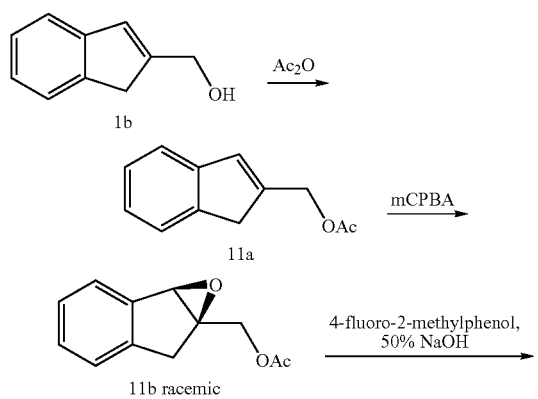

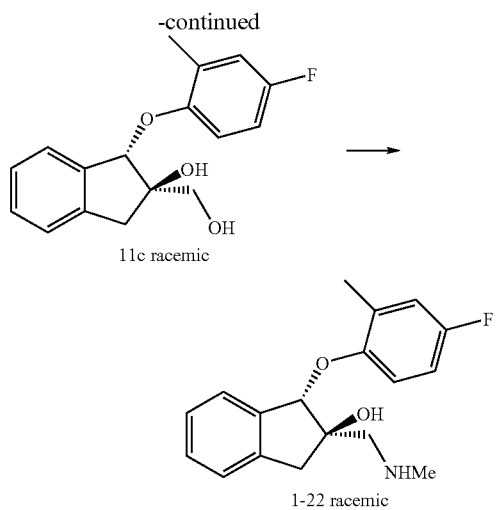

Step 11A

To 1b (10.0 g, 68.5 mmol) in triethylamine (25 mL) was added acetic anhydride (8.4 g, 82.2 mmol) and dimethylaminopyridine (0.8 g, 6.9 mmol). The mixture was stirred at ambient temperature for 3 h then concentrated in vacuo. The residue was partitioned between dichloromethane (100 mL) and saturated aqueous sodium bicarbonate (100 mL). The aqueous phase was extracted with dichloromethane (100 mL) then the combined organics were washed with saturated aqueous sodium chloride (100 mL), dried over magnesium sulfate, filtered and concentrated in vacuo. The residue was purified by silica gel chromatography eluting with 15% ethyl acetate in hexanes to afford 11a as a colorless syrup (12.0 g, 93%). $^1$H NMR (300 MHz, CDCl$_3$) δ 7.43 (d, J=6.9 Hz, 1H), 7.36 (d, J=6.9 Hz, 1H), 7.27 (t, J=6.9 Hz, 1H), 7.18 (td, J=6.9 and 1.5 Hz, 1H), 6.81 (br s, 1H), 5.02 (s, 2H), 3.43 (s, 2H), 2.12 (s, 3H).

Step 11B

To 11a (10.0 g, 53.1 mmol) in diclomethane (1 L) was added sodium bicarbonate (11.24 g, 133 mmol). The mixture was cooled to 0° C. and m-chloroperbenzoic acid was added slowly. Stirring was continued at 0° C. for a further 3 h then the mixture was allowed to warm to ambient temperature overnight. The mixture was filtered and the precipitate was rinsed with cold dichloromethane (2×100 mL). The filtrate was washed with de-ionized water (500 mL) and saturated aqueous sodium chloride (500 mL). The aqueous was back extracted with dichloromethane (200 mL) and the combined organics were dried over magnesium sulfate, filtered and concentrated in vacuo. The residue was purified by silica plug filtration (30% ethyl acetate in hexanes) to afford a 11b as a yellow oil (10.85 g, quant.). $^1$H NMR (300 MHz, CDCl$_3$) δ 7.48 (d, J=6.9 Hz, 1H), 7.17-7.30 (m, 3H), 4.66 (d, J=12.3 Hz, 1H), 4.37 (d, J=12.3 Hz, 1H), 4.26 (br s, 1H), 3.24 (d, J=18.0 Hz, 1H), 3.04 (d, J=18.0 Hz, 1H), 2.14 (s, 3H).

Step 11C

Aqueous sodium hydroxide (50%, 5.1 mL, 63.7 mmol) and acetonitrile (100 mL) were combined in a screw cap pressure vessel. 4-Fluoro-2-methylphenol (5.1 g, 63.7 mmol) was added and the resultant mixture was stirred at ambient temperature for 10 minutes then at 70° C. for 15 min. The epoxide 11b (10.85 g, 53.1 mmol) in acetonitrile (50 mL) was then added and the flask was sealed and heated at 70° C. for 16 h. The mixture was cooled to ambient temperature and the residue was filtered, the cake was washed with isopropyl acetate (150 mL). The filtrate was concentrated in vacuo and redissolved in isopropyl acetate (300 mL). The solution was washed with 2M aqueous sodium hydroxide (2×150 mL) and saturated aqueous sodium chloride (2×150 mL). The organic layer was dried over magnesium sulfate, filtered and concentrated in vacuo to afford a brown/yellow oil. The oil was purified by silica gel chromatography eluting with 10 to 40% ethyl acetate in hexanes to afford 11c as a white solid (7.0 g, 46%). $^1$H NMR (300 MHz, CDCl$_3$) δ 7.26 (m, 2H), 7.14 (m, 3H), 6.88 (m, 2H), 5.65 (s, 1H), 4.09 (dd, J=11.4 and 4.5 Hz, 1H), 3.70 (dd, J=11.4 and 8.0 Hz, 1H), 3.19 (d, J=16.2 Hz, 1H), 3.09 (s, 1H), 3.06 (d, J=16.2 Hz, 1H), 2.26 (dd, J=8.0 and 4.5 Hz, 1H), 2.10 (s, 3H). APCI MS m/e: 253.0 ([M+H−2H$_2$O]$^+$).

Step 11D

Diol 11c was converted to the amine 1-22 according to step 1F using N,N-dimethylacetamide in place of N,N-dimethylformamide. $^1$H NMR (300 MHz, CDCl$_3$) δ 7.17-7.29 (m, 3H), 7.11 (t, J=7.2 Hz, 1H), 7.02 (d, J=7.5 Hz, 1H), 6.80-6.90 (m, 2H), 5.54 (s, 1H), 3.35 (d, J=12.3 Hz, 1H), 3.15 (br. s, 2H), 2.98 (d, J=12.3 Hz, 1H), 2.60 (s, 3H), 2.00 (s, 3H). APCI MS m/e: 302.0 ([M+H−2H$_2$O]$^+$).

Example 12

(1S,2R)-1-(3-fluoro-2-methyl-phenoxy)-2-methylaminomethyl-indan-2-ol

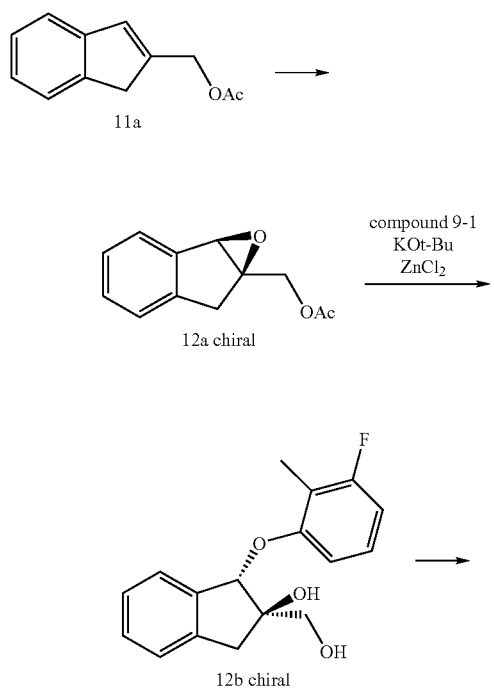

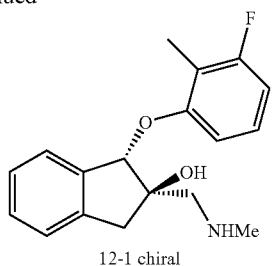

12-1 chiral

Step 12A

To 11a (6.0 g, 31.9 mmol) in dichloromethane (75 mL) was added (1R,2R)-(−)-[1,2-cyclohexanediamino-N,N'-bis(3,5-di-t-butylsalicylidene)]manganese (III) chloride (1.8 g, 2.8 mmol) and 4-(3-phenylpropyl)pyridine N-oxide (3.0 g, 14.0 mmol). The mixture was cooled to 0° C. In a separate flask at 0° C., saturated aqueous disodium hydrogen phosphate (3 mL) was added to sodium hypochlorite solution (75 mL, 12.7%) and this mixture was transferred to the previous flask with vigorous stirring and the mixture was allowed to reach ambient temperature over 16 h. De-ionized water (50 mL) was added with stirring and the mixture was filtered through Celite washing with dichloromethane (2×30 mL). The layers were separated and the aqueous was extracted with dichloromethane (2×75 mL). The combined organics were washed with de-ionized water (2×200 mL) and saturated sodium chloride solution (2×200 mL), dried over magnesium sulfate and concentrated in vacuo. The residue was purified by silica gel chromatography eluting with 0 to 20% ethyl acetate in hexanes to afford 12a as a brown oil (3.45 g, 53%) which crystallized on standing at −10° C.

Step 12B

To phenol 9-1 (4.5 g, 34 mmol) in N,N-dimethylacetamide (40 mL) under a nitrogen atmosphere was added potassium t-butoxide (4.2 g, 37 mmol) and the mixture was stirred for 15 min to obtain an almost homogeneous solution. In a separate flask zinc dichloride (4.3 mL, 1M in diethylether, 4.3 mmol) was added to epoxide 12a (chiral) in N,N-dimethylacetamide (60 mL). To this mixture was added the phenoxide solution and the resultant mixture was stirred at 80° C. for 17 h. Aqueous 10% sodium hydroxide (50 mL) was added and stirring was continued at 80° C. for a further 1 h. The mixture was cooled to ambient temperature and partitioned between de-ionized water (150 mL) and ethyl acetate (300 mL). The aqueous layer was extracted with ethyl acetate (4×100 mL) and the combined organics were washed with saturated aqueous sodium chloride (3×100 mL). The organic layer was dried over magnesium sulfate, filtered and concentrated in vacuo. The residue contained a large amount of N,N-dimethylacetamide and was dissolved in ethyl acetate (400 mL) and extracted with de-ionized water (4×100 mL). The organic layer was washed with saturated aqueous sodium chloride (200 mL), dried over magnesium sulfate, filtered and concentrated in vacuo. The residue was purified by silica gel chromatography eluting with 0 to 25% ethyl acetate in hexanes to afford 12b as a white solid (3.0 g, 60%). $^1$H NMR (300 MHz, CDCl$_3$) δ

7.22-7.32 (m, 2H), 7.11-7.21 (m, 3H), 7.07 (d, J=8.4 Hz, 1H), 6.75 (t, J=8.7 Hz, 1H), 5.77 (s, 1H), 4.09 (dd, J=11.4 and 3.6 Hz, 1H), 3.69 (dd, J=11.4 and 7.5 Hz, 1H), 3.19 (d, J=16.2 Hz, 1H), 3.08 (d, J=16.2 Hz, 1H), 2.15 (dd, J=7.5 and 3.6 Hz, 1H), 2.07 (d, J=2.4 Hz, 1H). APCI MS m/e: 271.0 ([M+H−H$_2$O]$^+$).

Step 12C

Diol 12b was converted to the amine 12-1 according to step 1F using diisopropylamine in place of triethylamine and N,N-dimethylacetamide in place of N,N-dimethylformamide. $^1$H NMR (300 MHz, CDCl$_3$) δ 7.08-7.28 (m, 6H), 6.72 (m, 1H), 5.66 (s, 1H), 3.26 (d, J=12.3 Hz, 1H), 3.16 (d, J=16.2 Hz, 1H), 3.09 (d, J=16.2 Hz, 1H), 2.78 (d, J=12.3 Hz, 1H), 2.52 (s, 3H), 2.05 (d, J=1.8 Hz, 3H). APCI MS m/e: 302.0 ([M+H−2H$_2$O]$^+$).

Example 13

2-Methylaminomethyl-1-o-chloro-m-phenoxy-indan-2-ol

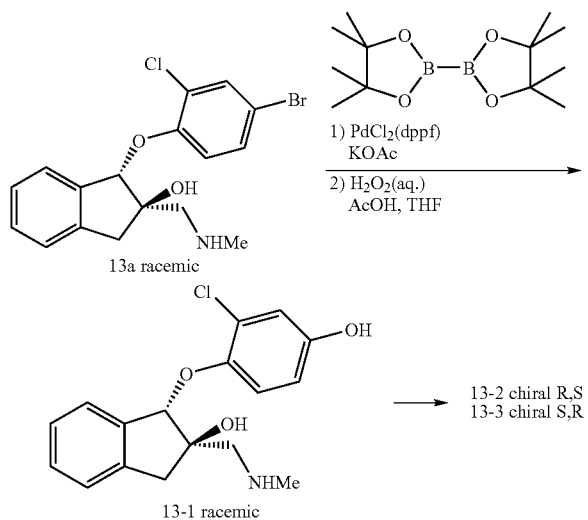

Step 13A

A solution of bromide 13a (70 mg, 0.18 mmol, synthesized from 1d following the procedures for steps 1E and 1F) in dimethylsulfoxide (1 mL) was degassed with a stream of nitrogen for 5 min. To this solution was added bis(pinacolato)diboron (70 mg, 0.28 mmol), dichloro[1,1'-bis(diphenylphosphino)ferrocene]palladium II dichloromethane adduct (15 mg, 0.02 mmol) and potassium acetate (53 mg, 0.54 mmol) and the resultant mixture was stirred in a sealed tube at 90° C. for 3 h. The mixture was cooled to ambient temperature and partitioned between de-ionized water (5 mL) and ethyl acetate (5 mL). The aqueous layer was extracted with ethyl acetate (2×5 mL) and the combined organics were dried over magnesium sulfate, filtered and concentrated in vacuo. The residue was dissolved in tetrahydrofuran (1 mL) and acetic acid (24 μL, 0.43 mmol) and 30% aqueous hydrogen peroxide (37 μL, 0.36 mmol) was added. The resultant mixture was shaken at ambient temperature for 16 h then concentrated in vacuo. The residue was dissolved in 2 mL methanol and purified by preparative HPLC. The collected fractions were neutralized by the addition of 2 drops triethylamine and were concentrated in vacuo. The residue was partitioned between saturated aqueous sodium hydrogen carbonate (5 mL) and ethyl acetate (10 mL). The aqueous layer was extracted with ethyl acetate (10 mL) and the combined organics were dried over magnesium sulfate, filtered and concentrated in vacuo to afford 13-1 (20 mg, 35%) as a colorless oil.

$^1$H NMR (300 MHz, CDCl$_3$) δ 7.10-7.30 (m, 7H), 5.56 (s, 1H), 3.34 (d, J=12.3 Hz, 1H), 3.17 (d, J=15.9 Hz, 1H), 3.02 (d, J=15.9 Hz, 1H), 2.72 (d, J=12.3 Hz, 1H), 2.54 (s, 3H). APCI MS m/e: 320.0 ([M+H]$^+$).

Step 13B

The enantiomerically pure compounds, 13-2 and 13-3 were obtained from 13-1 by chiral preparative HPLC using a Chiralpak AS-H column eluting with 95:5 hexanes/ethanol with 0.1% diethylamine.

Example 14

2-Methylaminomethyl-1-o-tolyloxy-tetralin-2-ol

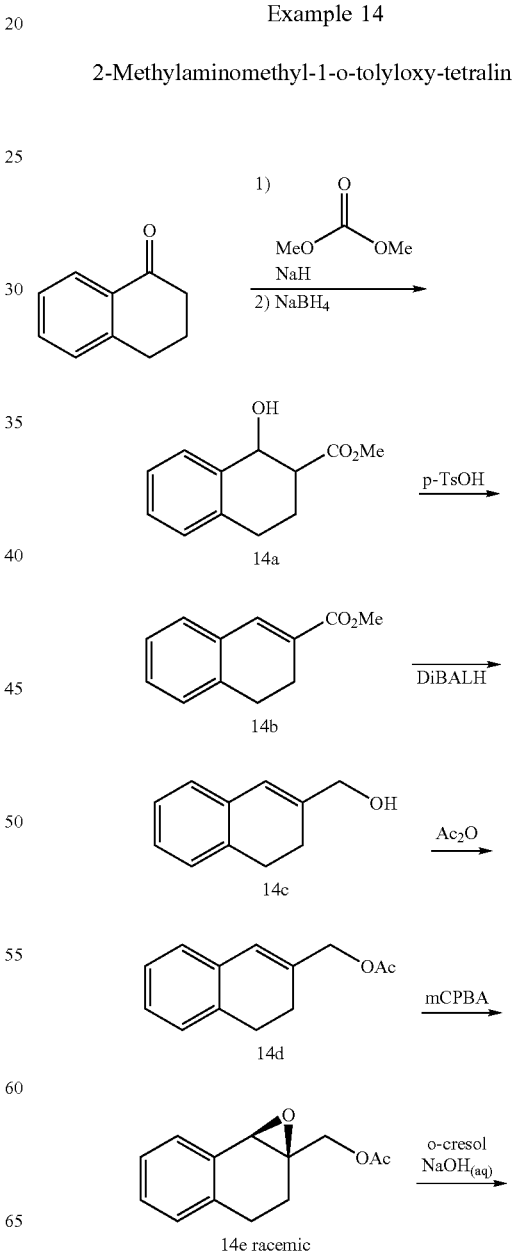

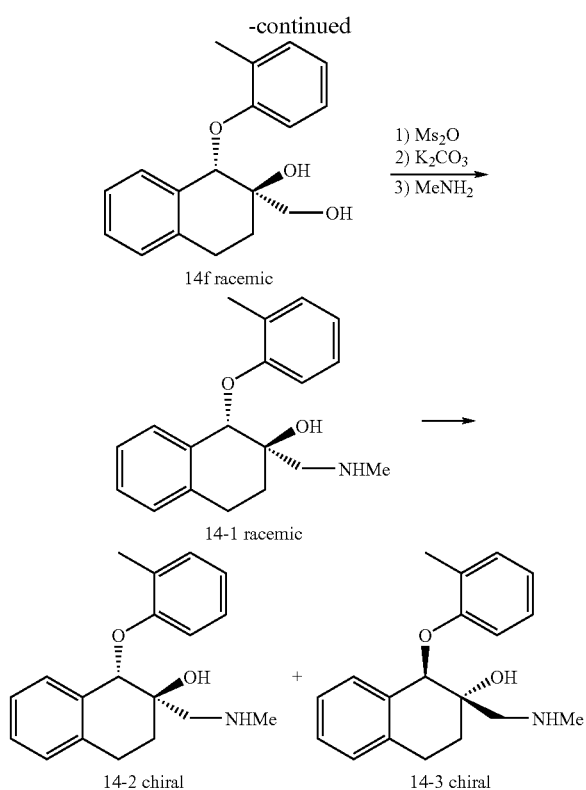

Step 14A

To a suspension of sodium hydride (60% in mineral oil, 4.08 g, 0.17 mol) and dimethylcarbonate (34.6 mL, 0.41 mol) in toluene (50 mL) at 60° C. was added alpha-tetralone (10.0 g, 0.07 mol) in toluene (50 mL) dropwise. The mixture was stirred at 60° C. for 16 h during which time it became a purple solid. The reaction was cooled to ambient temperature and was diluted with toluene (200 mL) and de-ionized water (100 mL). The aqueous layer was extracted with toluene (2×200 mL) and the organic layers were collected, dried over magnesium sulfate, filtered and concentrated in vacuo to afford a brown oil. Crystallization from hexanes afforded yellow crystals (5.6 g, 27.5 mmol) which were dissolved in methanol (30 mL) and stirred at 0° C. in an ice water bath. Sodium borohydride (1.45 g, 38.4 mmol) was added portionwise and the reaction was allowed to warm to ambient temperature over 5 h. The mixture was concentrated in vacuo and diluted with de-ionized water (20 mL). The aqueous was extracted with ethyl acetate (3×100 mL) and the organic layers were collected, dried over magnesium sulfate, filtered and concentrated in vacuo. The residue was purified by flash chromatography eluting with 25% ethyl acetate in hexanes to afford a mixture of the cis and trans alcohol 14a as a white solid (2.63 g, 46%). $^1$H NMR (300 MHz, CDCl$_3$) δ 7.06-7.64 (m, 4H), 5.05 (m, 1H), 3.78 (s, 3H), 2.68-3.00 (m, 4H), 2.05-2.30 (m, 2H).

APCI MS m/e: 189.0 ([M+H−H$_2$O]$^+$).

Step 14B

To a solution of alcohol 14a (2.63 g, 12.8 mmol) in toluene (30 mL) was added p-toluenesulfonic acid monohydrate (0.14 g, 0.71 mmol). The mixture was stirred under reflux conditions for 3 h then cooled to ambient temperature and diluted with dichloromethane (100 mL). The mixture was washed with de-ionized water (15 mL) and the organics were dried over magnesium sulfate, filtered and concentrated in vacuo to afford unsaturated ester 14b (2.25 g, 93%) as a colorless oil. $^1$H NMR (300 MHz, CDCl$_3$) δ 7.53 (s, 1H), 7.10-7.28 (m, 4H), 3.82 (s, 3H), 2.87 (m, 2H), 2.61 (m, 2H).

APCI MS m/e: 189.0 ([M+H]$^+$).

Step 14C

To a solution of ester 14b (2.25 g, 12.0 mmol) in diethyl ether (30 mL) at −78° C. (acetone/dry ice bath) was added diisobutylaluminum hydride (1 M in hexanes, 12.0 mL, 12.0 mmol). The mixture was stirred and allowed to reach ambient temperature over 16 h. The mixture was again cooled to −78° C. (acetone/dry ice bath) and further portions of diisobutylaluminum hydride (1 M in hexanes, 11.0 mL, 11.0 mmol) were added and the mixture was stirred and allowed to reach ambient temperature over 16 h. The mixture was cooled to 0° C. (ice/water bath) and quenched with de-ionized water (50 mL). The aqueous was diluted with 50% aqueous sodium hydroxide solution (10 mL) and extracted with diethyl ether (3×150 mL). The combined organics were dried over magnesium sulfate, filtered and concentrated in vacuo to afford unsaturated alcohol 14c as a yellow oil (1.71 g, 89%). $^1$H NMR (300 MHz, CDCl$_3$) δ 7.02-7.20 (m, 4H), 6.46 (br. s, 1H), 4.25 (s, 2H), 2.85 (t, J=7.8 Hz, 2H), 2.31 (t, J=7.8 Hz, 2H).

Step 14D

To a solution of unsaturated alcohol 14c (1.71 g, 10.7 mmol) in triethylamine (3 mL) was added acetic anhydride (1.42 mL, 12.8 mmol). The mixture was stirred at ambient temperature over 64 h then concentrated in vacuo and diluted with dichloromethane (50 mL). The solution was washed with saturated aqueous sodium hydrogen carbonate (10 mL), dried over magnesium sulfate, filtered and concentrated in vacuo. The residue was purified by silica gel chromatography eluting with 25% ethyl acetate in hexanes to afford acetate 14d as a yellow oil (1.58 g, 74%). $^1$H NMR (300 MHz, CDCl$_3$) δ 7.02-7.20 (m, 4H), 6.46 (br. s, 1H), 4.68 (s, 2H), 2.86 (t, J=8.1 Hz, 2H), 2.31 (t, J=8.1 Hz, 2H), 2.13 (s, 3H). APCI MS m/e: 143.0 ([M+H−AcOH]$^+$).

Step 14E

To a solution of acetate 14d (0.21 g, 1.1 mmol) in dichloromethane (5 mL) was added solid sodium hydrogen carbonate (0.21 g, 2.5 mmol). The mixture was stirred and cooled to 0° C. (ice/water bath) and m-chloroperbenzoic acid (0.22 g, 1.3 mmol) was added. The mixture was stirred at that temperature for 6 h and was quenched by the addition of saturated aqueous sodium hydrogen carbonate (5 mL). The resultant mixture was warmed to ambient temperature and the aqueous was extracted with dichloromethane (3×30 mL). The combined organics were dried over magnesium sulfate, filtered and concentrated in vacuo to afford epoxide 14e (0.22 g, quant.). $^1$H NMR (300 MHz, CDCl$_3$) δ 7.39 (m, 1H), 7.16-7.32 (m, 2H), 7.11 (d, J=9.0 Hz, 1H), 4.48 (d, J=12.0 Hz, 1H), 4.22 (d, J=12.0 Hz, 1H), 3.83 (s, 1H), 2.84 (m, 1H), 2.61 (m, 1H), 2.35 (m, 1H), 2.13 (s, 3H), 1.83 (m, 2H). EIMS m/e: 218.0 (M$^+$).

Step 14F

To a solution of o-cresol (0.27 mL, 2.6 mmol) in acetonitrile (1 mL) was added sodium hydroxide (97 mg, 2.44 mmol) in de-ionized water (97 μL) and the resultant mixture was heated at 50° C. for 20 mins. A solution of the acetate 14e (507 mg, 2.3 mmol) in acetonitrile (1.5 mL) was added and the mixture was heated at 50° C. for a further 2 h then at 70° C. for 16 h. Aqueous 1M sodium hydroxide (2 mL) was added and the mixture was stirred for a further 24 h at 70° C. The solution was cooled to ambient temperature and diluted with ethyl acetate (30 mL). The mixture was washed with saturated aqueous sodium chloride (10 mL) and the aqueous washings were extracted with ethyl acetate (2×30 mL). The combined organics were dried over magnesium sulfate, filtered and concentrated in vacuo. The residue was purified by silica gel chromatography eluting with 30% ethyl acetate in hexanes to afford diol 14f as a yellow oil (0.43 g, 65%). $^1$H NMR (300 MHz, CDCl$_3$) δ 7.07-7.26 (m, 6H), 6.91 (m, 1H), 5.33 (s, 1H), 4.00 (dd, J=11.3 and 4.8 Hz, 1H), 3.60 (dd, J=11.3 and 7.4 Hz, 1H), 3.00 (m, 2H), 2.16 (m, 2H), 1.97 (m, 1H), 1.56 (s, 3H). APCI MS m/e: 249.0 ([M+H−2H$_2$O]$^+$).

Step 14G

A solution of diol 14f (195 mg, 0.69 mmol) in dichloromethane (2 mL) was cooled to −40° C. (dry ice bath). Triethylamine (137 μL, 1.03 mmol) and methanesulfonic anhydride (240 mg, 1.38 mmol) were added and the reaction mixture was allowed to gradually reach ambient temperature over 16 h. The mixture was diluted with dichloromethane (30 mL) and washed with saturated aqueous sodium hydrogen carbonate (10 mL). The combined organics were dried over magnesium sulfate, filtered and concentrated in vacuo to afford a yellow foam. The yellow foam was dissolved in N,N-dimethylformamide (3 mL) and the solution was transferred to a sealable flask. Potassium carbonate (295 mg, 2.1 mmol) was added and the mixture was stirred at ambient temperature for 2 h. Methylamine (2M in tetrahydrofuran, 1.72 mL, 3.44 mmol) was added and the mixture was stirred at 70° C. in the sealed vessel for 16 h. Ethyl acetate (20 mL) was added and the resultant mixture was washed with saturated aqueous sodium hydrogen carbonate (8 mL). The aqueous washings were extracted with ethyl acetate (2×20 mL) and the combined organics were dried over magnesium sulfate, filtered and concentrated in vacuo. The residue was purified by silica gel chromatography eluting with 5% methanol in dichloromethane containing 0.01% triethylamine to afford amine 14-1 as a yellow oil (72 mg, 35%). $^1$H NMR (300 MHz, CDCl$_3$) δ 7.02-7.26 (m, 6H), 6.90 (m, 1H), 5.27 (s, 1H), 2.70-3.10 (m, 4H), 2.46 (s, 3H), 2.11 (s, 3H), 1.90-2.20 (m, 2H). APCI MS m/e: 298.1 ([M+H]$^+$).

Step 14H

The enantiomerically pure compounds 14-2 and 14-3 (23 mg each, 64% recovery) were obtained from racemic 14-1 (72 mg) by chiral preparative HPLC using Chiralcel OD-H (20×250 cm) column eluting with 95:5 hexanes/isopropyl alcohol with 0.1% diethylamine at a flow rate of 15 mL/min.

Example 15

2-Methylaminomethyl-1-o-tolyloxy-indan-2-ol

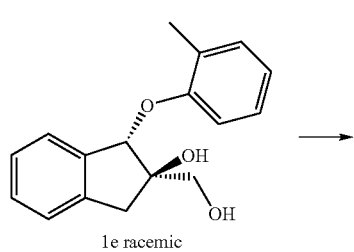

1e racemic

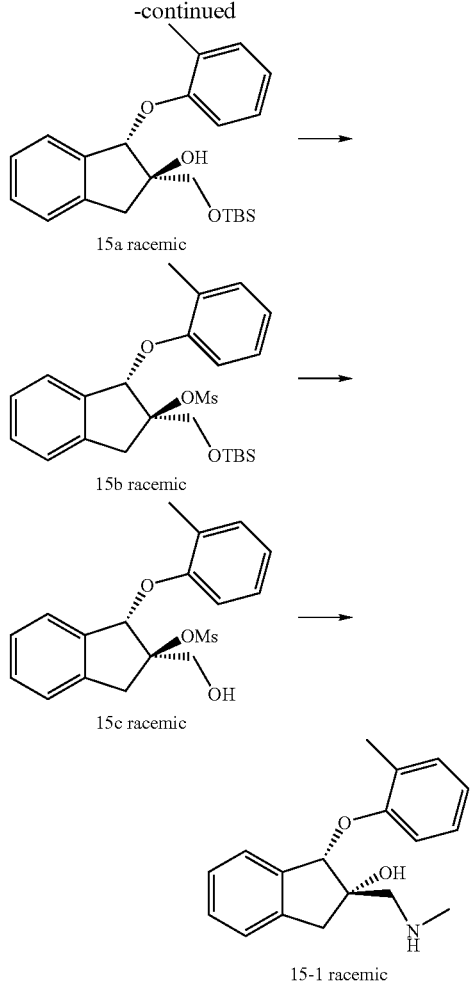

Step 15A

To a solution of 1e (1.0 g, 3.7 mmol) and triethylamine (0.57 mL, 4.1 mmol) in dichloromethane (20 mL) at 0° C. was added tert-butyldimethylsilyl chloride (1.81 g, 12.0 mmol). The mixture was allowed to warm to ambient temperature over 16 h and was concentrated in vacuo. The residue was purified by flash chromatography eluting with 5% ethyl acetate in hexanes to afford 15a (0.71 g, 50%) as a yellow oil. $^1$H NMR (300 MHz, CDCl$_3$) δ 7.12-7.33 (m, 7H), 6.90 (dt, J=7.2 and 0.9 Hz, 1H), 5.68 (s, 1H), 4.02 (d, J=10.0 Hz, 1H), 3.67 (d, J=10.0 Hz, 1H), 3.29 (d, J=15.9 Hz, 1H), 3.20 (br. s, 1H), 2.97 (d, J=15.9 Hz, 1H), 2.14 (s, 3H), 0.89 (s, 9H), 0.05 (s, 3H), 0.15 (s, 3H).

APCI MS m/e: 253.0 ([M+H−H$_2$O−TBS]$^+$).

Step 15B

To a solution of 15a (0.71 g, 1.8 mmol) and triethylamine (1.28 mL, 9.2 mmol) in dichloromethane (20 mL) at 0° C. was added methanesulfonyl chloride (0.72 mL, 9.2 mmol). The mixture was stirred at 0° C. for 30 min and then was allowed to warm to ambient temperature over 18 h. The mixture was concentrated in vacuo and the residue was purified by flash chromatography eluting with 10% ethyl acetate in hexanes to afford 15b (0.18 g, 21%) as a yellow oil. $^1$H NMR (300 MHz, CDCl$_3$) δ 6.90-7.33 (m, 7H), 6.93 (m, 1H), 6.18 (s, 1H), 4.30 (d, J=12.0 Hz, 1H), 4.04 (d, J=12.0 Hz, 1H), 3.70 (d, J=16.5 Hz, 1H), 3.62 (d, J=16.5 Hz, 1H), 3.07 (s, 3H), 2.15 (s, 3H), 0.87 (s, 9H), 0.03 (s, 3H), 0.02 (s, 3H). APCI MS m/e: 367.1 ([M+H-MsOH]$^+$).

Step 15C

To a solution of 15b (0.15 g, 0.33 mmol) in tetrahydrofuran (10 mL) was added tetra-butyl ammonium fluoride (1.0 M in tetrahydrofuran, 0.33 mL, 0.33 mmol). The mixture was stirred at ambient temperature for 1 h and was then concentrated in vacuo. The residue was dissolved in ethyl acetate (20 mL) and was washed with saturated aqueous sodium hydrogen carbonate (20 mL) and brine (20 mL). The organics were dried over magnesium sulfate, filtered and concentrated in vacuo. The residue was purified by flash chromatography eluting with 10 to 20% ethyl acetate in hexanes to afford 15c (0.073 g, 63%) as a yellow oil. $^1$H NMR (300 MHz, CDCl$_3$) δ 7.16-7.35 (m, 7H), 6.97 (dt, J=7.5 and 1.5 Hz, 1H), 6.14 (s, 1H), 4.33 (d, J=13.8 Hz, 1H), 4.13 (d, J=13.8 Hz, 1H), 3.63 (s, 2H), 3.13 (s, 3H), 2.19 (s, 3H). APCI MS m/e: 235.0 ([M+H-MsOH-H$_2$O]$^+$).

Step 15D

To a solution of 15c (73 mg, 0.21 mmol) in N,N-dimethylacetamide (2 mL) was added sodium hydride (60% in mineral oil, 15 mg, 0.63 mmol). The mixture was stirred at ambient temperature for 1.5 h. Dimethylamine (2.0 M in tetrahydrofuran, 0.52 mL, 1.1 mmol) was added and the mixture was heated at 55° C. for 18 h. The residue was dissolved in ethyl acetate (20 mL) and then was washed with saturated aqueous sodium hydrogen carbonate (20 mL) and brine (20 mL). The organics were dried over magnesium sulfate, filtered and concentrated in vacuo. The residue was purified by preparative HPLC to afford 1-4 (4 mg, 7%) as a yellow oil. $^1$H NMR (300 MHz, CDCl$_3$) δ 7.16-7.35 (m, 7H), 6.94 (m, 1H), 5.55 (s, 1H), 4.40 (d, J=16.2 Hz, 1H), 3.21 (s, 2H), 3.10 (d, J=16.2 Hz, 1H), 2.71 (s, 3H), 2.07 (s, 3H). APCI MS m/e: 284.1 ([M+H]$^+$).

Example 16

5-Methoxy-2-methylaminomethyl-1-o-tolyloxy-indan-2-ol

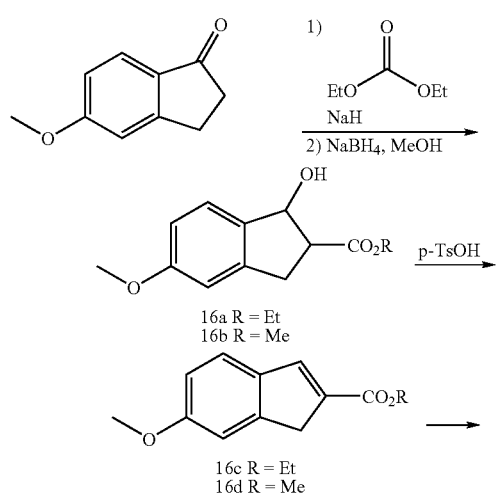

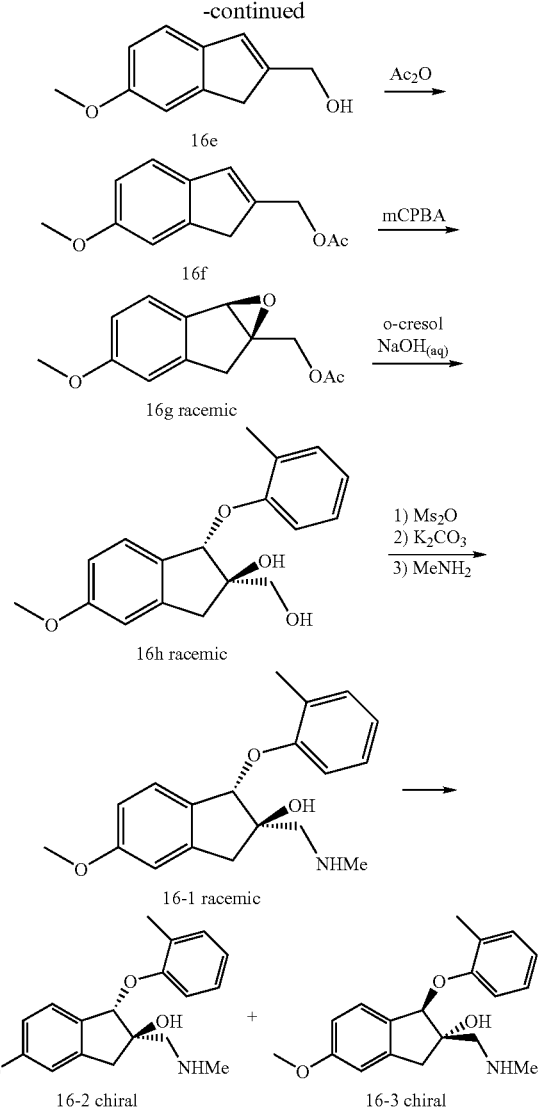

Step 16A

5-Methoxy-1-indanone was converted to a mixture of 16a and 16b (arising from transesterification in the ketone reduction step) following the procedure for step 14A using diethyl carbonate in place of dimethyl carbonate. The crude alcohols, 16a and 16b, were used in the next step without purification.

Step 16B

Alcohols 16a and 16b were converted to esters 16c and 16d following the procedure for step 14B. Silica gel chromatography eluting with 15% ethyl acetate in hexanes gave 16d followed by 16c. For 16d: $^1$H NMR (300 MHz, CDCl$_3$) δ 7.66 (m, 1H), 7.41 (d, J=8.4 Hz, 1H), 7.07(m, 1H), 6.88 (dd, J=8.4 and 2.4 Hz, 1H), 3.85 (s, 3H), 3.83 (s, 3H), 3.65 (m, 2H). APCI MS m/e: 205.0 ([M+H]$^+$). For 16c: $^1$H NMR (300 MHz, CDCl$_3$) δ 7.66 (m, 1H), 7.41 (d, J=8.4 Hz, 1H), 7.06 (m, 1H), 6.88 (dd, J=8.4 and 2.1 Hz, 1H), 4.28 (q, J=7.0 Hz, 2H), 3.85 (s, 3H), 3.65 (m, 2H), 1.35 (t, J=7.0 Hz, 3H). APCI MS m/e: 219.0 ([M+H]$^+$).

Step 16C

Ester 16c or 16d was converted to 16e following procedure 14C. $^1$H NMR (300 MHz, CDCl$_3$) δ 7.22 (m, 1H), 7.03 (m, 1H), 6.81 (m, 1H), 6.68 (m, 1H), 4.54 (m, 2H), 3.82 (s, 3H), 3.41 (m, 2H). APCI MS m/e: 159.0 ([M+H–H$_2$O]$^+$).

Step 16D

Alcohol 16e was converted to 16f following procedure 14D. APCI MS m/e: 159.0 ([M+H–AcOH]$^+$).

Step 16E

Alkene 16f was converted to 16g following procedure 14E.

Step 16F

Epoxide 16g was converted to diol 16 h following procedure 14F. $^1$H NMR (300 MHz, CDCl$_3$) δ 7.11-7.24 (m, 4H), 6.94 (td, J=6.9 and 1.8 Hz, 1H), 6.82 (dd, J=8.1 and 2.4 Hz, 1H), 6.71 (d, J=2.1 Hz, 1H), 5.76 (s, 1H), 4.06-4.15 (m, 3H), 3.79 (m, 1H), 3.70 (s, 3H), 3.64 (m, 1H), 3.05 (d, J=5.7 Hz, 1H), 2.20 (s, 3H). APCI MS m/e: 283.0 ([M+H–H$_2$O]$^+$).

Step 16G

Diol 16h was converted to amine 16-1 following procedure 14G. The crude product was purified by preparative HPLC. The pure fractions were combined using ethyl acetate (10 mL) which was washed with 0.5M aqueous sodium hydroxide (10 mL). The organic layer was evaporated and co-evaporated with toluene (3×5 mL) to afford amine 16-1 as the free base. $^1$H NMR (300 MHz, CDCl$_3$) δ 7.10-7.30 (m, 4H), 6.91 (m, 1H), 6.80 (dd, J=8.1 and 2.7 Hz, 1H), 6.75 (d, J=2.1 Hz, 1H), 5.62 (s, 1H), 3.70 (s, 3H), 2.31 (d, J=12.3 Hz, 1H), 3.08 (d, J=15.5 Hz, 1H), 2.96 (d, J=15.5 Hz, 1H), 2.58 (d, J=12.3 Hz, 1H), 2.45 (s, 3H), 2.19 (s, 3H). APCI MS m/e: 314.0 ([M+H]$^+$).

Step 16H

The enantiomerically pure compounds 16-2 and 16-3 (9.5 mg each, 63% recovery) were obtained from racemic 16-1 (30 mg) by chiral preparative HPLC using Chiralpak OD-H (20×250 cm) column eluting with 90:10 hexanes/ethyl alcohol with 0.1% diethylamine at a flow rate of 15 mL/min.

Example 17

2-Methylaminomethyl-1-o-tolyloxy-indan-2-ol

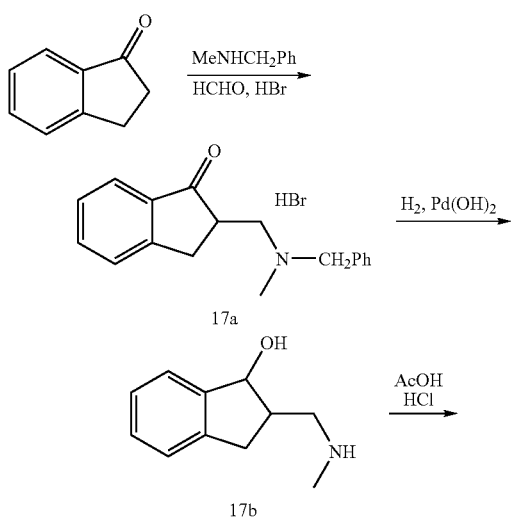

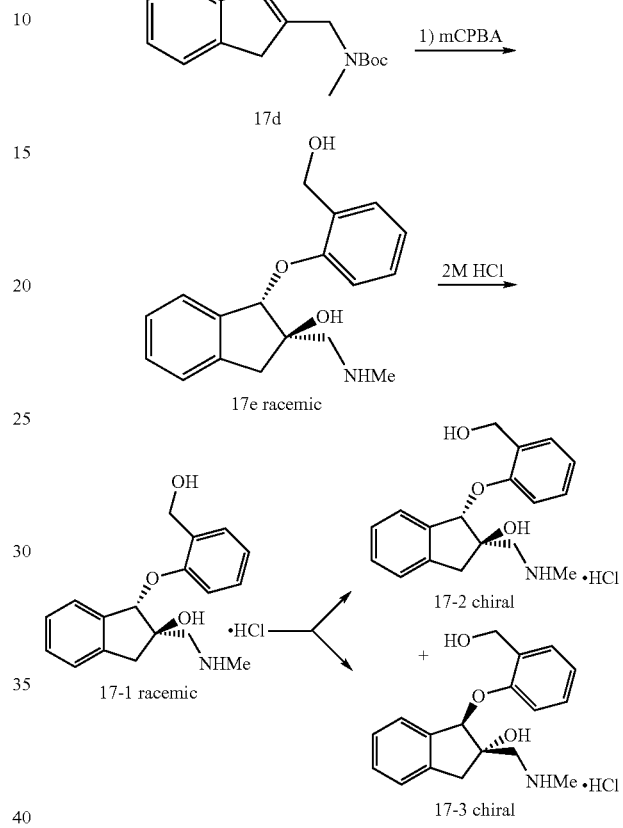

Step 17A

To N-methylbenzylamine (10.0 g, 83 mmol) in acetonitrile (125 mL) at 0° C. was added hydrobromic acid (48%, 19 g, 113 mmol). 1-Indanone (10.0 g, 68 mmol) and paraformaldehyde (3.5 g, 118 mmol) were added next and the mixture was heated under reflux conditions for 3 hours. The mixture was concentrated in vacuo, diluted with acetonitrile (100 mL) and cooled at 5° C. for 2 hours. Ether (30 mL) was added to this mixture and after 30 minutes, the resulting solid was filtered out and rinsed with more ether. Amine 17a was thus obtained as a white solid (10 g, 43%) which was contaminated with N-methylbenzylamine. APCI MS m/e: 266.0 ([M+H]$^+$).

Step 17B

A suspension of amine 17a (3.0 g, 8.8 mmol), palladium hydroxide on carbon (20% wt., 50% wet, 1.17 g, 0.88 mmol) and ethanol (30 mL) was stirred at 40 p.s.i. under a H$_2$ atmosphere for 16 h. The reaction mixture was filtered through celite, washed with ethanol (50 mL) and concentrated in vacuo to give 17b (approx. 85% pure, 2.18 g, 96%). APCI MS m/e: 178.1 ([M+H]$^+$).

Step 17C

To alcohol 17b (approx. 85% pure, 2.18 g, 8.46 mmol) was added acetic acid (24 mL) followed by concentrated hydrochloric acid (10 mL). The reaction mixture was heated at 70° C. for 3 h, cooled to ambient temperature and concentrated in vacuo. The residue was diluted with ethyl acetate (60 mL) and carefully basified with 50% aqueous sodium hydroxide. The aqueous layer was extracted with ethyl acetate (3×60 mL). The combined organic extracts were dried over magnesium sulfate, filtered and concentrated in vacuo to give 17c (approx. 85% pure, 1.12 g, 83%). $^1$H NMR (300 MHz, CDCl$_3$) δ 7.10-7.44 (m, 4H), 6.69 (br. s, 1H), 3.66 (s, 2H), 3.40 (s, 2H), 2.50 (s, 3H). APCI MS m/e: 160.0 ([M+H]$^+$).

Step 17D

To amine 17c (approx. 85% pure, 1.12 g, 7.04 mmol) and triethylamine (2.8 mL, 21.1 mmol) in dichloromethane (10 mL) was added di-tert-butyldicarbonate (1.67 g, 7.75 mmol). The reaction mixture was stirred at ambient temperature for 16 h and then diluted with dichloromethane (30 mL). The mixture was washed with 0.1 M aqueous hydrochloric acid (30 mL). The organics were dried over magnesium sulfate, filtered and concentrated in vacuo. The residue was purified by silica gel chromatography eluting with 25% ethyl acetate in hexanes to give 17d (1.48 g, 81%). $^1$H NMR (300 MHz, CDCl$_3$) δ 7.10-7.44 (m, 4H), 6.66 (br. s, 1H), 4.25 (s, 2H), 3.33 (s, 2H), 2.87 (s, 3H), 1.49 (s, 9H). APCI MS m/e: 160.1 ([M+H-Boc]$^+$).

Step 17E

Alkene 17d was converted to alcohol 17e following procedures 14E and 14F. $^1$H NMR (300 MHz, CDCl$_3$) δ 7.96 (t, J=1.8 Hz, 1H), 7.87 (dt, J=7.5 and 1.2 Hz, 1H), 7.49 (m, 1H), 7.41 (d, J=7.5 Hz, 1H), 7.36 (d, J=7.5 Hz, 1H), 7.31 (d, J=7.5 Hz, 1H), 7.25 (t, J=7.5 Hz, 1H), 7.15 (t, J=7.5 Hz, 1H), 6.64 (s, 1H), 4.26 (br. s, 2H), 3.30 (s, 2H), 2.87 (br. s, 3H), 1.60 (s, 2H), 1.50 (s, 9H). APCI MS m/e: 300.0 ([M+H-Boc]$^+$).

Step 17F

A solution of 17e (34 mg, 0.09 mmol) in diethyl ether (2 mL) was cooled to 0° C. (ice bath) and hydrochloric acid (2.0M in diethyl ether, 0.5 mL, 0.25 mmol) was added. Stirring was continued at 0° C. for 10 minutes then the solution was allowed to warm to ambient temperature. The mixture was then stirred at 40° C. for a further 16 h and was concentrated in vacuo. The residue was recrystallized from hot ethyl acetate (5 mL) containing 2 drops isopropyl alcohol. The precipitate was filtered under reduced pressure and washed with diethyl ether (2×5 mL) to afford 17-1 (11 mg, 52%) as a white solid. $^1$H NMR (300 MHz, CDCl$_3$) δ 7.08-7.34 (m, 7H), 6.98 (t, J=7.5 Hz, 1H), 6.03 (s, 1H), 4.68 (d, J=12.0 Hz, 1H), 4.46 (d, J=12.0 Hz, 1H), 3.26-3.39 (m, 3H), 3.08 (m, 1H), 2.67 (br. s, 3H). APCI MS m/e: 300.0 ([M+H]$^+$).

Step 17G

The enantiomerically pure compounds 17-2 and 17-3 were obtained from racemic 17-1 (free base) by chiral preparative HPLC using a Chiralpak AD-H (20×250 cm) column eluting with 85:15 hexanes/ethanol containing 0.1% diethylamine at a flow rate of 15 mL/min. Each enantiomer was converted to the hydrochloride salt by treatment with hydrochloric acid (2M in diethyl ether).

Example 18

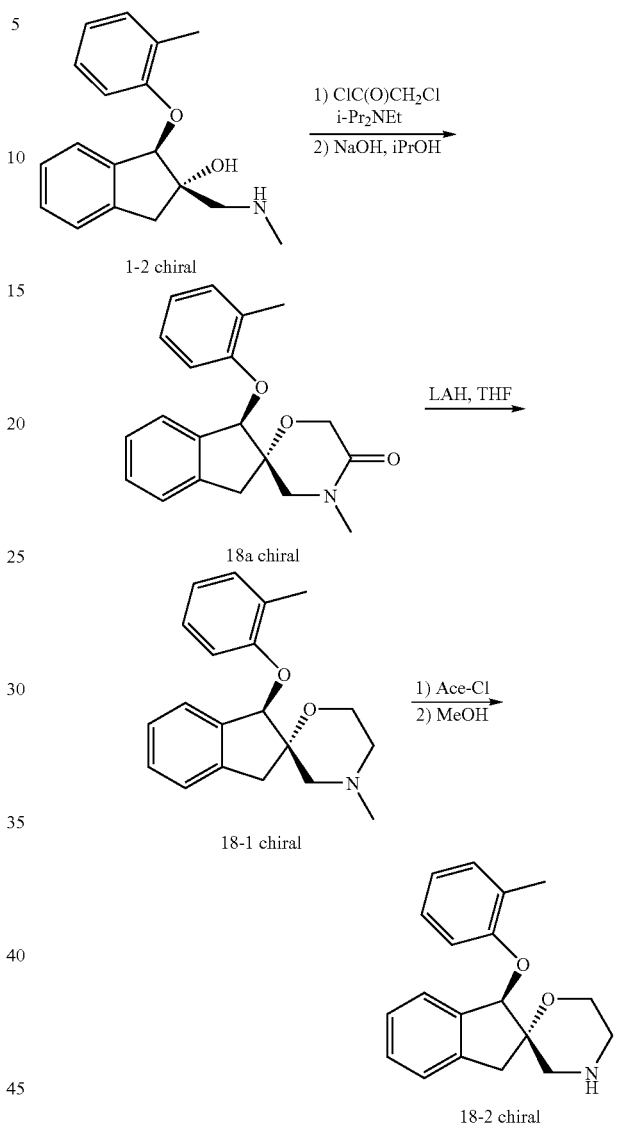

Step 18A

Amine 1-2 was converted to amide 18a following the procedures for steps 2D and 2E.

Step 18B

Amide 18a was converted to amine 18-1 following the procedure for step 2F. Purification of the crude product by silica gel chromatography eluting with dichloromethane containing 1% methanol and 0.5% triethylamine gave amine 18-1 (115 mg, 86%) as a pale yellow oil. APCI MS m/e: 310.1 ([M+H]$^+$).

Step 18C

To a stirred solution of the amine 18-1 (99 mg, 0.32 mmol) in dichloromethane (2 mL) was added N,N-diisopropylethylamine (106 μL, 0.64 mmol) followed by 2-chloroethylchloroformate (345 μL, 3.2 mmol). The mixture was stirred at ambient temperature for 1 h then concentrated in vacuo. The residue was dissolved in methanol (2 mL) and stirred at ambient temperature for 2.5 h then concentrated in vacuo. The residue was purified by silica gel chromatography eluting with 1 to 2% methanol in dichloromethane containing 0.5% triethylamine. Amine 18-2 (63 mg, 67%) was obtained as a pale yellow oil. APCI MS m/e: 295.8 ([M+H]⁺).

Example 19

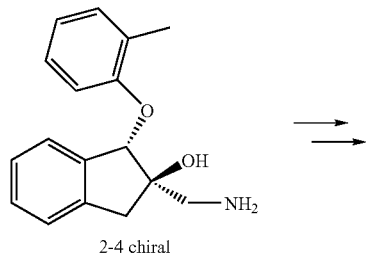

2-4 chiral

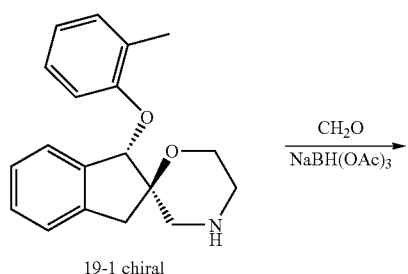

19-1 chiral

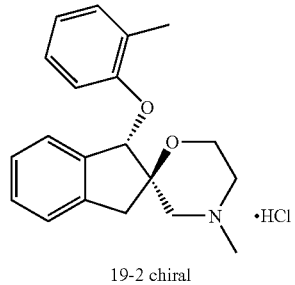

19-2 chiral

Step 19A

Primary amine 2-4 was converted into morpholine 19-1 following the procedures for steps 2D, 2E and 2F. ¹H-NMR and LCMS identical to 2-2.

Step 19B

To a solution of 19-1 (49 mg, 0.17 mmol) in 1,2-dichloroethane (1 mL) was added formaldehyde (37% in water, 15 µL, 0.2 mmol) and sodium triacetoxyborohydride (140 mg, 0.66 mmol). The mixture was stirred at ambient temperature for 1 h then quenched by the addition of 10% aqueous sodium hydroxide (1 mL). The mixture was extracted with dichloromethane (3×3 mL), the combined organics were dried over magnesium sulfate, filtered and concentrated in vacuo. The residue was dissolved in diethyl ether, hydrochloric acid (2M in diethyl ether, 90 µL) was added and the mixture was concentrated in vacuo, triturated with methyl-tert-butyl ether, filtered and dried in vacuo to afford 19-2 (18 mg, 37%) as an off-white solid. ¹H NMR (300 MHz, CDCl₃) δ 7.17-7.40 (m, 7H), 7.00 (m, 1H), 5.81 (s, 1H), 4.40 (m, 2H), 4.10 (m, 1H), 3.50 (m, 1H), 3.08-3.34 (m, 4H), 2.81 (d, J=3.0 Hz, 3H), 2.28 (s, 3H). APCI MS m/e: 310.1 ([M+H]⁺).

Example 20

5-Fluoro-2-methylaminomethyl-1-o-tolyloxy-indan-2-ol

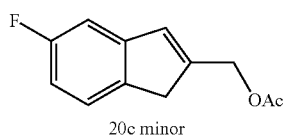

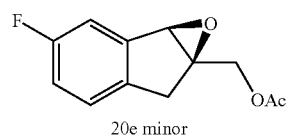

-continued

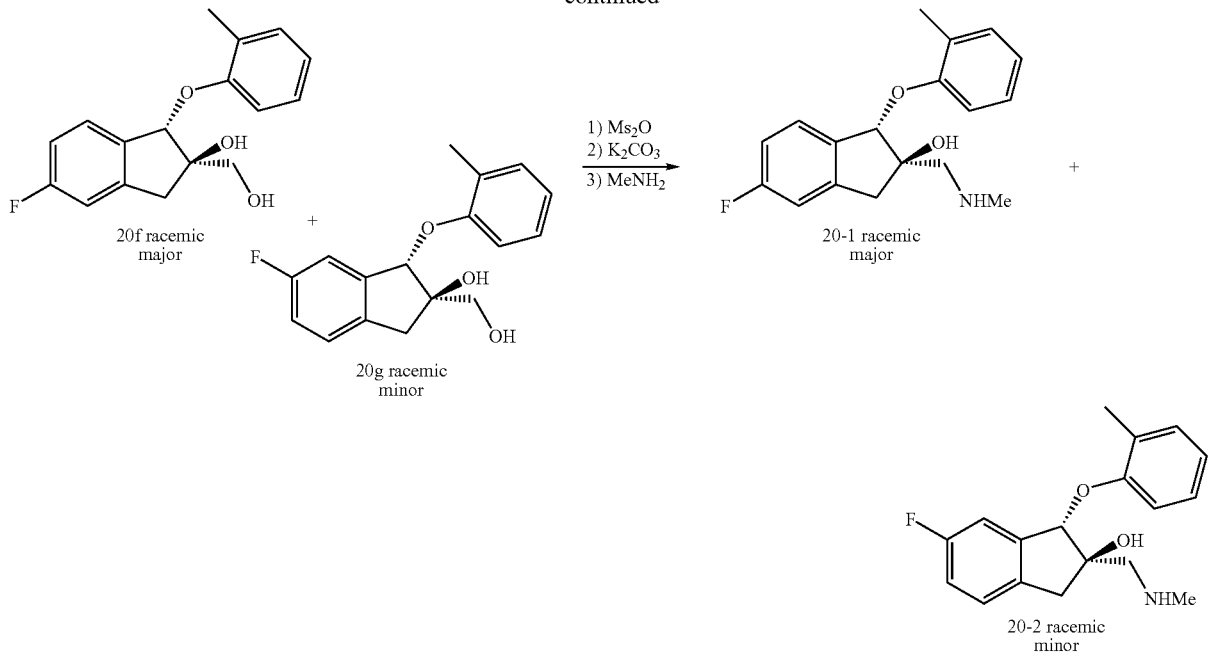

Step 20A

Alcohol 20a (obtained from 5-fluoro-1-indanone by the method as described in Steps 16A to 16C, 1.58 g, 9.6 mmol) was dissolved in triethyl amine (30 mL). Acetic anhydride (1.18 mL, 10.6 mmol) was added and the mixture was stirred at room temperature for 16 hours. The reaction mixture was partitioned between dichloromethane (30 mL) and saturated sodium bicarbonate solution (30 mL). The aqueous layer was extracted with dichloromethane (10 mL) and the combined organic extracts were dried over magnesium sulfate. Evaporation gave a mixture of 20b and 20c as a yellow oil (1.80 g) which was used without purification.

20b: $^1$H NMR (300 MHz, CDCl$_3$) δ 7.25 (dd, J=8.4, 4.8 Hz, 1H), 7.02 (dd, J=9.3, 2.7 Hz, 1H), 6.83-6.90 (m, 1H), 6.75 (s, 1H), 5.00 (s, 2H), 3.38 (s, 2H), 2.12 (s, 3H). APCI MS m/e: 248.1 ([M+CH$_3$CN+H]$^+$)

20c: $^1$H NMR (300 MHz, CDCl$_3$) δ 7.32 (dd, J=8.1, 4.8 Hz, 1H), 7.13 (dd, J=8.7, 1.8 Hz, 1H), 6.93-6.98 (m, 1H), 6.76 (s, 1H), 4.98 (s, 2H), 3.41 (s, 2H), 2.11 (s, 3H). APCI MS m/e: 248.1 ([M+CH$_3$CN+H]$^+$)

Step 20B

To a solution of olefins 20b and 20c (1.56 g, 7.5 mmol) in dichloromethane (30 mL), sodium bicarbonate (1.5 g, 18 mmol) was added. The mixture was cooled to 0° C. and treated with m-chloroperbenzoic acid (77%, 1.84 g, 8.2 mmol). The reaction mixture was allowed to warm up to room temperature overnight. A solution of saturated sodium bicarbonate (20 mL) was added and the layers were separated. The aqueous layer was extracted with dichloromethane (2×20 mL). The combined organics were dried over magnesium sulfate and evaporated. Silica gel chromatography using 10% ethyl acetate in hexanes afforded an inseparable mixture of epoxides 20d and 20e (1.10 g, 58% over 3 steps).

20d: $^1$H NMR (300 MHz, CDCl$_3$) δ 7.17 (dd, J=7.8, 2.1 Hz, 1H), 7.15-7.17 (m, 1H), 6.92-6.96 (m, 1H), 4.65 (d, J=12.3 Hz, 1H), 4.36 (d, J=12.3 Hz, 1H), 4.22 (s, 1H), 3.20 (d, J=17.7 Hz, 1H), 3.00 (d, J=17.4 Hz, 1H), 2.13 (s, 3H). APCI MS m/e: 264.0 ([M+CH$_3$CN+H]$^+$)

20e: $^1$H NMR (300 MHz, CDCl$_3$) δ 7.41 (dd, J=8.4, 5.1 Hz, 1H), 6.85-6.99 (m, 2H), 4.65 (d, J=12.3 Hz, 1H), 4.35 (d, J=12.3 Hz, 1H), 4.22 (s, 1H), 3.23 (d, J=18.0 Hz, 1H), 3.04 (d, J=17.4 Hz, 1H), 2.13 (s, 3H). APCI MS m/e: 264.0 ([M+CH$_3$CN+H]$^+$)

Step 20C

To a solution of sodium hydroxide (204 mg, 5.1 mmol) in water (204 µL) and acetonitrile (3 mL), o-cresol (584 mg, 5.4 mmol) was added and the mixture was heated at 50° C. for five minutes. The epoxide mixture 20d and 20e (1.10 g, 4.9 mmol) was added next and the reaction mixture was heated at 60° C. for 1.5 hours and 80° C. for 2.5 hours. The reaction mixture was diluted with a saturated solution of sodium chloride (30 mL) and extracted with ethyl acetate (3×30 mL). The combined organic layers were dried over magnesium sulfate and evaporated. Flash column chromatography on silica gel using 20% ethyl acetate in hexanes afforded 20f and 20g as an inseparable mixture (1.12 g, 79%).

20f: $^1$H NMR (300 MHz, CDCl$_3$) δ 6.93-7.23 (m, 7H), 5.76 (s, 1H), 4.08 (m, 1H), 3.66 (m, 1H), 3.00-3.21 (m, 3H), 2.27 (m, 1H), 2.19 (s, 3H). APCI MS m/e: 271.0 ([M+H−H$_2$O]$^+$)

20g: $^1$H NMR (300 MHz, CDCl$_3$) δ 6.93-7.23 (m, 7H), 5.70 (s, 1H), 4.08 (m, 1H), 3.66 (m, 1H), 3.00-3.21 (m, 3H), 2.27 (m, 1H), 2.14 (s, 3H). APCI MS m/e: 271.0 ([M+H−H$_2$O]$^+$)

Step 20D

The diol mixture 20f and 20g (525 mg, 1.82 mmol) was dissolved in dichloromethane (10 mL) and cooled to 0° C. Methanesulfonic anhydride (332 mg, 1.91 mmol) and Hünig's base (0.39 mL, 2.37 mmol) were added and the reaction mixture was allowed to warm up room temperature overnight. More methanesulfonic anhydride (158 mg, 0.91 mmol) and Hünig's base (0.18 mL, 1.09 mmol) were added.

After one hour, a saturated solution of sodium bicarbonate (20 mL) was added and the layers were separated. The aqueous layer was extracted with dichloromethane (2×10 mL) and the combined organics were dried and evaporated. The residue was dissolved in N,N-dimethylacetamide (4 mL) and transferred to a capped vial. Potassium carbonate (753 mg, 5.46 mmol) was added to this solution and the resulting suspension was stirred at room temperature for 45 minutes. A solution of methylamine in methanol (2.0 M, 4.5 mL) was added next and the mixture was heated at 70° C. for two hours and 80° C. for three hours. The reaction mixture was partitioned between a saturated solution of sodium bicarbonate (10 mL) and ethyl acetate (5 mL). The layers were separated and the aqueous layer was extracted with ethyl acetate (2×5 mL). The combined organics were dried and evaporated. Chromatography on silica gel using 5-7% methanol in dichloromethane, containing 0.05% triethlyamine as eluent afforded the mixture of amines 20-1 and 20-2 as a yellow oil (100 mg, 18%).

20-1: $^1$H NMR (300 MHz, CDCl$_3$) δ 7.08-7.27 (m, 4H), 6.86-6.98 (m, 3H), 5.62 (s, 1H), 3.24 (d, J=12.3 Hz, 1H), 3.07-3.11 (m, 2H), 2.66 (d, J=12.3 Hz, 1H), 2.47 (s, 3H), 2.16 (s, 3H). APCI MS m/e: 302.0 ([M+H]$^+$)

20-2: $^1$H NMR (300 MHz, CDCl$_3$) δ 7.08-7.277.08-7.27 (m, 4H), 6.80-6.98 (m, 3H), 5.55 (s, 1H), 3.28 (d, J=12.3 Hz, 1H), 3.07-3.11 (m, 2H), 2.70 (d, J=11.4 Hz, 1H), 2.48 (s, 3H), 2.10 (s, 3H). APCI MS m/e: 302.0 ([M+H]$^+$)

Following the same procedure, a mixture of the (1R,2S and 1S,2R)-5-Methoxy-2-methylaminomethyl-1-o-tolyloxy-indan-2-ol 16-1 and (1R,2S and 1S,2R)-6-Methoxy-2-methylaminomethyl-1-o-tolyloxy-indan-2-ol 20-3 were obtained starting with (6-methoxy-1H-inden-2-yl)-methanol.

Example 21

((1R,2S)-2-Methoxy-1-o-tolyloxy-indan-2-ylmethyl)-methyl-amine

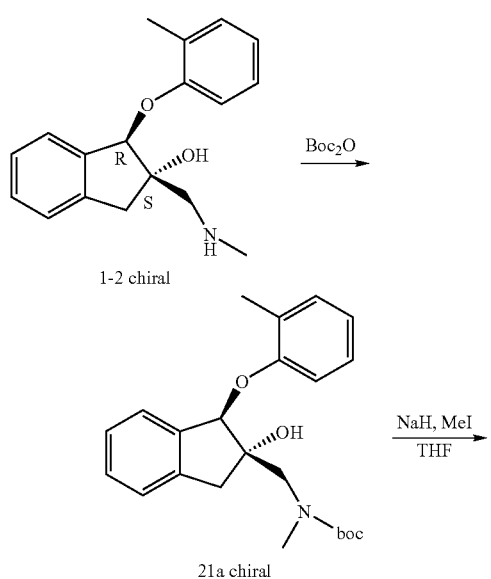

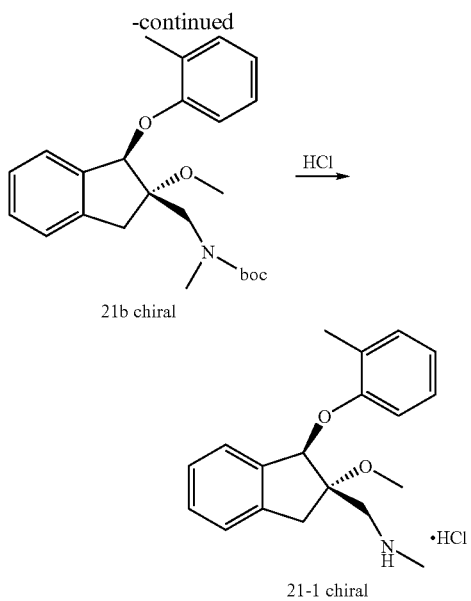

Step 21A

To a solution of 1-2 (125 mg, 0.44 mmol) and triethylamine (244 µL, 1.76 mmol) in dichloromethane (2 mL) was added di-tert-butyl-dicarbonate (104 mg, 0.48 mmol). The mixture was stirred at ambient temperature for 3 h. The mixture was diluted with dichloromethane (50 mL) and washed with 0.3M aqueous hydrochloric acid (2×50 mL). The combined organics were dried over magnesium sulfate, filtered and concentrated in vacuo to afford 21a (162 mg, 96%) as a pale yellow oil. APCI MS m/e: 283.9 ([M+H-Boc]$^+$).

Step 21B

To a suspension of sodium hydride (60% in mineral oil, 25 mg, 0.63 mmol) in tetrahydrofuran (1 mL) was added a solution of 21a (162 mg, 0.42 mmol) in tetrahydrofuran (1 mL). The mixture was stirred at ambient temperature for 20 min. then iodomethane (78 µL, 1.26 mmol) was added and the resultant mixture was stirred at ambient temperature for a further 24 h. A further portion of sodium hydride (60% in mineral oil, 25 mg, 0.63 mmol) was added followed by iodomethane (78 µL, 1.26 mmol) and stirring continued at ambient temperature for a further 24 h. The reaction was diluted with ethyl acetate (50 mL) and washed with 1 M aqueous hydrochloric acid (50 mL). The aqueous layer was back extracted with ethyl acetate (50 mL) and the combined organics were dried over magnesium sulfate, filtered and concentrated in vacuo. The residue was purified by preparative HPLC to afford 21b (19 mg, 11%) as a colorless oil. APCI MS m/e: 298.0 ([M+H-Boc]$^+$).

Step 21C

To a stirred solution of 21b (19 mg, 0.05 mmol) in ethanol (1 mL) was added hydrochloric acid (2M in diethyl ether, 125 µL, 0.25 mmol). The mixture was stirred at 50° C. for 16 h and concentrated in vacuo. Diethyl ether (2 mL) was added and the suspension was concentrated in vacuo to afford 21-1 (15 mg, quant.) as a white solid. $^1$H NMR (300 MHz, CDCl$_3$) δ 7.10-7.30 (m, 7H), 6.95 (m, 1H), 5.90 (s, 1H), 3.25-3.73 (m, 7H), 2.84 (s, 3H), 2.09 (s, 3H). APCI MS m/e: 298.0 ([M+H]$^+$).

Example 22

3-Allyloxy-2-methyl-phenol

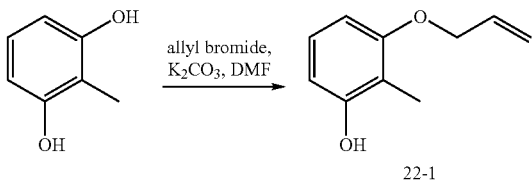

Step 22A

To a solution of 2-methylresorcinol (2.5 g, 20.2 mmol) in DMF (10 mL) was added potassium carbonate (3.3 g, 24.2 mmol) and allyl bromide (1.7 mL, 20.2 mmol). The mixture was stirred at ambient temperature for 16 h. The mixture was diluted with de-ionized water (75 mL) and extracted with ethyl acetate (3×50 mL). The combined ethyl acetate layers were washed with 0.1M aqueous hydrochloric acid (50 mL), dried over magnesium sulfate, filtered and concentrated in vacuo to afford 22-1 (1.06 g, 32%) as a yellow oil. $^1$H NMR (300 MHz, CDCl$_3$) δ 7.00 (t, J=8.4 Hz, 1H), 6.47 (d, J=8.4 Hz, 1H), 6.45 (d, J=8.4 Hz, 1H), 6.07 (m, 1H), 5.42 (ddt, J=17.1, 3.0 and 1.5 Hz, 1H), 5.27 (ddt, J=10.8, 3.0 and 1.5 Hz, 1H), 4.67 (br. s, 1H), 4.53 (m, 2H), 2.15 (s, 3H).

Example 23

Inhibition of Radioligand Transport by HEK293 Cells Expressing Human Norepinephrine, Dopamine, or Serotonin Transporters The norepinephrine, dopamine, and serotonin transporters were individually expressed in stably transfected HEK293 cell lines and grown in Dulbecco's Modified Eagles Medium (DMEM) (Cellgro, 15-013-CV) with the following supplements: 1% HEPES (Cellgro, MT 25-060-Cl); 1% L-glutamine (Cellgro, MT 25-005-Cl); 1% sodium pyruvate (Cellgro, MT 25-000Cl); 1% Pen/Strep (Cellgro, MT 30-001-Cl); 10% heat-inactivated fetal bovine serum (FBS) (Hyclone, Logan, Utah); 250 µg/ml G418 (Cellgro, 61-234-RG).

The day before the assay, solid white 96-well TC-treated sterile plates (Costar, 3917) that had been coated with 0.01% poly-D-lysine (Sigma, P6407) and 0.01% collagen (BD Biosciences, 354236) were seeded with cells at a density of 20,000 cells/well. The cells were allowed to attach overnight in a 37° C. incubator (7.5% CO$_2$). On the day of the assay, media was removed, and cells were washed with phosphate buffered saline. The cells were then incubated at room temperature for 20 minutes with varying concentrations of competing ligand in a total volume of 150 µl transport buffer (20 mM HEPES, 122 mM NaCl, 3 mM KCl, 1.3 mM CaCl$_2$, 1.2 mM KH$_2$PO$_4$, 0.4 mM MgSO$_4$, 1 mM ascorbic acid, 0.1 mM pargyline, 0.1 mM tropolone). Radioligand was then added to the cells for a total volume of 200 µl, and cells were incubated at room temperature for an additional 20 minutes. (Levo-[ring-2,5,6-$^3$H] Norepinephrine (52 Ci/mmol, PerkinElmer, NET-678) was used for NET, 3,4-[ring-2,5,6-$^3$H] Dihydroxyphenylethylamine (50 Ci/mmol, PerkinElmer, NET-673) was used for DAT, and [alpha, beta-$^3$H(N)] 5-Hydroxytryptamine (30 Ci/mmol, PerkinElmer, NET-498) was used for SERT.) After incubation, the transport buffer was quickly aspirated from the plates, and the cells were washed twice with 4° C. wash buffer (20 mM HEPES, 280 mM D-mannitol, 5.4 mM KCl, 1.8 mM CaCl$_2$, 0.8 mM MgSO$_4$, 1 mM ascorbic acid, 0.1 mM pargyline, 0.1 mM tropolone). Cells were treated with 50 µl 5% sodium dodecyl sulfate solution (Sigma, L4522) and 200 µl Microscint scintillation fluid. Plates were shaken vigorously overnight before monitoring radioligand in a TopCount-NXT (Packard) microplate scintillation counter. Data were analyzed by nonlinear, least-squares curve fitting algorithms using ActivityBase (IDBS, Guildford, Surrey, UK).

Example 24

Radioligand Binding to Human NET Transporter Expressed in Mammalian Cell Lines Crude membranes were prepared by differential centrifugation from HEK293 cells stably transfected with the human norepinephrine transporter. Membranes (3 µg of protein) were incubated for 2 hours with 1.5 nM [$^3$H] Nisoxetine (86 Ci/mmol, PerkinElmer, NET-1084) in the presence of varying concentrations of competing ligand. Non-specific binding was determined in the presence of excess (1 µM) desipramine. Reactions were terminated by rapid vacuum filtration using a Packard 96-well cell harvester over PEI soaked (1%) (Sigma, P3143) GF/C membrane filter plates (Packard, 6005174). The filter plates were then washed with 600 µl phosphate buffered saline containing 0.01% (v/v) Triton-X100 and dried under forced air fans. Microscint scintillation fluid was added to each well before monitoring bound radioligand in a TopCount-NXT (Packard) microplate scintillation counter. Binding data were analyzed by nonlinear, least-squares curve fitting algorithms using ActivityBase (IDBS, Guildford, Surrey, UK).

Example 25

Formalin Flinch Assay

The formalin test is conducted using the Automated Nociception Analyzer (Department of Anesthesiology, University of California, San Diego, Yaksh et al, 2001). One hour prior to testing, a metal band is glued to a rat's left hind paw. The animal is then put in a testing chamber. Animals are dosed with compound orally at volumes equal to or less than 10 mg/ml with either vehicle (5% Cremophor® in milliQ water) or active compounds (1-100 mg/kg) one hour prior to formalin injection. As a positive control, rats are dosed with ethosuximide at 600 mg/kg orally. Animals are injected with 50 µl of 5% formalin solution (20-fold dilution of a 37% stock from Fisher Chemicals) subcutaneously on dorsal surface of the left hind paw. The number of flinches is recorded for each minute for one hour by detecting the movement of a metal paw band with a localized low strength sinusoidal electromagnetic field. Drug effects are analyzed by a one-way ANOVA on each phase {Phase I (0-9 minutes), Phase IIA (10-40 minutes), and Phase IIB (41-60 minutes)}. Significant effects are analyzed by Dunnett's post hoc comparison to vehicle.

Example 26

Spinal Nerve Ligation Assay

Neuropathy is induced by Spinal Nerve Ligation (SNL) surgery (Kim and Chung, 1992). Briefly, in rats, the left L5 and L6 spinal neurons distal to the dorsal root ganglion are tightly ligated with 6-0 silk suture. At 4-12 weeks post-surgery, the rats are tested for mechanical hyperalgesia using the pin prick method (Koch et al, 1996). The length of time the paw is held off the grid-floor is measured with a computer program Xnote Stopwatch ver1.4. Zero seconds is assigned when there is no paw withdrawal. The baseline score is determined from the average of five trials. Baselines are counterbalanced for assignments into treatment groups. Animals are dosed with compound orally at volumes equal to or less than 10 mg/ml with either vehicle (5% Cremophor® in milliQ water) or active compounds (1-100 mg/kg) one hour prior to assessment of withdrawal in response to the pin prick. Drug effects are analyzed by a two-way ANOVA with treatment and time as variables. Significant effects are analyzed by Dunnett's post hoc comparison.

Kim S H, Chung J M., An experimental model for peripheral neuropathy produced by segmental spinal nerve ligation in the rat., Pain. 1992 September; 50(3):355-63.

Koch B D, Faurot G F, McGuirk J R, Clarke D E, Hunter J C., Modulation of mechano-hyperalgesia by clinically effective analgesics in rats with a peripheral mononeuropathy. Analgesia. 1996; Vol 2:157-164.

Yaksh T L, Ozaki G, McCumber D, Rathbun M, Svensson C, Malkmus S, Yaksh M C., An automated flinch detecting system for use in the formalin nociceptive bioassay. J Appl Physiol. 2001 June; 90(6):2386-402.

Example 27

Microdialysis Procedure for the Determination of Monoamine Levels

Surgery: Animals were anaesthetized with isoflorane, and a servo-controlled heating pad maintained body temperature throughout the surgery. Animals were placed in a stereotaxic instrument and an incision was made down the mid-line over the skullcap. Miniature bone screws were inserted individually into the occipital, parietal and frontal skull plates. Two small holes (1.8 mm diameter) were drilled with microtrephines for stereotaxic insertion of guide cannulae, one in the left frontal plate (3.1 mm anterior and 1.2 mm lateral to bregma) and a second in the right parietal plate (0.5 mm posterior and 4.4 mm lateral to bregma). Guide cannulae were lowered into the brain at a rate of 0.2 mm/min and at an angle of 5° to the following depths: 2.0 mm (left frontal cannula) and 3.0 mm (right striatal cannula). The dialysis membranes of the microdialysis probes have a 3.0 mm length and extend 3.0 mm past the ends of the implanted cannulae so the final depths of inserted probes were 3.0 mm and 6.0 mm for the PFC and striatal probes respectively. The sampled brain regions correspond to (1) left prefrontal cortex (PFC), including mainly anterior cingulate and prelimbic cortices, and (2) right striatum (caudate-putamen) mainly, but also including to a small degree in some animals, lateral globus pallidus. Cannulae were secured with dental cement to the skull and bone screws. The skin incision was closed with 4-0 suture and Vetbond (3-M). Animals received immediate post-operative care and were allowed one full week to recover from surgery. Animals were housed in 12:12 light-dark room (lights off at 7AM).

Microdialysis procedure: After a 1-week recovery, animals were placed in individual Raturn bowls for microdialysis sampling (Bioanalytical Systems, Inc., West Lafayette, Ind.). The capped stylets that cover the cannulae and maintain their patency were removed, and microdialysis probes were inserted manually at a slow rate. Probe membranes protruded 3.0 mm from the cannula tips and sampled extracellular fluid over this entire 3.0 mm length. The input tube of each microdialysis probe was connected to a syringe pump (CMA/102, CMA Microdialysis, North Chelmsford, Mass.) that delivered artificial cerebrospinal fluid (aCSF). aCSF had the following composition: 154.7 mM $Na^+$, 2.9 mM $K^+$, 1.1 mM $Ca^{2+}$, 0.82 mM $Mg^{2+}$, 132.49 mM $Cl^-$ (pH 7.4). The output tubes of each probe were connected to a refrigerated fraction collection system (Honeycomb, Bioanalytical Systems, Inc.). Animals were allowed 14-16 hrs to recover from probe insertion and to habituate to the bowl and tether. Probes were perfused over this time period at a slow rate of 0.2 µL/min. On the following morning, pump perfusion rates were increased to 1.1 µL/min at the time of lights off (7 AM). Dialysate sampling began 1 hr later. Individual samples were collected over a 30 min time period. After 1.5 hrs of baseline sampling (3 samples), either vehicle (5% Cremophor in MillQ water) or NBI compound, which was prepared in vehicle solution, was administered orally at doses of either 1, 3 or 10 mg/kg and at a dose volume of 5 mL/kg. Sampling was continued for 6 hrs after dosing (12 post-dose samples). At the end of the study, sampling carousels were removed and transported to the HPLC-electrochemical detection system. Animals were euthanized with $CO_2$ and decapitated. Brains were immediately removed and prepared for histology by inserting the brains briefly (1 min) into −40° C. 2-methylbutane. Brain areas of interest (left frontal region, ~2-4 mm rostral to bregma, and right midline region, ~0-2 mm caudal to bregma) were sectioned coronally with a cryostat and sections were prepared for histological examination of probe placement and depth.

HPLC-EC detection and analysis: Monoamine levels in microdialysis samples were measured by HPLC-electrochemical detection (EC). 27 uL was withdrawn from individual microdialysis samples and injected onto an HPLC-EC system consisting of a pulse-free pump (Model 582 Solvent Delivery System; ESA Instruments, Chelmsford, Mass.), a 2 mm×15 cm, 3 um particle size LC column (70-4129; ESA Instruments), and an electrochemical detector (Coulochem III; ESA Instruments). The mobile phase consisted of 0.05 M citrate, 1.00 mM OSA, 0.1 mM EDTA, 6.5% methanol, and pH=4.85, and resulted in retention times of approximately 4", 12" and 34" for NE, DA and 5-HT, respectively. The optimal detection settings for the detector were the following: working electrode=+300 mV, reference electrode #1=+200 mV, reference electrode #2=−120 mV, signal filter=0.1 Hz, range=1.0 nA. Chromatograms were analyzed manually off-line (EZChrome Elite software; Agilent Technologies, Pleasantown, Calif.) to determine peak areas for NE (norepinephrine), DA (dopamine) and 5-HT. Daily analysis of monoamine standards showed the quantitative limits for NE, DA and 5-HT was approximately 0.2-0.5 pg per 27 uL of sample. Peak values for each sample were normalized to the mean peak value of the first three baseline samples for each monoamine using Micosoft Excel. Normalized data were imported into GraphPad Prism (GraphPad Software, San Diego, Calif.) for graphical analysis and to test for significant differences between treatment groups using repeated measures, two-way ANOVA for treatment (different dose groups: vehicle, 1, 3 and 10 mg/kg) and time (15 time points). If significant interaction effects were observed, pair-wise post-hoc group comparisons were made using Tukey's least significant difference procedure to test for significant effects of treatment at each time point.

It will be appreciated that, although specific embodiments of the invention have been described herein for purposes of illustration, various modifications may be made without departing from the spirit and scope of the invention. Accordingly, the invention is not limited except as by the appended claims.

What is claimed is:

1. A compound having the following structure:

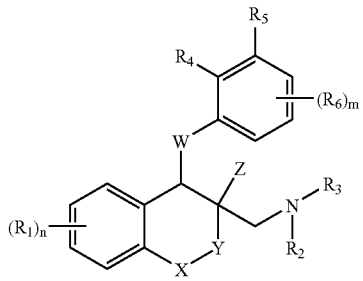

or a stereoisomer or pharmaceutically acceptable salt thereof, wherein:
W is —CH$_2$—, O or S;
X—Y is —CH$_2$—, or —CH$_2$CH$_2$;
Z is F, OH, lower alkoxy, or substituted lower alkoxy;
R$_1$ at each occurrence is independently halo, CN, CF$_3$, OH, lower alkyl, lower alkoxy, or lower thioalkyl;
R$_2$, R$_3$ are independently H, lower alkyl, or substituted lower alkyl;
R$_4$, R$_5$ are independently H, halo, CN, CF$_3$, OH, lower alkyl, substituted lower alkyl, lower alkoxy, substituted lower alkoxy, lower thioalkyl, or substituted lower thioalkyl;
R$_6$ is at each occurrence independently H, halo, CN, CF$_3$, OH, lower alkyl, substituted lower alkyl, lower alkoxy, or lower thioalkyl;
m is 0, 1, 2, or 3; and
n is 0, 1, 2 or 3.

2. The compound of claim 1 wherein —X—Y— is —CH$_2$—.

3. The compound of claim 1 wherein —X—Y— is —CH$_2$CH$_2$—.

4. The compound of claim 1 wherein W is —CH$_2$—.

5. The compound of claim 1 wherein W is O.

6. The compound of claim 1 wherein W is S.

7. The compound of claim 2 wherein W is O.

8. The compound of claim 7 wherein R$_3$ is lower alkyl.

9. The compound of claim 8 wherein Z is OH.

10. The compound of claim 9 wherein R$_4$ is halo or lower alkyl.

11. The compound of claim 10 wherein R$_5$ or R$_6$ is halo.

12. The compound of claim 1 wherein Z is OH.

13. The compound of claim 12 wherein —X—Y— is —CH$_2$—.

14. The compound of claim 13 wherein W is O or S.

15. A pharmaceutical composition comprising a compound of claim 1 and a pharmaceutically acceptable carrier or diluent.

* * * * *